United States Patent
Fiedler et al.

(10) Patent No.: US 10,370,414 B2
(45) Date of Patent: *Aug. 6, 2019

(54) BINDING PROTEINS COMPRISING AT LEAST TWO REPEAT DOMAINS AGAINST HER2

(71) Applicant: Molecular Partners AG, Zurich-Schlieren (CH)

(72) Inventors: Ulrike Fiedler, Lorrach (DE); Ignacio Dolado, Rheinfelden (CH); Heike Strobel, Zurich (CH)

(73) Assignee: Molecular Partners AG, Zurich-Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/648,611

(22) PCT Filed: Dec. 2, 2013

(86) PCT No.: PCT/EP2013/075290
§ 371 (c)(1),
(2) Date: May 29, 2015

(87) PCT Pub. No.: WO2014/083208
PCT Pub. Date: Jun. 5, 2014

(65) Prior Publication Data
US 2015/0299265 A1  Oct. 22, 2015

(30) Foreign Application Priority Data

Nov. 30, 2012 (EP) .................................... 12195156

(51) Int. Cl.
| | |
|---|---|
| *A61K 38/00* | (2006.01) |
| *C07K 14/00* | (2006.01) |
| *C07K 14/47* | (2006.01) |
| *C07K 16/32* | (2006.01) |

(52) U.S. Cl.
CPC ............ *C07K 14/001* (2013.01); *C07K 14/47* (2013.01); *C07K 16/32* (2013.01); *A61K 38/00* (2013.01); *C07K 2317/31* (2013.01); *C07K 2317/34* (2013.01); *C07K 2317/35* (2013.01); *C07K 2317/73* (2013.01); *C07K 2317/92* (2013.01); *C07K 2318/20* (2013.01); *C07K 2319/21* (2013.01)

(58) Field of Classification Search
None
See application file for complete search history.

(56) References Cited

U.S. PATENT DOCUMENTS

| | | | |
|---|---|---|---|
| 7,417,130 B2 | 8/2008 | Stumpp et al. | |
| 8,110,653 B2 | 2/2012 | Stumpp et al. | |
| 8,710,187 B2 | 4/2014 | Binz et al. | |
| 8,722,618 B2 | 5/2014 | Jacobs et al. | |
| 8,846,577 B2 | 9/2014 | Steiner et al. | |
| 8,901,076 B2 | 12/2014 | Binz et al. | |
| 9,006,389 B2 | 4/2015 | Stumpp et al. | |
| 2010/0260668 A1 | 10/2010 | Ghayur et al. | |
| 2011/0033460 A1 | 2/2011 | Fendly et al. | |
| 2011/0224100 A1 | 9/2011 | Parmeggiani et al. | |
| 2013/0244940 A1 | 9/2013 | Steiner et al. | |
| 2013/0296221 A1 | 11/2013 | Binz | |
| 2014/0005125 A1 | 1/2014 | Baumann | |
| 2014/0206599 A1 | 7/2014 | Baumann et al. | |
| 2014/0221295 A1 | 8/2014 | Binz et al. | |
| 2015/0057186 A1 | 2/2015 | Steiner et al. | |
| 2015/0275201 A1 | 10/2015 | Stumpp et al. | |
| 2015/0284463 A1 | 10/2015 | Tamaskovic et al. | |

FOREIGN PATENT DOCUMENTS

| | | | |
|---|---|---|---|
| WO | WO 2009/068625 A2 | 6/2009 | |
| WO | 2011/054519 A1 | 5/2011 | |
| WO | 2012/162418 A1 | 11/2012 | |
| WO | WO 2014/191574 A1 | 12/2014 | |

OTHER PUBLICATIONS

Amstutz et al., "Intracellular Kinase Inhibitors Selected from Combinatorial Libraries of Designed Ankyrin Repeat Proteins", JBC (2005) vol. 280 No. 26, 24715-24722.

Amstutz et al., "Rapid selection of specific MAP kinase-binders from designed ankyrin repeat protein libraries," Protein Engineering, Design & Selection (2006) 19(5), p. 219-29.

Berns et al., "A functional genetic approach identifies the PI3K pathway as a major determinant of trastuzumab resistance in breast cancer", Cancer Cell (2007) 12, p. 395-402.

Binz et al., "Crystal Structure of a Consensus-Designed Ankyrin Repeat Protein: Implications for Stability," Proteins: Structure, Function, and Bioinformatics 65:280-84 (2006).

Binz et al., "Designed Repeat Proteins—Molecules with Antibody-like Binding Properties," BIOforum Europe Apr. 2005, pp. 34-36, GIT VERLAG GmbH & Co. KG, Darmstadt.

Binz et al., "Engineered proteins as specific binding reagents," Current Opinion in Biotechnology (2005) 16, p. 459-469.

Binz et al., "Engineering novel binding proteins from nonimmunoglobulin domains," Nature Biotechnology (2005) 23(10), p. 1257-1268.

Binz et al., "High-affinity binders selected from designed ankyrin repeat protein libraries", Nature Biotechnology (2004) 22(5), p. 575-582.

Binz, "Designing Repeat Proteins: Well-expressed, Soluble and Stable Proteins from Combinatorial Libraries of Consensus Ankyrin Repeat Proteins" J Mol Biol (2003) 332, 489-503.

Boersma et al., "DARPins and other repeat protein scaffolds: advances in engineering and applications," Curr Opin Biotechnol (2011) 22(6), p. 849-57.

(Continued)

*Primary Examiner* — James H Alstrum-Acevedo
*Assistant Examiner* — Tara L Martinez
(74) *Attorney, Agent, or Firm* — Finnegan, Henderson, Farabow, Garrett & Dunner LLP

(57) ABSTRACT

The present invention relates to a recombinant binding protein comprising at least a first and a second repeat domain, wherein each of said two repeat domains binds the extracellular region of HER2 and wherein said repeat domains are covalently linked.

23 Claims, 11 Drawing Sheets

Specification includes a Sequence Listing.

(56) References Cited

OTHER PUBLICATIONS

Bublil E.M. and Yarden Y., "The EGF receptor family: spearheading a merger of signaling and therapeutics", Curr. Opin. Cell Biol. (2007) 19(2), p. 124-34.
Burgess et al., "An Open-and-Shut Case? Recent Insights into the Activation of EGF/ErbB Receptor", Molecular Cell (2003) 12(3), p. 541-552.
Capelan et al., "Pertuzumab: new hope for patients with HER2-positive breast cancer", Annals of Oncology (2013) 24, p. 273-282.
Eggel et al., "DARPins as Bispecific Receptor Antagonists Analyzed for Immunoglobulin E Receptor Blockage", J Mol Biol (2009) 393, p. 598-607.
Forrer et al., "A novel strategy to design binding molecules harnessing the modular nature of repeat proteins," FEBS Letters (2003) 539, p. 2-6.
Forrer et al., "Consensus Design of Repeat Proteins," ChemBioChem (2004) 5, p. 183-189.
Hanes et al., "In vitro selection and evolution of functional proteins by using ribosome display," Proc Natl Acad Sci USA (1997) 94(10), p. 4937-42.
He et al., "Ribosome display: cell-free protein display technology," Brief Funct Genomic Proteomic (2002) 1(2), p. 204-12.
Interlandi et al., "Characterization and Further Stabilization of Designed Ankyrin Repeat Proteins by Combining Molecular Dynamics Simulations and Experiments," J Mol Biol (2008) 375(3), p. 837-54.
Jost et al., "Structural Basis for Eliciting a Cytotoxic Effect in HER2-Overexpressing Cancer Cells via Binding to the Extracellular Domain of HER", Structure (2013) 21(11), p. 1979-1991.
Kawe et al., "Isolation of Intracellular Proteinase Inhibitors Derived from Designed Ankyrin Repeat Proteins by Genetic Screening," J Biol Chem (2006) 281, p. 40252-63.
Kohl et al., "Designed to be stable: Crystal structure of a consensus ankyrin repeat protein", PNAS (2003) 100(4), p. 1700-1705.
Kramer et al., "Structural Determinants for Improved Stability of Designed Ankyrin Repeat Proteins with a Redesigned C-Capping Module", J Mol Biol (2010) 404, p. 381-391.
Sennhauser et al., "Chaperone-Assisted Crystallography with DARPins", Structure (2008) 16, p. 1443-1453.
Steiner et al., "Efficient Selection of DARPins with Sub-nanomolar Affinities using SRP Phage Display", J Mol Biol 2008, 382(5), p. 1211-1227 (incl. Supplement).
Stumpp et al., "DARPins: A new generation of protein therapeutics", Drug Discovery Today (2008) 13(1516), p. 695-701.
Stumpp et al., "Designing Repeat Proteins: Modular Leucine-rich Repeat Protein Libraries Based on the Mammalian Ribonuclease Inhibitor Family", J Mol Biol (2003) 332, 471-487.
Theurillat et al., "Designed ankyrin repeat proteins: a novel tool for testing epidermal growth factor receptor 2 expression in breast cancer", Modern Pathology (2010), 23(9) p. 1289-1297.
Veesler et al., "Crystal Structure and Function of a DARPin Neutralizing Inhibitor of Lactococcal Phage TP901-1. Comparison of DARPin and Camelid VHH Binding Mode.", J Biol Chem (2009) 284(44), p. 30718-30726.
Zahnd et al., "Ribosome display: selecting and evolving proteins in vitro that specifically bind to a target," Nature Methods (2007) 4(3), p. 269-279.
Zahnd et al., "Selection and Characterization of Her2 Binding-designed Ankyrin Repeat Proteins," J Biol Chem (2006) 281(46), p. 35167-35175.
International Preliminary Report on Patentability for Application No. PCT/EP2013/075290, dated Jun. 2, 2015 (7 pages).
European Search Report for Application No. EP12195156.0, dated Apr. 25, 2013 (8 pages).
International Search Report and Written Opinion of the International Searching Authority for Application No. PCT/EP2013/075290, dated Mar. 25, 2014 (13 pages).
Nielsen et al., "Targeting of Bivalent Anti-ErbB2 Diabody Antibody Fragments to Tumor Cells Is Independent of the Intrinsic Antibody Affinity". Cancer Research, vol. 60, No. 22, Nov. 15, 2000: pp. 6434-6440.
Steffen et al., "In Vitro Characterization of a Bivalent Anti-HER-2 Affibody with Potential for Radionuclide-Based Diagnostics". Cancer Biotherapy & Radiopharmaceuticals, vol. 20, No. 3, Jan. 1, 2005: pp. 239-249.
Stumpp et al., "DARPins: A true alternative to antibodies". Current Opinion in Drug Discovery and Development, vol. 10, No. 2, Mar. 1, 2007: pp. 153-159.
Zahnd et al., "A Designed Ankyrin Repeat Protein Evolved to Picomolar Affinity to Her2". Journal of Molecular Biology, vol. 369, No. 4, May 17, 2007: pp. 1015-1028.
Zahnd et al., "Efficient Tumor Targeting with High-Affinity Designed Ankyrin Repeat Proteins: Effects of Affinity and Molecular Size". Cancer Research, vol. 70, Feb. 15, 2010: pp. 1595-1605.
Binz et al. *Nature Biotechnology*, 2004; 22(5): 575-582.
Sennhauser and Grütter. *Structure*, 2008; 16(10): 1443-1453.

BINDING PROTEINS COMPRISING AT LEAST TWO REPEAT DOMAINS AGAINST HER2

FIELD OF THE INVENTION

The present invention relates to binding proteins comprising at least two repeat domains with binding specificity for human epidermal growth factor receptor 2 (HER2), as well as nucleic acids encoding such HER2 binding proteins, pharmaceutical compositions comprising such proteins and the use of such proteins in the treatment of diseases.

BACKGROUND OF THE INVENTION

Human epidermal growth factor receptor 2 (HER2; human HER2 has the UniProtKB/Swiss-Prot number P04626) also known as ErbB2 is a protein that in humans is encoded by the ERBB2 gene. Amplification or over-expression of this gene has been shown to play an important role in the pathogenesis and progression of certain types of cancer and in recent years it has evolved to become an important biomarker and target of disease therapy. HER2 is a trans-membrane receptor tyrosine kinase (RTK) belonging to the wider family of ErbB receptors (Bublil, E. M. and Yarden, Y. Curr. Opin. Cell Biol. 19(2), 124-34, 2007). The ErbB receptor family is conserved across vertebrates and also includes the family founder ErbB1 (also named epidermal growth factor receptor (EGFR) or HER1; P00533 number in UniProKB/Swiss-Prot for the human protein) and the more recently identified receptors HER3 (also named ErbB3; P21860 number in UniProKB/Swiss-Prot for the human protein) and HER4 (also named ErbB4; Q15303 number in UniProKB/Swiss-Prot for the human protein). All ErbB receptors share extensive sequence and domain homologies, and form functional homodimers (e.g. ErbB1-ErbB1, HER2-HER2 and HER4-HER4) and heterodimers in all combinations. Receptor homo- and heterodimerization occurs upon ligand binding or receptor overexpression, and in turn activates intracellular receptor kinase domains by autophosphorylation. This then triggers downstream intracellular signaling and biological responses. In contrast to the other ErbB-receptors, HER2 does not have any known ligand and is able to dimerize, which is strongly pronounced after its overexpression and is thereby activated without previous ligand binding. Importantly, HER3 has no active intracellular kinase domain and is activated through heterodimerization with other ErbB receptor family members leading to very potent downstream signaling. Such heterodimerization and activation of HER3 occurs upon ligand binding to HER3 or if a partnering receptor, such as HER2, is strongly overexpressed.

HER2 as well as all the other ErbB receptor family members are composed of four extracellular domains, which are sequentially named I, II, III and IV; where domain IV is the closest to the extracellular cell membrane and domain I the most distal. In ligand-deprived conditions, domains I and III in ErbB receptors share an intramolecular interaction that occludes domain II. This prevents receptor homo-/heterodimerization and signaling, since interaction between domains II of two neighboring ErbB receptors is required for dimerization (Burguess A. W., et al., Mol. Cell 12(3), 541-552, 2003). Ligand binding disrupts the interaction between domains I and III, which then causes a tethered-to-extended receptor conformational change and leaves domain II exposed. This makes the receptor promiscuous to dimerize with other extended ErbB receptors and initiate signaling. Interestingly, HER2 is the only ErbB receptor family member that is constitutively found in an extended conformation; hence domain II is continuously exposed and accessible for homo- and heterodimerization.

ErbB receptor dimerization and autophosphorylation leads to the activation of a plethora of key downstream signaling molecules involved in normal physiology as well as in disease. The nature of such activated signaling molecules depends to some extend on the composition of the active ErbB receptor dimers. For instance, HER1-HER1 and HER2-HER2 homodimers preferentially activate downstream extracellular-signal-regulated kinase (ERK) signaling and proliferation, whereas HER2-HER3 heterodimers also activate the PI3K-signaling pathway (including activation of the downstream kinase AKT) and thereby cell survival. In fact, AKT activation by HER2-HER3 signaling in tumor cells promotes survival and makes tumor cells resistant to HER2 targeting drugs, such as the monoclonal antibody trastuzumab (Berns K. et al., Cancer Cell 12, 395-402, 2007). Interestingly, inhibition of HER2-HER3 mediated PI3K-AKT signaling in these cells becomes rate-limiting and results in cell death. Apart from cell proliferation and survival, HER2 signaling has been also causally involved in other processes such as angiogenesis and migration.

HER2 is overexpressed in approximately 20% of all breast cancers. Due to its clinical relevance, HER2 became the first RTK against which a targeted biological was developed, namely trastuzumab (Herceptin®; Genentech). This antibody binds to domain IV of HER2 and inhibits HER2 signaling by several mechanisms that are not yet completely understood. These include induction of receptor internalization in tumor cells, which results in reduced HER2 expression levels and signaling and leads to an attenuated tumorigenic phenotype. Trastuzumab has changed the life of tens of thousands of breast cancer women, expanding their lifetime and quality of life. However, trastuzumab has mainly an anti-proliferative effect and tumors may escape from such treatment in advanced disease stages. In an attempt to develop more efficacious treatments, a new antibody was generated that recognized domain II or HER2, namely pertuzumab (Omnitarg®, Perjeta®; Genentech). In contrast to trastuzumab, this antibody was not developed to reduce the membrane expression levels of HER2, but to interfere with HER2 homo- and heterodimer formation by binding to and occluding the dimerization domain II of the receptor. Pertuzumab treatment has an unexpected low therapeutic efficacy in vitro and in vivo as single agent; nevertheless, its combination with trastuzumab shows synergistic effects. Therefore, the combination of both antibodies may become a standard of care therapy for breast cancer patients (Capelan M., et al., Ann. Oncol., 24, 273-82, 2013).

The preclinical and clinical success of the combination of trastuzumab and pertuzumab has led to the concept that dual targeting of domains II and IV in HER2 is required for superior anti-tumor efficacy. This is aligned with other molecules more recently generated to simultaneously target HER2 on domains II and IV. For instance, the Danish company Symphogen is developing antibody mixes against domains II and IV of HER2 that have shown some higher efficacy (i.e. superior to trastuzumab alone) in preclinical mouse tumor models.

Similarly, US2011/033460 describes that the combination of antibodies that bind domain I and domain IV of HER2 exhibits synergistic effects on DNA synthesis and viability of BT474 cells. Furthermore, US2011/033460 also describes bispecific antibodies that bind two different epitopes of HER2, one epitope located on domain I of HER2 and the other epitope located on domain IV of HER2.

WO 2009/068625 covers the development of biparatopic antibody constructs comprising a first antibody domain, which competes with trastuzumab for binding to HER2, and a second antibody domain, which binds to a different epitope or part of HER2. Interestingly, some constructs had an antagonistic effect of SKBR3 cell proliferation, whereas others had an agonistic effect. Especially, WO 2009/068625 covers the development of biparatopic antibody constructs comprising a first antibody domain, which competes with trastuzumab for binding to HER2 (i.e. binding domain IV of Her2) and a second antibody domain, which competes with pertuzumab for binding to HER2 (i.e. binding domain II of HER2). Constructs where the domain IV binding antibody domain was cloned N-terminally to the domain II binding antibody domain showed blocking of map kinase activation, whereas such a blocking was not observed with the other orientation (i.e., having the domain II binding antibody domain at the N-terminus). Overall, WO 2009/068625 describes a variety of biparatopic antibody constructs targeting HER2, which have to variable extends effects on SKBR3 cell proliferation (agonistic or antagonistic) or cell signaling, but no cytotoxic nor apoptotic effects were described.

Bivalent binding proteins, such as bivalent diabody molecules or bivalent affibodies targeting HER2, are described also (Nielsen, U. B., et al., Cancer Res., 60, 6434-6440, 2000; Steffen, A-C., Cancer Biother. Radiopharmaceut. 20, 239-248, 2005). Such molecules combine two times the same binding domain and thus are different to biparatopic molecules that comprise two binding domains each of which binds to a different epitope on the same target molecule.

As an alternative to antibody-derived therapeutics and SMIs, there are novel binding proteins or binding domains that can be used to specifically bind a target molecule (e.g. Binz, H. K., Amstutz, P. and Plückthun, A., Nat. Biotechnol. 23, 1257-1268, 2005) and thereby act as an antagonist. One such novel class of binding proteins or binding domains not possessing an Fc are based on designed repeat proteins or designed repeat domains (WO 2002/020565; Binz, H. K., Amstutz, P., Kohl, A., Stumpp, M. T., Briand, C., Forrer, P., Grütter, M. G., and Plückthun, A., Nat. Biotechnol. 22, 575-582, 2004; Stumpp, M. T., Binz, H. K and Amstutz, P., Drug Discov. Today 13, 695-701, 2008).

WO 2002/020565 describes how large libraries of repeat proteins can be constructed and their general application. Such designed repeat domains harness the modular nature of repeat proteins and may possess N-terminal and C-terminal capping modules to prevent the designed repeat domains from aggregation by shielding the hydrophobic core of the domain (Forrer, P., Stumpp, M. T., Binz, H. K. and Plückthun, A., FEBS letters 539, 2-6, 2003). This novel class of binding proteins includes designed ankyrin repeat proteins (DARPins). The generation of monospecific DARPins binding to HER2 were previously described (e.g. Steiner, D., Forrer, P. and Plückthun, A., J. Mol. Biol. 382, 1211-1227, 2008; Zahnd, C., Pecorari, F., Straumann, N., Wyler, E. and Plückthun, A., J. Biol. Chem. 281(46), 35167-35175, 2006).

Recently, a bispecific designed ankyrin repeat protein was described, which targets HER2 (Jost, Ch., et al., Structure 21, 1-13, 2013). The authors show that binding of two ankyrin repeat domains connected by a short linker (longer linkers do not work as well), one targeting domain I of Her2 and the other domain IV of Her2, causes stronger cytotoxic effects on BT474 cells as compared to trastuzumab alone, which targets domain IV of Her2. This biparatopic repeat protein works by intra-molecular cross-linking of two Her2 molecules; i.e., it connects two membrane-bound HER2 molecules, distorting them such that they cannot form signaling-competent dimers with any EGFR family member, preventing any kinase dimerization, and thus leading to the observed cytotoxic effects.

Even though the prior art indicates that targeting of HER2 is beneficial for the therapy of diseases, such as cancer, there is a clear need to generate binding proteins targeting HER2 with higher efficacy.

Object of the Present Invention

It is an object of the present invention to provide new antagonists to Her2.

It is another object of the present invention to provide a new mechanism of inhibiting HER2-related cell signaling.

It is another object of the present invention to provide a novel approach to inhibit HER2-mediated cell proliferation and/or to induce apoptosis in a cell (e.g. tumor cell), tissue, organ or patient.

It is another object of the present invention to provide a monotherapeutic approach that addresses two domains of Her2 by using biparatopic repeat proteins.

It is another object of the present invention to provide new therapeutic options for cancer.

It is another object of the present invention to provide a treatment against a neoplastic disease, which has good efficacy and/or little side effects.

It is another object of the present invention to provide an alternative treatment against neoplastic diseases which do not (or only partially) respond, or are resistant, to, therapies from the prior art.

SUMMARY OF THE INVENTION

These objects are achieved by the subject matter of the independent claims, while the dependent claims as well as the specification disclose further preferred embodiments.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

BRIEF DESCRIPTION OF THE FIGURES

The binding of monovalent DARPins to the HER2 extra cellular domain (domain I-IV) was tested by competition ELISA using purified HER2 domains (domain I, domain III-IV or domain I-III) as competitors, as depicted in FIGS. 1A and 1B. In presence of 500 nM of Her2 domain I, the DARPin #51 and DARPin #52 cannot bind HER2 (domain I-IV) anymore, indicating that they bind an epitope located on domain I. DARPin #7, DARPin #53 and DARPin #54 are binding domain II as neither 500 nM of Her2 domain I nor 500 nM of Her2 domain III-IV can prevent their binding to the full length Her2 (domain I-IV).

FIG. 2. Inhibition of BT474 Cell Proliferation by Monovalent and Biparatopic Binding Proteins The inhibition of BT474 proliferation by monovalent DARPins (i.e. DARPin in #1 and DARPin #18), a non-covalent mixture of these monovalent DARPins and biparatopic binding proteins comprising these monovalent DARPins in different orientations (DARPin #41 and DARPin #49) was tested.

FIG. 3. Inhibition of BT474 cell proliferation by various biparatopic DARPins Inhibition of BT474 proliferation by a subset of biparatopic DARPins (#23, #24, #33, #37, #43, #44 and #41) comprising different N-terminal and/or C-terminal ankyrin repeat domains is shown. The inhibition of proliferation by various concentrations of DARPins and the corresponding fitted inhibition curves are shown for a distinct single experiment each. The IC50 values for distinct DARPins are listed in Table 2. FIG. 3D shows inhibition of biparatopic DARPins having DARPin #51 at the N-terminus and SEQ ID NO:82 at the C-terminus. Graph show OD, optical density at 450 nm minus OD at 620 nm plotted against C, concentration of DARPins in nM. The X axis is shown in logarithmic scale. See below for the definitions of the DARPins. #23, DARPin #23; #24, DARPin #24; #33, DARPin #33; #37, DARPin #37; #41, DARPin #41; #43, DARPin #43; #44, DARPin #44. DARPin #23 is SEQ ID NO:84 with a His-tag (SEQ ID NO:6) fused to its N-terminus. DARPin #24 is SEQ ID NO:85 with a His-tag (SEQ ID NO:6) fused to its N-terminus. DARPin #33 is SEQ ID NO:94 with a His-tag (SEQ ID NO:6) fused to its N-terminus. DARPin #37 is SEQ ID NO:98 with a His-tag (SEQ ID NO:6) fused to its N-terminus. DARPin #41 is SEQ ID NO:102 with a His-tag (SEQ ID NO:6) fused to its N-terminus. DARPin #43 is SEQ ID NO:104 with a His-tag (SEQ ID NO:6) fused to its N-terminus. DARPin #44 is SEQ ID NO:105 with a His-tag (SEQ ID NO:6) fused to its N-terminus. DARPin #51 is SEQ ID NO:112 with a His-tag (SEQ ID NO:6) fused to its N-terminus.

FIG. 6. Comparison of efficacy of DARPin #41 with benchmarks in inhibition of cell proliferation and induction of apoptosis.

Inhibition of proliferation (FIG. 6A) and induction of apoptosis (FIG. 6B) in BT474 cells was tested for DARPin #41 and the benchmarks trastuzumab and pertuzumab and a combination of 100 nM trastuzumab and a titration of pertuzumab.

FIG. 7. Inhibition of BT474 Cell Proliferation by Different Formats of Biparatopic Binding Proteins The inhibition of BT474 proliferation by different formats of biparatopic DARPins composed of DARPin #1 at the N-terminus and SEQ ID NO:79 at the C-terminus is shown.

DETAILED DESCRIPTION OF THE INVENTION

According to one embodiment of the invention, a recombinant binding protein comprising at least a first and a second repeat domain, wherein each of said two repeat domains binds the extracellular region of HER2 and wherein said repeat domains are covalently linked.

Figure 6A:
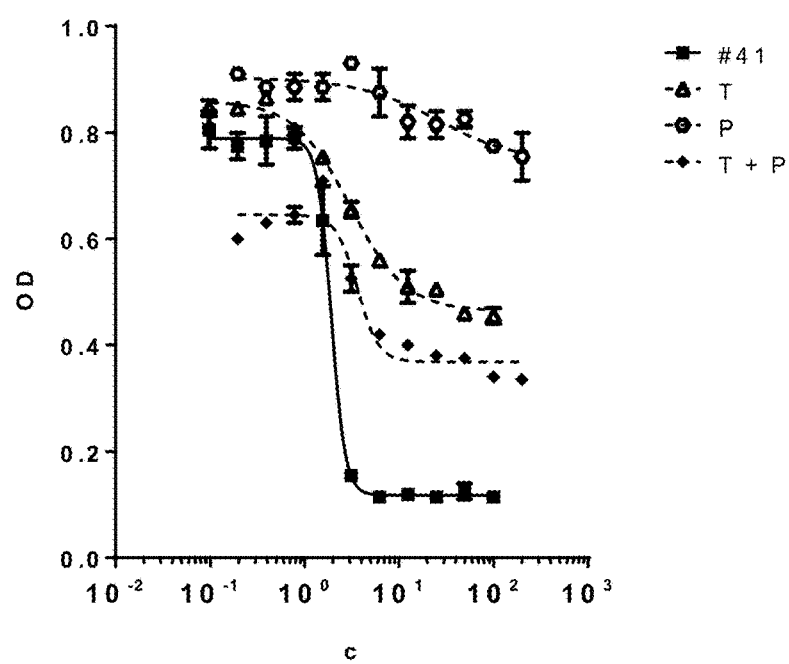
FIG. 6A shows inhibition of proliferation by various concentrations of DARPin, respectively benchmark concentrations and the corresponding fitted inhibition curves are shown for a distinct single experiment each. The IC50 values for distinct cell lines are listed in Table 3. The Graph shows OD, optical density at at 450 nm minus OD at 620 nm plotted against C, concentration of DARPin/benchmarks in nM. The X axis is shown in logarithmic scale.
Figure 6B:
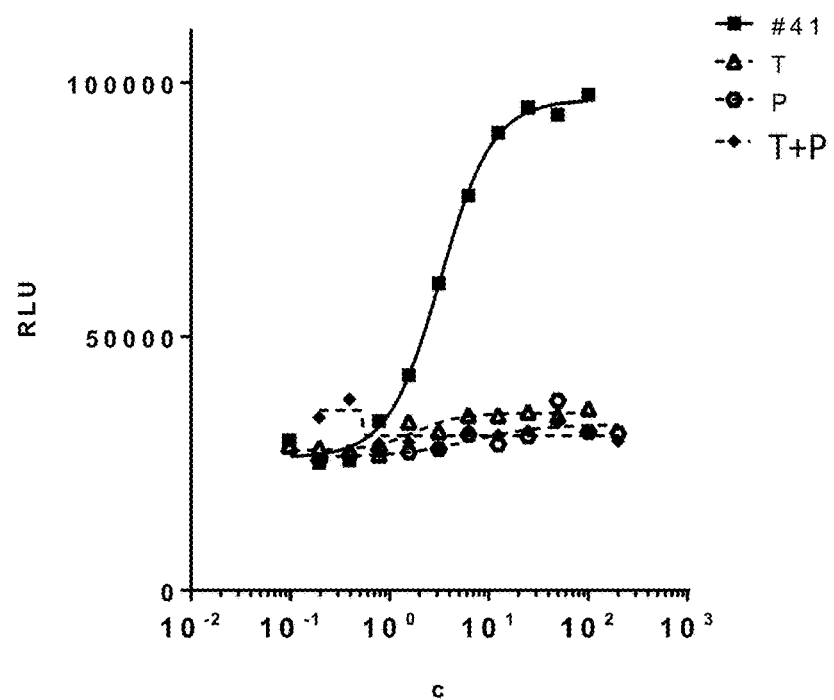
FIG. 6B shows induction of apoptosis by various concentrations of DARPin, respectively benchmark concentrations and the corresponding fitted activation curves are shown for a distinct single experiment each. The EC50 values for distinct cell lines are listed in Table 3. The Graph shows relative light units (RLU) plotted against C, concentration of DARPin/ benchmarks in nM. The X axis is shown in logarithmic scale. See below for the definitions of DARPins. T, trastuzumab; P, pertuzumab; #41, DARPin #41. DARPin #41 is SEQ ID NO:102 with a His-tag (SEQ ID NO:6) fused to its N-terminus.

It has surprisingly turned out that binding of the extracellular part of HER2 with a recombinant binding protein comprising at least two covalently linked repeat domains, each with specificity for the extracellular region of HER2, has advantageous and unexpected effects over prior art approaches as outlined above, which bind HER2 with distinct and individual binders (e.g., a combination of trastuzumab and pertuzumab; FIG. 6).

Human HER2 consists of 1255 amino acids with a 21 amino acid signal sequence, a 631 amino acid extracellular region (e.g. the ectodomain comprising domains I to IV), a 23 amino acid transmembrane region, and a 580 amino acid cytoplasmic domain.

Preferably, said binding of the extracellular region of HER2 by said recombinant binding protein is a simultaneous or concurrent binding of said repeat domains to said extracellular region of HER2. Also preferably, said repeat domains bind to two different epitopes of the extracellular region of HER2. Also preferably, said repeat domains bind to two different and non-overlapping epitopes of the extracellular region of HER2.

One reason for this increased efficacy could be that a recombinant binding protein according to the invention induces a so far not described tethered conformation of the extracellular region of HER2, which seems to be the consequence of an intramolecular interaction of the biparatopic binding protein of the invention with two different epitopes on the extracellular region of HER2 (Example 8); i.e. both repeat domains of the binding protein seem to bind simultaneously to different epitopes on the same HER2 molecule and thereby forcing the extracellular region of HER2 in this new tethered conformation. Such a tethered conformation is not described by the prior art. Importantly, these two repeat domains need to be linked by being present in the same binding protein; i.e. a simple mixture of the two repeat domains does not show efficacy (FIG. 2B). Furthermore, the bivalent binding of such a binding protein to the extracellular region of HER2 could develop synergistic binding effects by exhibiting increased avidity, i.e., a combined strength of synchronous binding to different epitopes of the target. Avidity is distinct from affinity, which corresponds to the strength of a single binding interaction. Overall, this specific interaction of the binding protein with HER2 may explain the very effective inhibition of proliferation and induction of apoptosis by such molecules as shown in the examples.

According to this theory the two different repeat domains in the same protein synergistically support each other in binding their respective epitope, thus leading to an increase in overall affinity to the target.

Binding of the first repeat domain to its epitope on HER2 brings the second repeat domain into an energetically and/or sterically favorable position which facilitates it's binding to its respective epitope on HER2.

As shown in the examples the covalent linkage of the first and the second repeat domain seems to potentiate their biological activity.

In a preferred embodiment of the recombinant binding protein according to the invention a first repeat domain binds domain II of HER2 and a second repeat domain binds domain IV of HER2.

It is important to understand that the term "binds domain II" means that the respective repeat domain binds primarily domain II of HER2. This definition, however, does not exclude that the parts of said repeat domain can bind, or overlap, to other domains. The same applies for the term "binds domain IV".

Figure 3A:
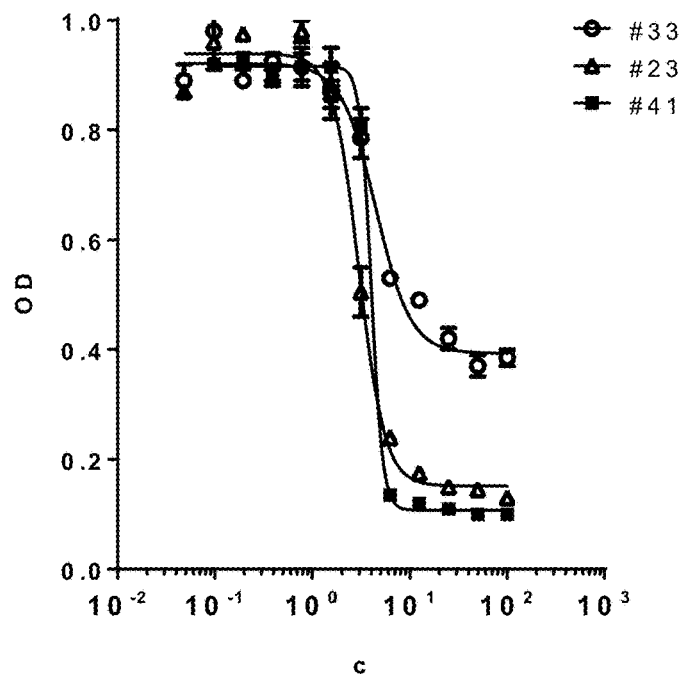
FIG. 3A shows inhibition of biparatopic DARPins having SEQ ID NO:76 at the C-terminus
Figure 3B:
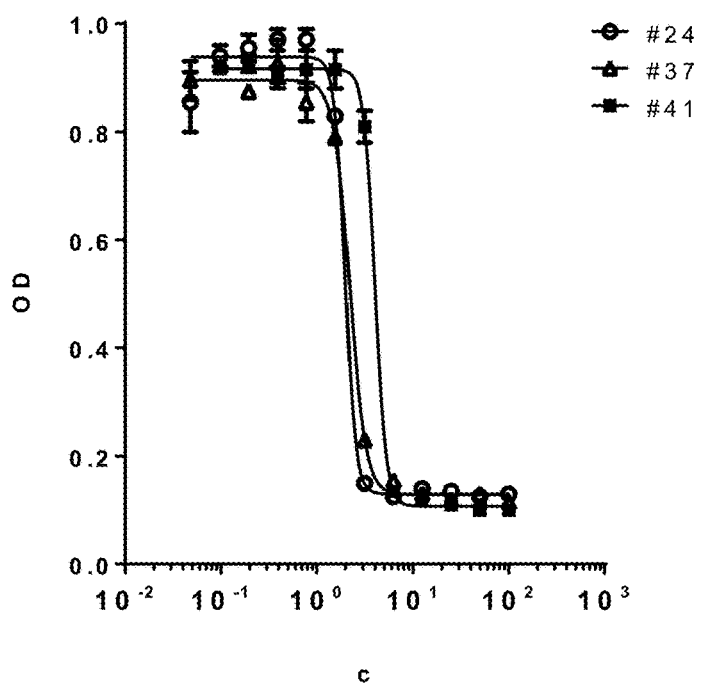
FIG. 3B shows inhibition of biparatopic DARPins having SEQ ID NO:79 at the C-terminus.
Figure 3C:
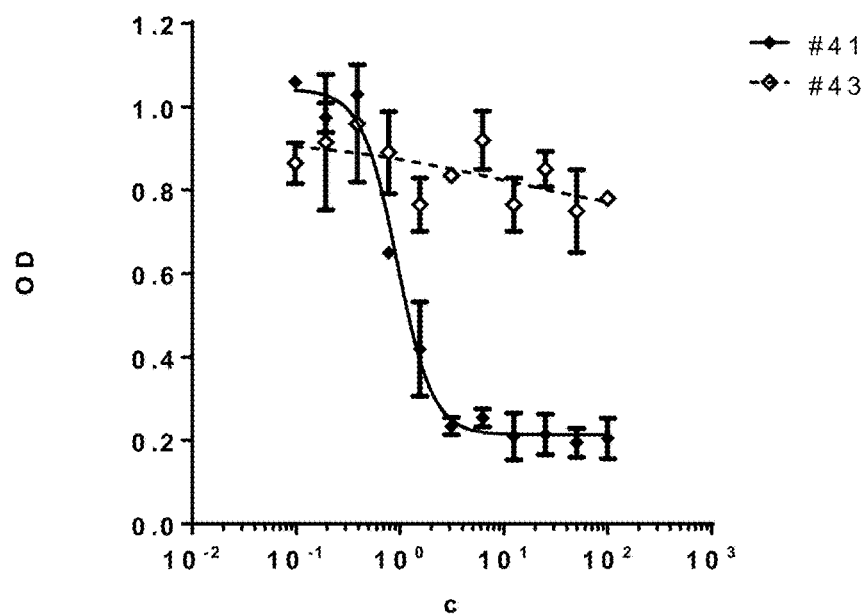
FIGS. 3C and 3D show inhibition of biparatopic DARPins having DARPin #51 at the N-terminus and SEQ ID NO:79 at the C-terminus
Figure 3D:
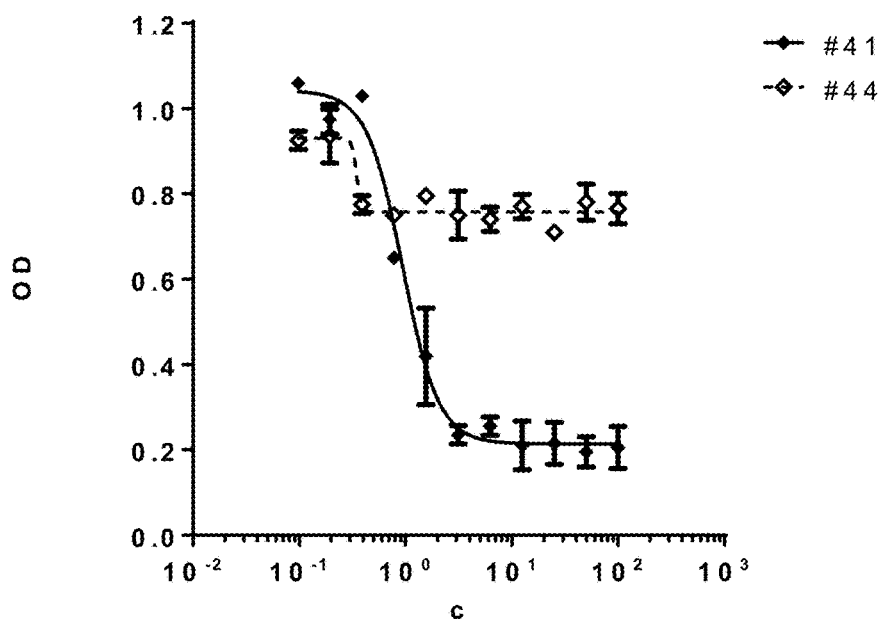
Figure 4A:
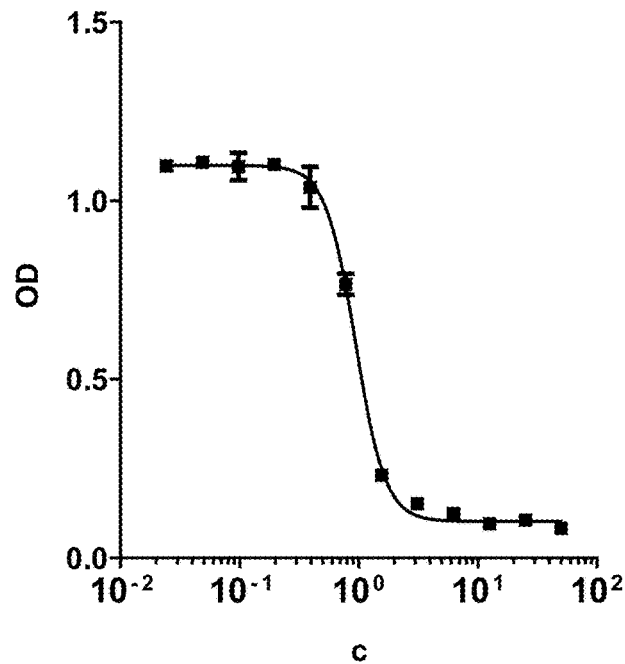
FIG. 4. Inhibition of cell proliferation by biparatopic DARPin #41 in different cell lines Inhibition of proliferation of NCI-N87 (FIG. 4A) and ZR75-30 (FIG. 4B) and MDA-MB175 (FIG. 4C) by DARPin #41 and trastuzumab was tested. The inhibition of proliferation by various concentrations of DARPins and the corresponding fitted inhibition curves are shown for a distinct single experiment each. The IC50 values for distinct cell lines are listed in Table 3. Graph shows OD, optical density at 450 nm minus OD at 620 nm plotted against C, concentration of DARPins in nM. The X axis is shown in logarithmic scale. See below for the definitions of the DARPins and reference molecules. #41, DARPin #41; T, trastuzumab. DARPin #41 is SEQ ID NO:102 with a His-tag (SEQ ID NO:6) fused to its N-terminus.
Figure 4B:
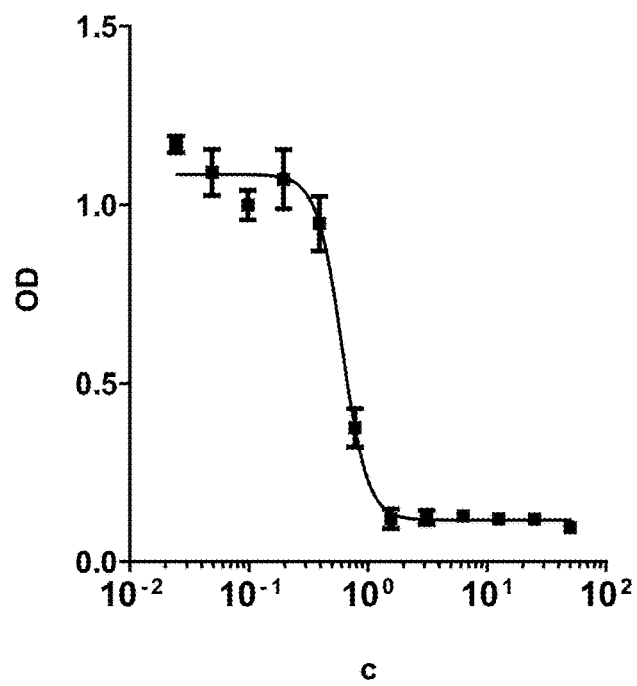
Figure 4C:
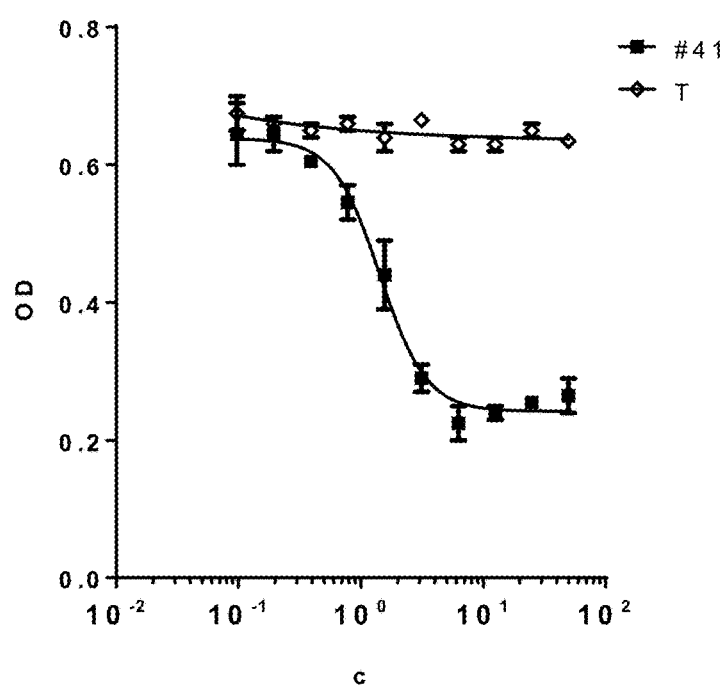
Figure 5A:
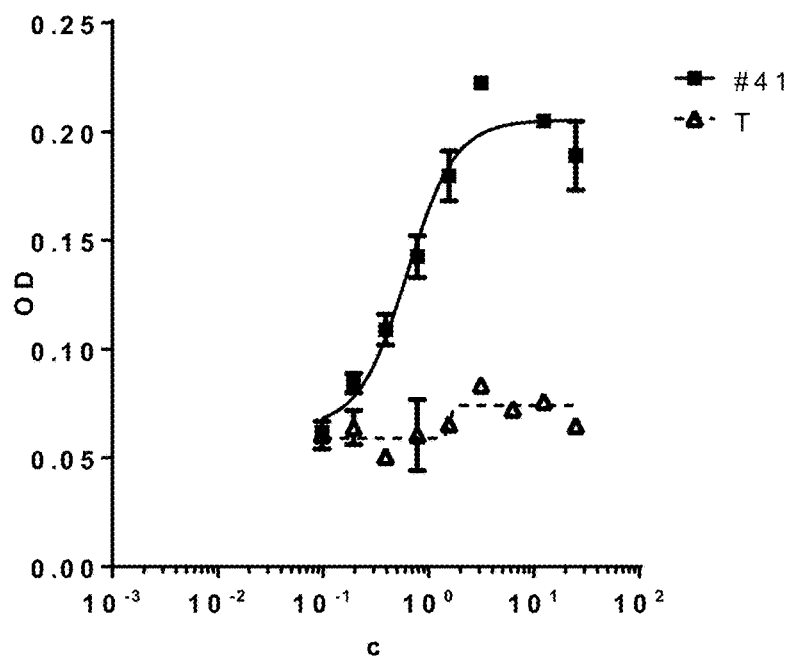
FIG. 5. Induction of apoptosis by biparatopic DARPin #41 in different cell lines Induction of apoptosis in BT474 cells (FIG. 5A) and NCI-N87 cells (FIG. 5B) and MDA-MB175 (FIG. 5C) by DARPin #41 and trastuzumab was tested. The induction of apoptosis by various concentrations of DARPins and the corresponding fitted inhibition curves are shown for a distinct single experiment each. The EC50 values for distinct cell lines are listed in Table 3. Graph in FIG. 5A shows OD, optical density at 450 nm minus OD at 490 nm plotted against C, concentration of DARPins or trastuzumab in nM. Graph in FIGS. 5B and 5C shows RLU, relative light units plotted against C, concentration of DARPins or trastuzumab in nM. The X axis is shown in logarithmic scale. See below for the definitions of DARPins. T, trastuzumab; #41, DARPin #41. DARPin #41 is SEQ ID NO:102 with a His-tag (SEQ ID NO:6) fused to its N-terminus.
Figure 5B:
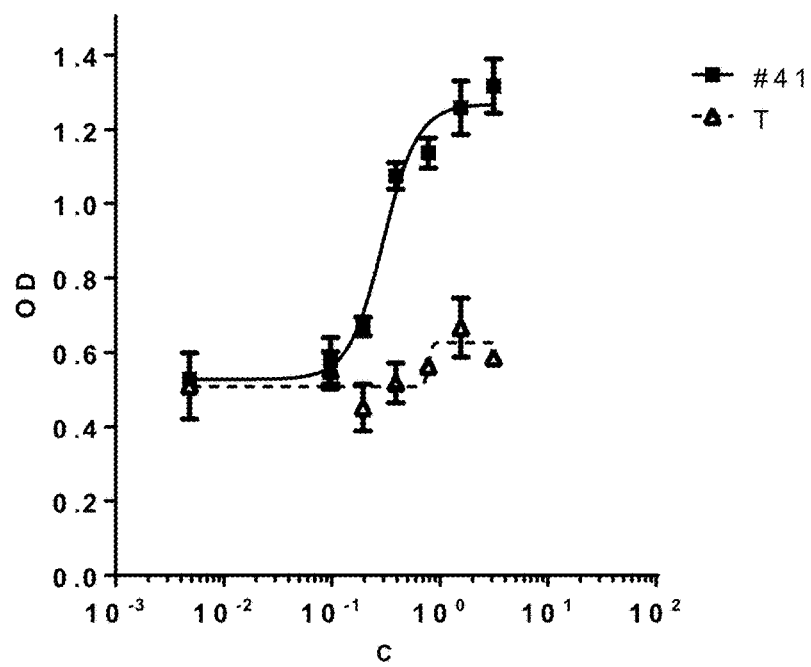
Figure 5C:
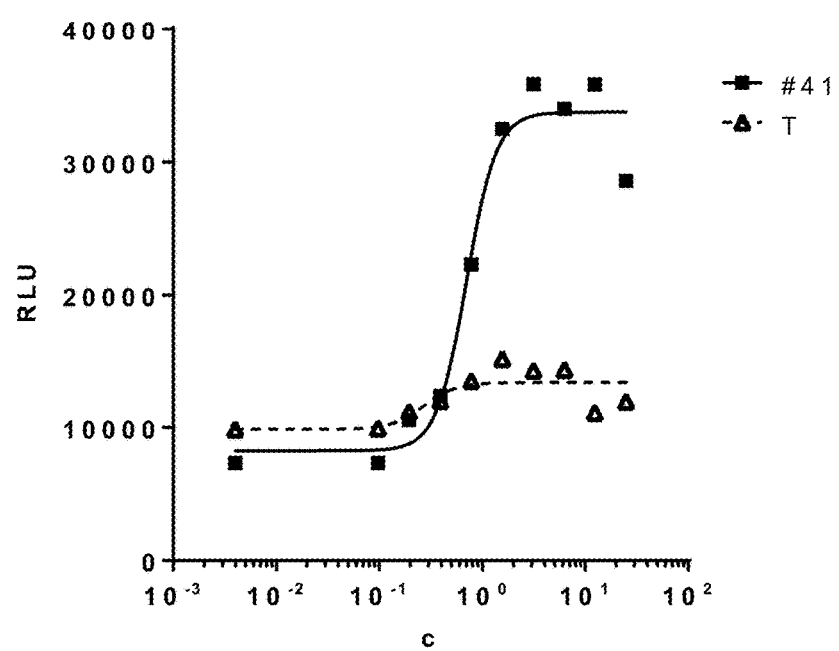

A simultaneous targeting of domains II and IV of HER2 by a biparatopic binding protein according to the present invention has particular unexpected effects over what was known from the prior art. Cell responses in terms of inhibition of proliferation and induction of cell apoptosis by such binding proteins were much more dramatic when compared to effects obtained by state of the art antibodies. For example, the extent of such responses has proved to be superior to that induced by clinical antibody benchmarks, such as the combination of trastuzumab and pertuzumab targeting domain IV and II of HER2, respectively (FIGS. 4, 5 and 6). Interestingly, some biparatopic binding proteins binding to domain I and domain IV of HER2 do not show such unexpected effects (FIGS. 3C and 3D).

Methods to determine the domain of the extracellular region of HER2 to which a repeat domain binds, e.g. as shown in Example 3, are well known to the person skilled in the art (e.g. Jost et al., loc. cit.).

Applicant's findings have important implications for the treatment of HER2-driven human cancers, in the sense that simultaneous targeting of domains II and IV of HER2 with a biparatopic binding protein according to the present invention could be a more efficacious alternative to current antibody targeting approaches.

The binding protein according to the present invention is thus preferably a biparatopic binding protein, i.e., it comprises two antigen repeat domains recognizing two different epitopes, or domains (e.g. domains II and IV) on the same protein target (namely HER2). However, polypeptides which are multiparatopic, i.e, containing antigen repeat domains recognizing three, four or more epitopes on the same target protein, are encompassed within the scope invention, as are polypeptides which are both bi- or multi-paratopic and multivalent, i.e., having also antigen repeat domains recognizing one or more other target proteins.

HER2, as used herein, relates to Human Epidermal Growth Factor Receptor 2, also known as Neu, ErbB-2, CD340 (cluster of differentiation 340) or p185. HER2 is a member of the epidermal growth factor receptor (EGFR/ErbB) family. HER2 is, in humans, encoded by ERBB2, a known proto-oncogene located at the long arm of human chromosome 17 (17q12). HER2 has the UniProtKB/Swiss-Prot number P04626.

According to a preferred embodiment of the invention, the first and second repeat domains are located on the same polypeptide, while the repeat domain targeting domain II of HER2 is located N-terminally to the repeat domain targeting domain IV of HER2.

Figure 2A:
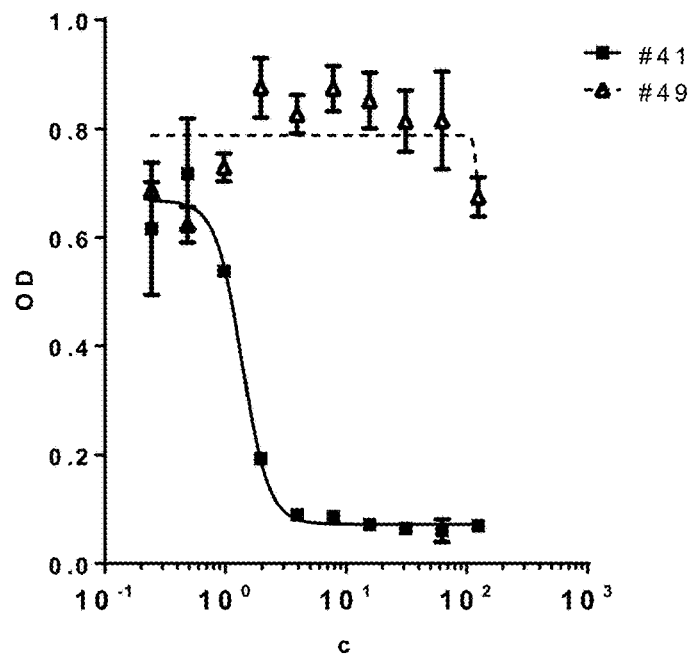
FIG. 2A shows the inhibition of proliferation by various concentrations of biparatopic DARPins and the corresponding fitted inhibition curves are shown for a distinct single experiment. The IC50 value for DARPin #41 was then calculated to be about 2 nM. The IC50 values for distinct DARPins are listed in Table 2. The graph in FIG. 2A shows OD, optical density at 450 nm minus OD at 620 nm plotted against C, concentration of DARPins in nM. The X axis is shown in logarithmic scale.
Figure 2B:
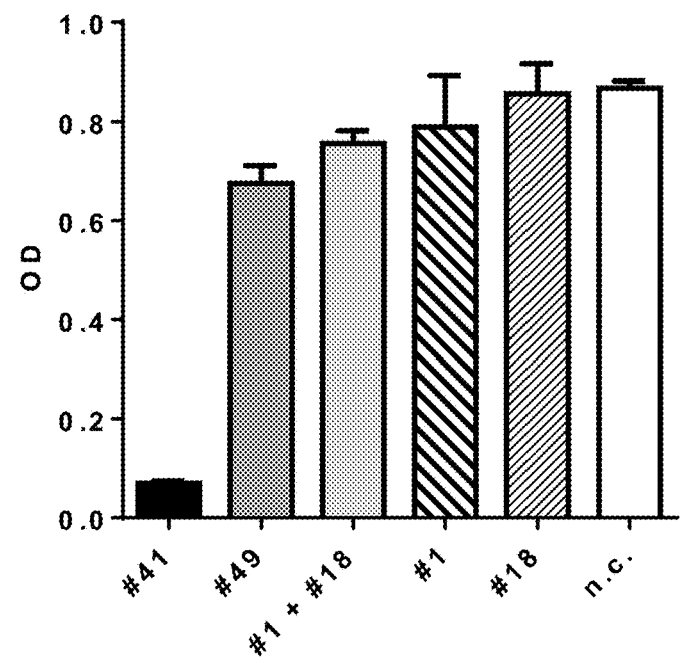
FIG. 2B shows inhibition of proliferation at a concentration of 100 nM for biparatopic DARPins, a mixture of both monovalent DARPins and the individual corresponding monovalent DARPins. The OD is plotted on the Y-axis. Inhibition of proliferation is reflected by a low OD. See below for the definitions of the DARPins. #41, DARPin #41; #49, DARPin #49; #18, DARPin #18; #1, DARPin #1; n.c., negative control. DARPin #1 is SEQ ID NO:62 with a His-tag (SEQ ID NO:6) fused to its N-terminus. DARPin #18 is SEQ ID NO:79 with a His-tag (SEQ ID NO:6) fused to its N-terminus. DARPin #41 is SEQ ID NO:102 with a His-tag (SEQ ID NO:6) fused to its N-terminus. DARPin #49 is SEQ ID NO:110 with a His-tag (SEQ ID NO:6) fused to its N-terminus. The negative control is DARPin #50, which is SEQ ID NO:111 with a His-tag (SEQ ID NO:6) fused to its N-terminus.

These embodiments are for example shown in FIG. 2A, and the corresponding description. The inventors have, surprisingly, shown that a binding protein in which the repeat domain targeting domain II of HER2 is located C-terminally to the repeat domain targeting domain IV of HER2 is significantly less efficacious than a binding protein in which the repeat domain targeting domain II of HER2 is located N-terminally to the repeat domain targeting domain IV of HER2.

Figure 1A:
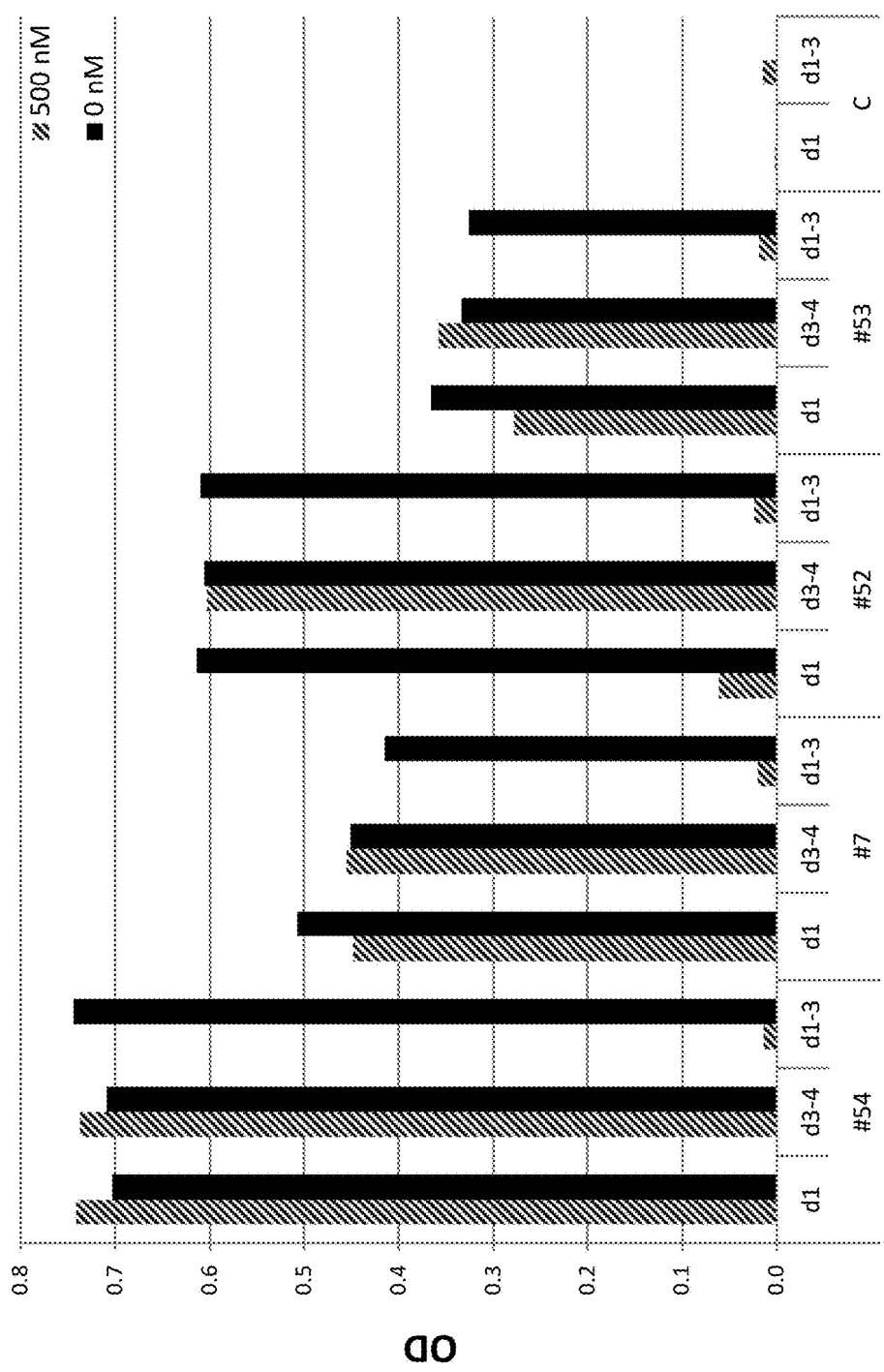
FIG. 1. Binding of DARPin domains to HER2
FIG. 1C shows that the monovalent DARPins can bind on the preformed HER2-pertuzumab complex and are thus binding a different epitope than pertuzumab on the HER2 domain II. See below for the definitions of the DARPins. OD, optical density at 450 nM minus OD at 620 nm; C, a control DARPin, which is not binding HER2; d1, domain I of HER2; d1-3 domain I-III of HER2; d3-4, domain III-IV of HER2. DARPin #7 is SEQ ID NO:68 with a His-tag (SEQ ID NO:6) fused to its N-terminus. DARPin #51 is SEQ ID NO:112 with a His-tag (SEQ ID NO:6) fused to its N-terminus. DARPin #52 is SEQ ID NO:113 with a His-tag (SEQ ID NO:6) fused to its N-terminus. DARPin #53 is SEQ ID NO:114 with a His-tag (SEQ ID NO:6) fused to its N-terminus. DARPin #54 is SEQ ID NO:115 with a His-tag (SEQ ID NO:6) fused to its N-terminus. C, the control DARPin, is DARPin #50, which is SEQ ID NO:111 with a His-tag (SEQ ID NO:6) fused to its N-terminus.
Figure 1B:
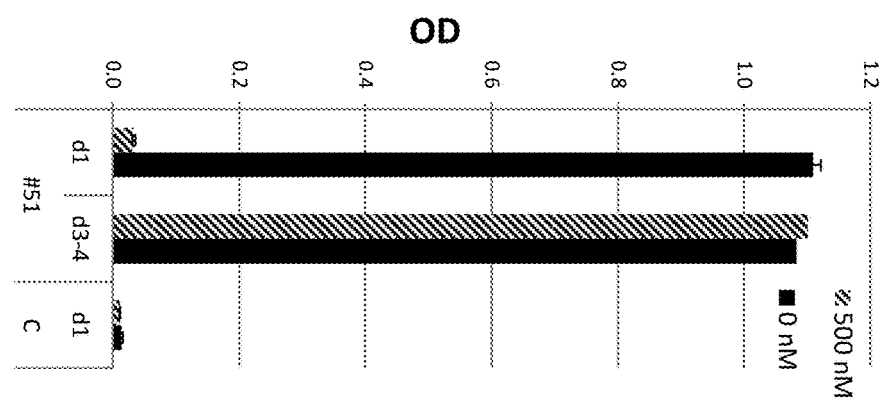
Figure 1C:
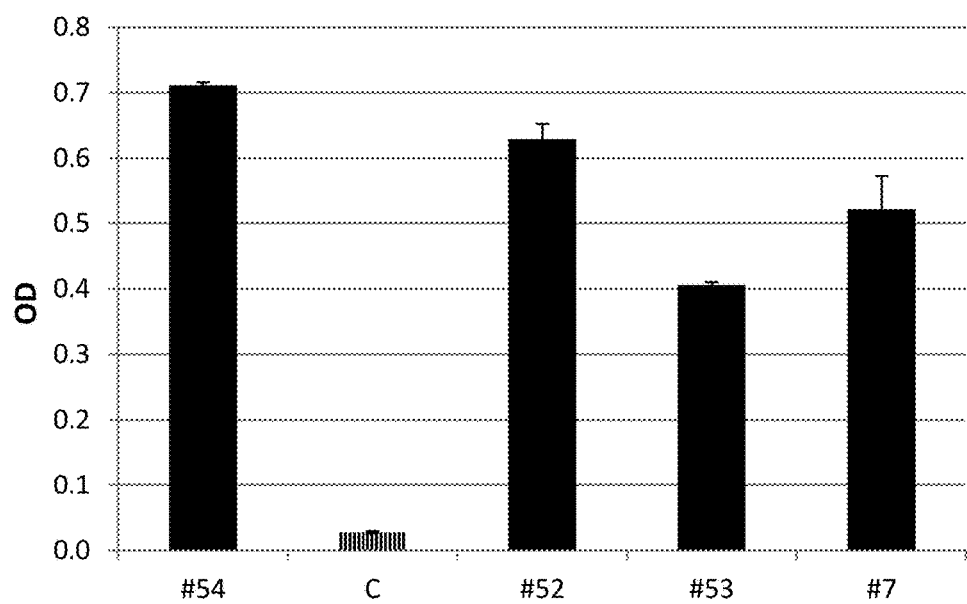

Preferably, said first repeat domain binding domain II of HER2 is not competing for binding to HER2 with pertuzumab. For example, FIG. 1C shows such repeat domains not competing for binding to HER2 with pertuzumab. Likewise preferably, said second repeat domain binding domain IV of HER2 is not competing for binding to HER2 with trastuzumab. For example, the repeat domains of DARPins #18 to 20 do not compete for binding to HER2 with trastuzumab. Methods to determine if a repeat domain does not compete for binding to HER2 with trastuzumab or pertuzumab, e.g. as shown in Example 3, are well known to the person skilled in the art.

This means that, in the first preferred embodiment, the first repeat domain binds a different epitope of domain II of HER2 than pertuzumab. Likewise, in the second preferred embodiment, the second repeat domain binds a different epitope of domain IV of HER2 than trastuzumab. Without being bound to theory, the inventors attribute at least some of the effects shown in the experimental section to these facts.

According to another preferred embodiment of the invention said first repeat domain is an ankyrin repeat domain, or a designed ankyrin repeat domain, and said second repeat domain is an ankyrin repeat domain, or a designed ankyrin repeat domain.

Preferably, said ankyrin repeat domains or designed ankyrin repeat domains comprise between 70 and 300 amino acids, in particular between 90 and 200 amino acids.

Also preferably, a repeat domain of the invention is an ankyrin repeat domain or a designed ankyrin repeat domain as described in WO 2002/020565. Examples of designed ankyrin repeat domains with biparatopic binding specificity for different domains of Her2 are shown in the Examples.

According to a preferred embodiment of the invention, the first repeat domain binds the extracellular region of HER2 in PBS with a Kd smaller than $10^{-7}$M and said second repeat domain binds the extracellular region of HER2 in PBS with a Kd smaller than $10^{-7}$M.

Kd is the dissociation constant and will further be defined in the text below. A Kd smaller than $10^{-7}$M is required to provide sufficient affinity of the repeat domain to its target. Preferably, the repeat domains bind their target domains in PBS with a Kd smaller than $10_{-8}$M, $10^{-9}$M, $10^{-10}$M, or, most preferably smaller than $10^{-11}$M.

Recombinant binding proteins comprising proteins binding domain II and/or domain IV of Her2 with a Kd in PBS below $10^{-7}$M are shown in Example 2.

According to a preferred embodiment, said binding protein inhibits stimulated proliferation of BT474 cells with an half maximal inhibitory concentration (1050) value of smaller than 100 nM. Preferably, said binding protein inhibits stimulated proliferation of BT474 cells with an 1050 value of smaller than 90, 80, 70, 60, 50, 40, 30, 20 or 10 nM. Also preferably, said binding protein inhibits stimulated proliferation of BT474 cells by at least 100%, 90%, 80%, 70%, 60%, 50%, 40%, 30%, 20% or 10%.

BT474 cells can be used to measure the functional capability of the binding proteins of the invention to inhibit proliferation by standard means well known to the person skilled in the art, e.g. as shown in Example 4. Preferably, BT474, SKBR-3, NCI-N87, ZR75-30, HCC1419 or MDA-MB175 cells can be used to measure the functional capability of the compounds of the invention to inhibit proliferation, e.g. as shown in Example 5.

Recombinant binding proteins which inhibit stimulated proliferation of BT474 cells with an 1050 value of smaller than 100 nM are disclosed, and discussed, in Example 4.

According to another preferred embodiment, said binding protein induces apoptosis in BT474 cells with an half maximal effective concentration (EC50) value of smaller than 100 nM. Preferably, said binding protein induces apoptosis in BT474 cells with an EC50 value of smaller than 90, 80, 70, 60, 50, 40, 30, 20 or 10 nM.

BT474 cells can be used to measure the functional capability of the binding proteins of the invention to induce apoptosis by standard means well known to the person skilled in the art, e.g. as shown in Example 5. Preferably, BT474, SKBR-3, NCI-N87, ZR75-30, HCC1419 or MDA-MB175 cells can be used to measure the functional capability of the compounds of the invention to induce apoptosis, e.g. as shown in Example 5.

Recombinant binding proteins which induce apoptosis in BT474 cells with an EC50 value of smaller than 100 nM are disclosed, and discussed, in Examples 5.

According to a preferred embodiment, said first and second repeat domains are connected by a polypeptide linker.

Such polypeptide linker may, for example, be accomplished by mere genetic fusion of the encoding cDNAs of the respective domains to be fused. Such type of embodiment qualifies as a fusion peptide protein with two different repeat domains.

The linker can for example consist of an oligopeptide comprising the amino acids G and S, or P and T, respectively, as set forth in SEQ ID Nos: 7 to 12. According to another preferred embodiment, a "multimerization moiety" as described below can be used. Alternatively, the two repeat domains can be linked to one another, e.g., by means of non-peptide based chemical linkers.

Preferably, the recombinant binding protein and/or repeat domain has a midpoint denaturation temperature (Tm) above 45° C., more preferably above 50° C., more preferably above 55° C., and most preferably above 60° C. upon thermal unfolding in PBS at pH 7.4. A binding protein or a repeat domain of the invention possesses a defined secondary and tertiary structure under physiological conditions. Thermal unfolding of such a polypeptide results in a loss of its tertiary and secondary structure, which can be followed, for example, by circular dichroism (CD) measurements. The midpoint denaturation temperature of a binding protein or repeat domain upon thermal unfolding corresponds to the temperature at the midpoint of the cooperative transition in physiological buffer upon heat denaturation of said protein or domain by slowly increasing the temperature from 10° C. to about 100° C. The determination of a midpoint denaturation temperature upon thermal unfolding is well known to the person skilled in the art. This midpoint denaturation temperature of a binding protein or repeat domain upon thermal unfolding is indicative of the thermal stability of said polypeptide.

Also preferred is a recombinant binding protein and/or ankyrin repeat domain forming less than 5% (w/w) insoluble aggregates at concentrations up to 20 g/L, preferably up 40 g/L, more preferably up to 60 g/L, even more preferably up to 80 g/L, and most preferably up to 100 g/L when incubated for over 5 days, preferably over 10 days, more preferably over 20 days, more preferably over 40 days, and most preferably over 100 days at 37° C. in PBS. The formation of insoluble aggregates can be detected by the appearance of visual precipitations, gel filtration or dynamic light scattering, which strongly increases upon formation of insoluble aggregates. Insoluble aggregates can be removed from a protein sample by centrifugation at 10'000×g for 10 minutes. Preferably, a recombinant binding protein and/or ankyrin repeat domain forms less than 2%, more preferably less than 1%, 0.5%, 0.2%, 0.1%, or most preferably less than 0.05% (w/w) insoluble aggregates under the mentioned incubation conditions at 37° C. in PBS. Percentages of insoluble aggregates can be determined by separation of the insoluble aggregates from soluble protein, followed by determination of the protein amounts in the soluble and insoluble fraction by standard quantification methods.

Also preferred is a recombinant binding protein and/or ankyrin repeat domain that does not lose its native three-dimensional structure upon incubation in PBS containing 100 mM dithiothreitol (DTT) for 1 or 10 hours at 37° C.

In one particular embodiment the invention relates to a recombinant binding protein comprising two ankyrin repeat domains, specifically binding to HER2 and having the indicated or preferred midpoint denaturation temperature and non-aggregating properties as defined above.

According to other preferred embodiments of the invention, it is provided that
said first repeat domain competes for binding to HER2 with an ankyrin repeat domain selected from the group consisting of SEQ ID NOs: 62 to 68, 72 and 114 to 121 and/or
said second repeat domain competes for binding to HER2 with an ankyrin repeat domain selected from the group consisting of SEQ ID NOs: 74 to 82.

The inventors have evidence that, out of these repeat domains, the first repeat domain binds domain II of HER2, whereas the second repeat domain binds domain IV of HER2

Preferably, said first repeat domain competes for binding to HER2 with an ankyrin repeat domain selected from the group consisting of SEQ ID NOs: 62 to 67 and 115 to 121. More preferably, said first repeat domain competes for binding to HER2 with an ankyrin repeat domain selected from the group consisting of SEQ ID NOs: 62, 115, 120, and 121, in particular SEQ ID NO: 115 and 120. Also preferably, said first repeat domain competes for binding to HER2 with a binding protein selected from the group of DARPins #1 to 6 and 54 to 60; more preferably, with a binding protein from the group of DARPins #1, 54, 59 and 60; in particular, with a binding protein from the group of DARPins #54 and 60.

Further preferred, said second repeat domain competes for binding to HER2 with an ankyrin repeat domain selected from the group consisting of SEQ ID NOs: 79 to 81, in particular SEQ ID NO: 80 and 81. Also preferably, said second repeat domain competes for binding to HER2 with a binding protein selected from the group of DARPins #18 to 20; in particular, with a binding protein from the group of DARPins #19 and 20.

According to still other preferred embodiments of the invention, it is provided that
a first repeat domain comprises an amino acid sequence that has at least 70% amino acid sequence identity with one ankyrin repeat domain selected from the group consisting of SEQ ID NOs: 62 to 68, 72 and 114 to 121,
a second repeat domain comprises an amino acid sequence that has at least 70% amino acid sequence identity with one ankyrin repeat domain selected from the group consisting of SEQ ID NOs: 74 to 82, and wherein further,
G at position 1 and/or S at position 2 of said ankyrin repeat domain are optionally missing; and
L at the second last position and/or N at the last position of said ankyrin repeat domain are optionally exchanged by A.

Preferably, said first repeat domain comprises an amino acid sequence that has at least 70% amino acid sequence identity with one ankyrin repeat domain selected from the group consisting of SEQ ID NOs: 62 to 67 and 115 to 121. More preferably, said first repeat domain comprises an amino acid sequence that has at least 70% amino acid sequence identity with one ankyrin repeat domain selected from the group consisting of SEQ ID NOs: 62, 115, 120, and 121, in particular SEQ ID NO: 115 and 120. Also preferably, said first repeat domain comprises an amino acid sequence that has at least 70% amino acid sequence identity with a binding protein selected from the group consisting of DARPins #1 to 6 and 54 to 60; more preferably, with a binding protein from the group of DARPins #1, 54, 59 and 60; in particular, with a binding protein from the group of DARPins #54 and 60.

Further preferred, said second repeat domain comprises an amino acid sequence that has at least 70% amino acid sequence identity with one ankyrin repeat domain selected from the group consisting of SEQ ID NOs: 79 to 81, in particular SEQ ID NO: 80 and 81. Also preferably, said second repeat domain comprises an amino acid sequence that has at least 70% amino acid sequence identity with a binding protein from the group consisting of of DARPins #18 to 20; in particular, with a binding protein from the group of DARPins #19 and 20.

Preferably, the first ankyrin repeat domain comprises an amino acid sequence that has at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% amino acid sequence identity with one ankyrin repeat domain selected from the group consisting of SEQ ID NOs: 62 to 68, 72 and 114 to 121.

Preferably, the second ankyrin repeat domain comprises an amino acid sequence that has at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% amino acid sequence identity with one ankyrin repeat domain selected from the group consisting of SEQ ID NOs: 74 to 82.

Also preferably, the first ankyrin repeat domain comprises an amino acid sequence that has at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% amino acid sequence identity with one, two or three ankyrin repeat modules present between the N-terminal and C-terminal capping modules of an ankyrin repeat domain selected from the group consisting of SEQ ID NOs: 62 to 68, 72 and 114 to 121.

Also preferably, the second ankyrin repeat domain comprises an amino acid sequence that has at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% amino acid sequence identity with one, two or three ankyrin repeat modules present between the N-terminal and C-terminal capping modules of an ankyrin repeat domain selected from the group consisting of SEQ ID NOs: 74 to 82.

According to yet other preferred embodiments of the invention, it is provided that
- said first repeat domain is selected from the group consisting of SEQ ID NOs: 62 to 68, 72 and 114 to 121,
- said second repeat domain is selected from the group consisting of SEQ ID NOs: 74 to 82
- and wherein further
- G at position 1 and/or S at position 2 of said ankyrin repeat domain are optionally missing; and
- L at the second last position and/or N at the last position of said ankyrin repeat domain are optionally exchanged by A.

Preferably, the first ankyrin repeat domain is selected from the group consisting of SEQ ID NOs: 62 to 67 and 115 to 121; more preferably, 115, 120, and 121; in particular, SEQ ID NO: 115 and 120.

Preferably, the second ankyrin repeat domain is selected from the group consisting of SEQ ID NOs: 79 to 81, in particular SEQ ID NO: 80 and 81.

According to yet other preferred embodiments of the invention, it is provided that
- said first repeat domain comprises an ankyrin repeat module having an amino acid sequence selected from the group consisting of SEQ ID NO: 15 to 18, 21 to 23, 37, 38, 125, 126, 129, 130, 133 and 134 and sequences, wherein up to 9 amino acid residues in SEQ ID NO: 15 to 18, 21 to 23, 37, 38, 125, 126, 129, 130, 133 and 134 are replaced by any other amino acid residues, and/or
- said second repeat domain comprises an ankyrin repeat module having an amino acid sequence selected from the group consisting of SEQ ID NO: 46, 47, 51, 52, 55 and 56, and sequences, wherein up to 9 amino acid residues in SEQ ID NO: 46, 47, 51, 52, 55 and 56 are replaced by any other amino acid residues.

Preferably, such an ankyrin repeat module of the first ankyrin repeat domain is selected from the group consisting of SEQ ID NO: 15 to 18, 125, 126, 129, 130, 133 and 134; more preferably, 15, 125, 129 and 133; and even more preferably, 125 and 133.

Preferably, such an ankyrin repeat module of the second ankyrin repeat domain is selected from the group consisting of SEQ ID NO: 46, 47, 55 and 56; more preferably, 55 and 56.

Also preferably, up to 8 amino acids in the repeat modules of SEQ ID NO: 15 to 18, 21 to 23, 37, 38, 46, 47, 51, 52, 55, 56, 125, 126, 129, 130, 133 and 134 are exchanged by another amino acid, more preferably up to 7 amino acids, more preferably up to 6 amino acids, more preferably up to 5 amino acids, even more preferably up to 4 amino acids, more preferably up to 3 amino acids, more preferably up to 2 amino acids, and most preferably 1 amino acid.

Preferably, when amino acids are exchanged in capping modules, repeat modules or repeat domains, repeat domains, or binding proteins, these amino acids are replaced by an amino acid selected from the group consisting of A, D, E, F, H, I, K, L, M, N, Q, R, S, T, V, W and Y; more preferably from the group consisting of A, D, E, H, I, K, L, Q, R, S, T, V, and Y. Also preferably, an amino acid is exchanged by a homologous amino acid; i.e. an amino acid is exchanged by an amino acid having a side chain with similar biophysical properties. For example, the negative charged amino acid D may be replaced by the negative charged amino acid E, or a hydrophobic amino acid such as L may be replaced by A, I or V. The techniques of exchanging an amino acid by another amino acid in a polypeptide are well known to the person skilled in the art.

Preferably, the repeat module according to the invention has an amino acid sequence selected from the group consisting of KOFQGITPLHIAATSGHLEIVEVLLKA-GAOVNA (SEQ ID NO: 16 and sequences, in which up to 9 amino acid residues in SEQ ID NO: 16 are replaced by any other amino acid residues, and wherein
- F at position 3 is optionally exchanged by A
- Q at position 4 is optionally exchanged by E;
- G at position 5 is optionally exchanged by S;
- I at position 6 is optionally exchanged by V;
- I at position 11 is optionally exchanged by L;
- T at position 14 is optionally exchanged by Q; and/or
- S at position 15 is optionally exchanged by an amino acid selected from the group consisting of N and W.

One very preferred repeat module of this group has an amino acid sequence consisting of KDFQGVTPLHIAAQS-GHLEIVEVLLKAGADVNA (SEQ ID NO: 125), SEQ ID NO: 129 or SEQ ID NO: 133.

Also preferably, the ankyrin repeat module according to the invention has an amino acid sequence selected from the group consisting of KDITGETPLHHAADSGHLEIVEV-LLKAGADVNA (SEQ ID NO: 18) and sequences, in which up to 9 amino acid residues in SEQ ID NO: 18 are replaced by any other amino acid residues, and wherein I at position 3 is optionally exchanged by V;
E at position 6 is optionally exchanged by D;
H at position 11 is optionally exchanged by L;
D at position 14 is optionally exchanged by Q;
S at position 15 is optionally exchanged by H; and/or
E at position 19 is optionally exchanged by V.

One very preferred repeat module of this group has an amino acid sequence consisting of KDVTGDTPLHLAAQHGHLEIVEVLLKAGADVNA (SEQ ID NO: 126), SEQ ID NO: 130 or SEQ ID NO: 134.

Also preferably, the ankyrin repeat module according to the invention has an amino acid sequence selected from the group consisting of KDWEGTTPLHLAAHTGHLEIVEVLLKAGADVNA (SEQ ID NO: 21) and sequences, in which up to 9 amino acid residues in SEQ ID NO: 21 are replaced by any other amino acid residues, and wherein
    W at position 3 is optionally exchanged by F;
    W at position 4 is optionally exchanged by Q;
    T at position 6 is optionally exchanged by an amino acid selected from the group consisting of I, Y and V; preferably T;
    L at position 11 is optionally exchanged by an amino acid selected from the group consisting of I and V; preferably I and V;
    H at position 14 is optionally exchanged by an amino acid selected from the group consisting of H, Q, Y and W; preferably H; and/or
    T at position 15 is optionally deleted or exchanged by an amino acid selected from the group consisting of A and D.

Also preferably, the ankyrin repeat module according to the invention has an amino acid sequence selected from the group consisting of KDTVGTTPLHYAAEDGHLEIVEVLLKAGADVNA (SEQ ID NO: 22) and sequences, in which up to 9 amino acid residues in SEQ ID NO: 22 are replaced by any other amino acid residues, and wherein
    T at position 3 is optionally exchanged by an amino acid selected from the group consisting of S, K, E and I; equal amino acid distribution;
    V at position 4 is optionally exchanged by an amino acid selected from the group consisting of Q, I and Y; preferably Y;
    T at position 6 is optionally exchanged by an amino acid selected from the group consisting of Q, F, R and W;
    Y at position 11 is optionally exchanged by an amino acid selected from the group consisting of L, E and S; preferably S;
    E at position 14 is optionally exchanged by an amino acid selected from the group consisting of S, Q, Y and V; and/or
    D at position 15 is optionally exchanged by an amino acid selected from the group consisting of S, F and Y.
    G at position 16 is optionally exchanged by D.

Also preferably, the ankyrin repeat module according to the invention has an amino acid sequence selected from the group consisting of KDVEGWTPLHYAASSGHLEIVEVLLKAGADVNA (SEQ ID NO: 38) and sequences, in which up to 9 amino acid residues in SEQ ID NO: 38 are replaced by any other amino acid residues, and wherein
    W at position 6 is optionally exchanged by Q;
    Y at position 11 is optionally exchanged by L; and/or
    S at position 15 is optionally exchanged by Y.

Also preferably, the ankyrin repeat module according to the invention has an amino acid sequence selected from the group consisting of KDWRGFTPLHYAAYLGHLEIVEVLLKAGADVNA (SEQ ID NO: 46) and sequences, in which up to 9 amino acid residues in SEQ ID NO: 46 are replaced by any other amino acid residues, and wherein
    W at position 3 is optionally exchanged by an amino acid selected from the group consisting of W, T, V and R; preferably, T and R;
    R at position 4 is optionally exchanged by an amino acid selected from the group consisting of R, T and I; preferably, I;
    F at position 6 is optionally exchanged by F or H; preferably F;
    Y at position 11 is optionally exchanged by R;
    Y at position 14 is optionally exchanged by F;
    L at position 15 is optionally exchanged by V; and/or
    H at position 17 is optionally exchanged by Q.

Preferably, 9, 8, 7, 6, 5, 4, 3, 2, or 1 amino acid residues in SEQ ID NOs:16, 18, 28, 31. 21, 22, 38 and/or 46 are replaced by any other amino acid residues.

Furthermore, it is particularly preferred that said binding protein comprises a polypeptide, wherein said polypeptide comprises said first and second ankyrin repeat domains and wherein said polypeptide has at least 70% amino acid sequence identity with a polypeptide selected from the group consisting of SEQ ID NO: 83 to 98, 102, 103, 122, 123 and 136 to 141.

Preferably, said polypeptide comprises an amino acid sequence that has at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% amino acid sequence identity with a polypeptide selected from the group consisting of SEQ ID NOs: 83 to 98, 102, 103, 122, 123 and 136 to 141.

Also preferably, such polypeptide is selected from the group consisting of SEQ ID NO: 84, 85, 86, 87, 90, 91, 92, 98, 102, 103, 122 and 123; more preferably, 85, 86, 87, 90, 91, 92, 102, 103, 122 and 123; even more preferably, 86, 87, 91 and 92; and most preferably, 86 and 87.

According to yet other preferred embodiment, one or more of the amino acid residues of the ankyrin repeat modules of said first and second ankyrin repeat domains are exchanged by an amino acid residue found at the corresponding position on alignment of an ankyrin repeat unit.

Another embodiment of the invention provides a nucleic acid molecule encoding at least one binding protein or a particular ankyrin repeat domain according to the above description. Further, a vector comprising said nucleic acid molecule is considered.

Not all binding compositions according to the present invention comprise polypeptides or proteins. The latter embodiment only relates to those who do. For these, applicant refrains from disclosing herein all nucleic acid molecules capable of encoding them because, due to the Degeneracy of the genetic code, many nucleic acid molecules can encode for one and the same polypeptide or protein.

However, it can unequivocally and unambiguously determined whether a given nucleic acid encodes for a given polypeptide or protein. Thus, the present embodiment is clear for the skilled person, and its scope is easily determined.

Another embodiment of the invention provides the use of a binding protein according to the above description to inhibit at least one of
    HER2-receptor dimerization,
    HER2/HER3-heterodimerization,
    HER2-receptor autophosphorylation
    HER-receptor mediated signal transduction
    HER3-receptor ligand induced phosphorylation, and/or
    HER3-receptor mediated signal transduction.

HER2-receptor dimerization (also called "homodimerization") occurs in tissues overexpressing HER2 independent of a ligand. Said homodimerization leads to an intracellular autophosphrylation which can eventually lead, for example, to increased cell proliferation.

Because HER3 lacks intrinsic kinase activity, HER3 is phosphorylated in HER2-overexpressing breast cancer after formation of HER2/HER3 heterodimers, which may eventually result, for example, in apoptosis inhibition.

Said use can either take place in vitro or in vivo. As set forth above, all these processes can result in pathogenic consequences, namely by activating respective signal transduction pathways. Signal transduction pathways activated by HER2 dimerization and/or HER2/HER3-heterodimerization include mitogen-activated protein kinase (MAPK), phosphoinositide 3-kinase (PI3K/Akt), phospholipase C γ, protein kinase C (PKC), Signal transducer and activator of transcription (STAT), the Ras-Map kinase pathway and the mTOR pathway.

The phosphoinositide 3-kinase (PI3K/Akt) pathway is for example considered to be one of the critical pathways that is maintaining cell survival by blocking apoptosis. Pathologic activation thereof, e.g., by HER2/HER3-heterodimerization, may thus lead to malignant proliferation (e.g. see Examples)

Pathologic activation of HER2, e.g. by HER2-homodimerization, may lead to malignant cell migration, invasion or proliferation (e.g. see Examples; Hynes N E. and Lane H A., Nat. Rev. Cancer., 5,341-54, 2005).

Yet another embodiment of the invention provides a pharmaceutical formulation comprising a binding protein or a composition according to the above disclosure, and optionally a pharmaceutical acceptable carrier and/or diluent.

Pharmaceutical acceptable carriers and/or diluents are known to the person skilled in the art and are explained in more detail below. Even further, a diagnostic composition comprising one or more of the above mentioned recombinant binding proteins, in particular binding proteins comprising repeat domains, is considered.

A pharmaceutical formulation comprises recombinant binding proteins as described above and a pharmaceutically acceptable carrier, excipient or stabilizer, for example as described in Remington's Pharmaceutical Sciences 16$^{th}$ edition, Osol, A. Ed. [1980]. Suitable carriers, excipients or stabilizers known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers.

The formulations to be used for in vivo administration must be aseptic or sterile. This is readily accomplished by filtration through sterile filtration membranes. The pharmaceutical formulation may be administered by any suitable method within the knowledge of the person skilled in the art.

Further, in another embodiment of the present invention the use of at least one binding protein, composition or pharmaceutical formulation according to the above disclosure as a medicament is provided. Likewise, a process comprising administering a binding protein, composition or pharmaceutical formulation according to the aforementioned claims to a patient is provided. In both cases, it is preferred that the disease to be treated is a neoplastic disease, preferably cancer.

In each case, an effective amount of the binding protein, composition or pharmaceutical formulation according to the aforementioned claims is preferably administered to a patient for treating the disease.

The term "neoplastic disease", as used herein, refers to an abnormal state or condition of cells or tissue characterized by rapidly proliferating cell growth or neoplasm. In a more specific meaning, the term relates to cancerous processes, e.g., tumors and/or leukemias.

The binding proteins according to the invention demonstrated apoptotic and anti-proliferative effects (see experimental section). As neoplastic diseases are often characterized by suppression of apoptosis and/or increased proliferation, it is plausible to deduce, from these experiments, that the binding proteins according to the present invention can be used in the treatment of neoplastic diseases.

Preferably, said neoplastic disease is a disease characterized by at least one selected from the group consisting of
Amplification of the HER2 encoding gene
Overexpression of the HER2 encoding gene,
Expression of a mutated form of the HER2 encoding gene, and/or
Overexpression of the Her3 encoding gene in trastuzumab resistant tumors.

In humans, HER2 is encoded by the ERBB2 gene. The above options can be ascribed to mutations in the ERBB2 gene which can be detected by means of modern molecular diagnostics, as are currently on the market.

As used herein, the term "expression of the HER2 encoding gene" is related to cells, tissues or organs which express the HER2 receptor protein, as for example detected by immunohistochemistry (IHC). As used herein, the term "amplification or overexpression of the HER2 encoding gene" is related to indicate an abnormal level of expression of the HER2 receptor protein in a cell, tissue or organ, relative to the level of expression in a normal cell, tissue or organ, as for example detected by Immunohistochemistry (IHC).

Such IHC detection assays are known in the art and include the Clinical Trial Assay (CTA), the commercially available LabCorp 4D5 test, and the commercially available DAKO HercepTest® (DAKO, Carpinteria, Calif.). The latter assay uses a specific score range of 0 to 3+ cell staining (0 being normal expression, 3+ indicating the strongest positive expression) to identify cancers having overexpression of the HER2 protein. Thus, patients having a cancer characterized by overexpression of the HER2 protein in the range of 1+, 2+, or 3+, preferably 2+ or 3+, more preferably 3+ would benefit from the methods of therapy of the present invention.

Alternatively, Her2 expression and/or overexpression scores can also be detected by In Situ hybridization (ISH), RT-PCT and other methods.

According to a particularly preferred embodiment, said neoplastic disease is at least one selected from the group consisting
breast cancers
ovarian cancer,
gastric cancer,
stomach cancer, and/or
uterine cancer.
colorectal cancer.

Furthermore, said use is preferably complemented, in a coordinated fashion, by the administration of at least one active substance selected from the group consisting of
an antineoplastic agent
an endocrine drug, a tumor vaccine,
immunotherapy, and/or
cellular therapy.

The term "complemented, in a coordinated fashion", as used herein, shall refer to a co-administration, which is carried out under a given regimen. This includes synchronous administration of the different compounds as well as time-shifted administration of the different compounds (e.g., compound A is given once and compound B is given several times thereafter, or vice versa, or both compounds are given synchronously and one of the two is also given at later stages).

As used herein, the term "antineoplastic agent" relates to a drug, or a combination of drugs, which have antineoplastic or anticancer effects. This applies, above all, to chemotherapeutic agents, which work by impairing mitosis, effectively targeting fast-dividing cells, or by causing cells to undergo apoptosis. The majority of chemotherapeutic drugs can be divided into alkylating agents, antimetabolites, anthracyclines, plant alkaloids, topoisomerase inhibitors, and other antitumour agents.

Preferred antineoplastic agents are 5-fluorouracil, actinomycin, adriamycin, amsacrine, anthracyclines, azathioprine, bendamustine, bleomycin, carboplatin, chlorambucil, cisplatin, cyclophosphamide, daunorubicin, docetaxel, doxorubicin, epirubicin, etoposide, idarubicin, ifosfamide, irinotecan, mechlorethamine, mercaptopurine, methotrexate, mitomycin, oxaliplatin, paclitaxel, plicamycin, podophyllotoxin, teniposide, topotecan., valrubicin, vinblastine, vincristine, vincristine, vindesine, and/or vinorelbine.

Immunotherapy involves the isolation of proteins from cancer cells and subsequent immunization of cancer patients against those proteins, in the hope of stimulating an immune reaction that would kill the cancer cells. Another approach to therapeutic anti-cancer vaccination is to generate the immune response in situ in the patient. This enhances the anti-tumor immune response to tumor antigens released following lytic virus replication providing an in situ, patient specific anti-tumor vaccine as a result. Yet another approach is to immunize the patient with a compound that plays a physiological role in cancer genesis, so that the human body eliminates said compound.

Targeted drugs are a type of medication that blocks the growth of cancer cells by interfering with specific targeted molecules needed for carcinogenesis and tumor growth, rather than by simply interfering with rapidly dividing cells (e.g. with traditional chemotherapy). The main categories of targeted therapy are small molecules and monoclonal antibodies.

Small molecules falling under this definition encompass, but are not limited, to Lapatinib, Neratinib, Afatinib, Imatinib, Gefitinib, Erlotinib, Bortezomib, Bcl-2 inhibitors (e.g. Obatoclax, ABT-263, and Gossypol), PARP inhibitors (e.g. Iniparib, Olaparib), Janus kinase inhibitors, PI3K inhibitors, Apatinib, mTOR inhibitors (Everolimus), AN-152, AKT-inhibitors, HDAC inhibitors, proteasome inhibitors, Doxorubicin linked to [D-Lys(6)]-LHRH, Pegaptanib, Sunitinib, Sorafenib, Tivozanib and Pazopanib. Monoclonal antibodies falling under this definition encompass, but are not limited, to Rituximab, trastuzumab, trastuzumab-TDM1, pertuzumab, cetuximab and bevacizumab.

Endocrine drugs, as used herein, are drugs that are antagonistic to hormones or hormone receptors and thus interfere with cancer types that require hormones to grow. One example for such Endocrine drug is Tamoxifen, which is an antagonist of the estrogen receptor in breast tissue.

The term "cellular therapy", as used herein, shall relate to cell-based therapies such as adoptive transfer of modified, or unmodified, cytotoxic lymphocytes or dendritic cells.

The term "tumor vaccine", as used herein, refers to vaccines that either a) prevent infections with cancer-causing viruses (mode of action is similar to other vaccines against viral infections), b) treat existing cancer (therapeutic cancer vaccines) or c) prevent the development of cancer, or ameliorate its effects (prophylactic cancer vaccines).

In addition or alternatively thereto, said use is preferably complemented, in a coordinated fashion, by at least one other treatment selected from the group consisting of
radiotherapy
surgery, and/or
laser ablation Furthermore, a method of treatment of a human or animal subject is provided which method comprises the use according to the above disclosure. Preferably, said method of treatment relates to an indication as set forth in the above disclosure. The method comprises administering, to a human or animal in need thereof, a therapeutically effective amount of a recombinant binding protein of the invention.

The recombinant binding protein or ankyrin repeat domain according to the invention may be obtained and/or further evolved by several methods such as display on the surface of bacteriophages (WO 1990/002809, WO 2007/006665) or bacterial cells (WO 1993/010214), ribosomal display (WO 1998/048008), display on plasmids (WO 1993/008278) or by using covalent RNA-repeat protein hybrid constructs (WO 2000/032823), or intracellular expression and selection/screening such as by protein complementation assay (WO 1998/341120). Such methods are known to the person skilled in the art.

A library of ankyrin repeat proteins used for the selection/screening of a recombinant binding protein or ankyrin repeat domain according to the invention may be obtained according to protocols known to the person skilled in the art (WO 2002/020565, Binz, H. K., et al., J. Mol. Biol., 332, 489-503, 2003, and Binz et al., 2004, loc. cit). The use of such libraries for the selection of ankyrin repeat domains with specificity for the extracellular region of HER2 is exemplified in Example 1. Furthermore, ankyrin repeat domains of the present invention may be modularly assembled from ankyrin repeat modules according to the current invention and appropriate capping modules or capping repeats (Forrer, P., et al., FEBS letters 539, 2-6, 2003) using standard recombinant DNA technologies (e.g. WO 2002/020565, Binz et al., 2003, loc. cit. and Binz et al., 2004, loc. cit).

The invention is not restricted to the particular embodiments described in the Examples. Other sources may be used and processed following the general outline described below.

Definitions

The term "protein" refers to a polypeptide, wherein at least part of the polypeptide has, or is able to acquire a defined three-dimensional arrangement by forming secondary, tertiary, or quaternary structures within and/or between its polypeptide chain(s). If a protein comprises two or more polypeptides, the individual polypeptide chains may be linked non-covalently or covalently, e.g. by a disulfide bond between two polypeptides. A part of a protein, which individually has, or is able to acquire, a defined three-dimensional arrangement by forming secondary or tertiary structures, is termed "protein domain". Such protein domains are well known to the practitioner skilled in the art.

The term "recombinant" as used in recombinant protein, recombinant protein domain, recombinant binding protein and the like, means that said polypeptides are produced by the use of recombinant DNA technologies well known by the practitioner skilled in the relevant art. For example, a recombinant DNA molecule (e.g. produced by gene synthesis) encoding a polypeptide can be cloned into a bacterial expression plasmid (e.g. pQE30, Qiagen), yeast expression plasmid or mammalian expression plasmid. When, for example, such a constructed recombinant bacterial expression plasmid is inserted into an appropriate bacteria (e.g. *Escherichia coli*), this bacteria can produce the polypeptide encoded by this recombinant DNA. The correspondingly produced polypeptide is called a recombinant polypeptide.

In the context of the present invention, the term "polypeptide" relates to a molecule consisting of one or more chains of multiple, i.e. two or more, amino acids linked via peptide bonds. Preferably, a polypeptide consists of more than eight amino acids linked via peptide bonds.

The term "polypeptide tag" refers to an amino acid sequence attached to a polypeptide/protein, wherein said amino acid sequence is useful for the purification, detection, or targeting of said polypeptide/protein, or wherein said amino acid sequence improves the physicochemical behavior of the polypeptide/protein, or wherein said amino acid sequence possesses an effector function. The individual polypeptide tags, moieties and/or domains of a binding protein may be connected to each other directly or via polypeptide linkers. These polypeptide tags are all well known in the art and are fully available to the person skilled in the art. Examples of polypeptide tags are small polypeptide sequences, for example, His (e.g. the His-tag of SEQ ID NO: 6), myc, FLAG, or Strep-tags or moieties such as enzymes (for example enzymes like alkaline phosphatase), which allow the detection of said polypeptide/protein, or moieties which can be used for targeting (such as immunoglobulins or fragments thereof) and/or as effector molecules.

The term "polypeptide linker" refers to an amino acid sequence, which is able to link, for example, two protein domains, a polypeptide tag and a protein domain, a protein domain and a non-polypeptide moiety such as polyethylene glycol or two sequence tags. Such additional domains, tags, non-polypeptide moieties and linkers are known to the person skilled in the relevant art. A list of example is provided in the description of the patent application WO 2002/020565. Particular examples of such linkers are glycine-serine-linkers and proline-threonine-linkers of variable lengths; preferably, said linkers have a length between 2 and 24 amino acids; more preferably, said linkers have a length between 2 and 16 amino acids. Examples of glycine-serine-linkers are provided in SEQ ID NO: 7 to 10 and examples of a proline-threonine-linkers are provided in SEQ ID NO: 11 and 12. Preferably, the proline-threonine-linker of SEQ ID NO: 11 is preceded by GS and/or followed by GS.

The term "polymer moiety" refers to either a proteinaceous polymer moiety or a non-proteinaceous polymer moiety. A "proteinaceous polymer moiety" preferably is a polypeptide that does not form a stable tertiary structure. Examples of proteinaceous polymer moieties are XTEN® (a registered trademark of Amunix; WO 2007/103515) polypeptides, or polypeptides comprising proline, alanine and serine residues as described in WO 2008/155134. Such proteinaceous polymer moieties can be covalently attached to, for example, a repeat domain of the invention by the generation of genetic fusion polypeptides using standard DNA cloning technologies, followed by their standard expression and purification. A "non-proteinaceous polymer moiety" is a polymer moiety not built from polypeptides. Examples of non-proteinaceous polymer moieties are hydroxyethyl starch (HES), polyethylene glycol (PEG), polypropylene glycol, or polyoxyalkylene. The term "PEGylated" means that a PEG moiety is covalently attached to, for example, a polypeptide of the invention. A polymer moiety of the invention may vary widely in molecular weight. Preferably, said polymer moiety is connected by a polypeptide linker to a repeat domain.

In a specific embodiment, a PEG moiety or any other non-proteinaceous polymer can, e.g., be coupled to a cysteine thiol via a maleimide linker with the cysteine being coupled via a peptide linker to the N- or C-terminus of a repeat domain as described herein.

The term "binding protein" refers to a protein comprising one or more binding domains, one or more bioactive compounds and one or more polymer moieties as further explained below. Preferably, said binding protein comprises up to four binding domains. Furthermore, any such binding protein may comprise additional protein domains that are not binding domains, multimerization moieties, polypeptide tags, polypeptide linkers and/or a single Cys residue.

Examples of "multimerization moieties" are immunoglobulin heavy chain constant regions which pair to provide functional immunoglobulin Fc domains, and leucine zippers or polypeptides comprising a free thiol which forms an intermolecular disulfide bond between two such polypeptides. The single Cys residue may be used for conjugating other moieties to the polypeptide, for example, by using the maleimide chemistry well known to the person skilled in the art. Preferably, said binding protein is a recombinant binding protein. Also preferably, the binding domains of binding protein possess different target specificities.

The term "compete for binding" means the inability of two different binding domains of the invention to bind simultaneously to the same target, while both are able to bind the same target individually. Thus, such two binding domains compete for binding to said target. Preferably, said two competing binding domains bind to an overlapping or the same binding epitope on said target. Methods, such as competition Enzyme-Linked Immuno Sorbent Assay (ELISA) or competition SPR measurements (e.g. by using the Proteon instrument from BioRad), to determine if two binding domains compete for binding to a target, are well known to the practitioner in the art.

The term "multiparatopic binding protein" means a binding protein directed against two or mpre different epitopes located on the same target protein. For example, a multiparatopic binding protein targeting HER2 comprises at least a first binding domain targeting a first epitope on HER2, a second binding domain targeting a different second epitope on HER2, and optionally further binding domain targeting further epitopes on HER2.

The term "biparatopic binding protein" means a binding protein directed against two different epitopes located on the same target protein. For example, a biparatopic binding protein targeting HER2 comprises at least a first binding domain targeting a first epitope on HER2 and a second binding domain targeting a different second epitope on HER2. Correspondingly, a "biparatopic DARPin" comprises a first binding domain against a first epitope and a second binding domain against a different second epitope on the same target molecule.

The term "bioactive compound" refers to a compound that is disease modifying when applied to a mammal having said disease. A bioactive compound may have antagonistic or agonistic properties and can be a proteinaceous bioactive compound or a non-proteinaceous bioactive compound. Such proteinaceous bioactive compounds can be covalently attached to, for example, a binding domain of the invention by the generation of genetic fusion polypeptides using standard DNA cloning technologies, followed by their standard expression and purification. Such non-proteinaceous bioactive compounds can be covalently attached to, for example, a binding domain of the invention by chemical means, e.g., by coupling to a cysteine thiol via a maleimide linker with a cysteine being coupled via a peptide linker to the N- or C-terminus of a binding domain as described herein. Examples of proteinaceous bioactive compounds are binding domains having a distinct target specificity (e.g. neutralizing a growth factor by binding to it), cytokines (e.g. interleukins), growth factors (e.g. human growth hormone), antibodies and fragments thereof, hormones (e.g. GLP-1) and any possible proteinaceous drug. Examples of non-proteinaceous bioactive compounds are, toxins (e.g. DM1 from ImmunoGen), small molecules targeting GPCRs, antibiotics and any possible non-proteinaceous drug.

The term "binding domain" means a protein domain exhibiting the same "fold" (three-dimensional arrangement) as a protein scaffold and having a predetermined property, as defined below. Such a binding domain may be obtained by rational, or most commonly, combinatorial protein engineering techniques, skills which are known in the art (Binz et al., 2005, loc. cit.). For example, a binding domain having a predetermined property can be obtained by a method comprising the steps of (a) providing a diverse collection of protein domains exhibiting the same fold as a protein scaffold as defined further below; and (b) screening said diverse collection and/or selecting from said diverse collection to obtain at least one protein domain having said predetermined property. The diverse collection of protein domains may be provided by several methods in accordance with the screening and/or selection system being used, and may comprise the use of methods well known to the person skilled in the art, such as phage display or ribosome display. Preferably, said binding domain is a recombinant binding domain. Also preferably, said binding domain is a repeat protein or a designed repeat protein.

Accordingly, the term "binds", as used herein, relates to a binding domain that recognizes and binds a given target, but does not substantially recognize or bind other targets. Preferably, a dissociation constant in PBS of smaller than $10^{-7}$M is required for a candidate to qualify as a binding domain in the meaning of the present invention.

The term "Kd" relates to the dissociation constant, which is a specific type of equilibrium constant that measures the propensity of a larger object to separate (dissociate) reversibly into smaller components, as when a complex falls apart into its component molecules. Methods to determine dissociation constants of protein-protein interactions, such as surface plasmon resonance (SPR) based technologies (e.g. SPR equilibrium analysis) or isothermal titration calorimetry (ITC) are well known to the person skilled in the art. The measured Kd values of a particular protein-protein interaction can vary if measured under different conditions (e.g., salt concentration, pH). Thus, measurements of Kd values are preferably made with standardized solutions of protein and a standardized buffer, such as PBS.

The term "PBS" means a phosphate buffered water solution containing 137 mM NaCl, 10 mM phosphate and 2.7 mM KCl and having a pH of 7.4.

The term "protein scaffold" means a protein with exposed surface areas in which amino acid insertions; substitutions or deletions are highly tolerable. Examples of protein scaffolds that can be used to generate binding domains of the present invention are antibodies or fragments thereof such as single-chain Fv or Fab fragments, protein A from *Staphylococcus aureus*, the bilin binding protein from *Pieris brassicae* or other lipocalins, ankyrin repeat proteins or other repeat proteins, and human fibronectin. Protein scaffolds are known to the person skilled in the art (Binz et al., 2005, loc. cit.; Binz et al., 2004, loc. cit.).

The term "target" refers to an individual molecule such as a nucleic acid molecule, a polypeptide or protein, a carbohydrate, or any other naturally occurring molecule, including any part of such individual molecule, or complexes of two or more of such molecules. The target may be a whole cell or a tissue sample, or it may be any non-natural molecule or moiety. Preferably, the target is a naturally occurring or non-natural polypeptide or a polypeptide containing chemical modifications, for example modified by natural or non-natural phosphorylation, acetylation, or methylation. In the particular application of the present invention, the target is the extracellular region of HER2.

The term "predetermined property" refers to a property such as binding to a target, blocking of a target, activation of a target-mediated reaction, enzymatic activity, and related further properties. Depending on the type of desired property, one of ordinary skill will be able to identify format and necessary steps for performing screening and/or selection of a binding domain with the desired property. Preferably, said predetermined property is binding to a target.

The definitions hereinafter for repeat proteins are based on those in patent application WO 2002/020565. Patent application WO 2002/020565 further contains a general description of repeat protein features, techniques and applications.

The term "repeat protein" refers to a protein comprising one or more repeat domains. Preferably, each of said repeat proteins comprises up to four repeat domains. More preferably, each of said repeat proteins comprises up to two repeat domains. Most preferably, each of the repeat proteins comprises only one repeat domain. Furthermore, said repeat protein may comprise additional non-repeat protein domains, polypeptide tags and/or polypeptide linkers.

The term "repeat domain" refers to a protein domain comprising two or more consecutive repeat units (modules) as structural units, wherein said structural units have the same fold, and stack tightly to create a superhelical structure having a joint hydrophobic core. Preferably, a repeat domain further comprises an N-terminal and/or a C-terminal capping unit (or module). Even more preferably, said N-terminal and/or C-terminal capping units (or modules) are capping repeats.

The term "designed repeat protein" and "designed repeat domain" refer to a repeat protein or repeat domain, respectively, obtained as the result of the inventive procedure explained in patent application WO 2002/020565. Designed repeat proteins and designed repeat domains are synthetic and not from nature. They are man-made proteins or domains, respectively, obtained by expression of correspondingly designed nucleic acids. Preferably, the expression is done in eukaryotic or prokaryotic cells, such as bacterial cells, or by using a cell-free in vitro expression system. Accordingly, a designed ankyrin repeat protein (i.e. a DARPin) corresponds to a recombinant binding protein of the invention comprising at least one ankyrin repeat domain.

The term "structural unit" refers to a locally ordered part of a polypeptide, formed by three-dimensional interactions between two or more segments of secondary structure that are near one another along the polypeptide chain. Such a structural unit exhibits a structural motif. The term "structural motif" refers to a three-dimensional arrangement of secondary structure elements present in at least one structural unit. Structural motifs are well known to the person skilled in the art. Structural units alone are not able to acquire a defined three-dimensional arrangement; however, their consecutive arrangement, for example as repeat modules in a repeat domain, leads to a mutual stabilization of neighboring units resulting in a superhelical structure.

The term "repeat unit" refers to amino acid sequences comprising repeat sequence motifs of one or more naturally occurring repeat proteins, wherein said "repeat units" are found in multiple copies, and which exhibit a defined folding topology common to all said motifs determining the fold of the protein. Such repeat units correspond to the "repeating structural units (repeats)" of repeat proteins as described by Forrer et al., 2003, loc. cit. or the "consecutive homologous structural units (repeats)" of repeat proteins as described by Binz et al, 2004, loc. cit. Such repeat units comprise framework residues and interaction residues. Examples of such repeat units are armadillo repeat units, leucine-rich repeat units, ankyrin repeat units, tetratricopeptide repeat units, HEAT repeat units, and leucine-rich variant repeat units. Naturally occurring proteins containing two or more such repeat units are referred to as "naturally occurring repeat proteins". The amino acid sequences of the individual repeat units of a repeat protein may have a significant number of mutations, substitutions, additions and/or deletions when compared to each other, while still substantially retaining the general pattern, or motif, of the repeat units.

Accordingly, the term "ankyrin repeat unit" shall mean a repeat unit, which is an ankyrin repeat as described, for example, by Forrer et al., 2003, loc. cit. Ankyrin repeats are well known to the person skilled in the art. The term "ankyrin repeat domain" refers to a repeat domain comprising two or more consecutive ankyrin repeat units (modules) as structural units, and, preferably, an N-terminal and/or a C-terminal capping unit (or module).

The term "framework residues" relates to amino acid residues of the repeat units, or the corresponding amino acid residues of the repeat modules, which contribute to the folding topology, i.e. which contribute to the fold of said repeat unit (or module) or which contribute to the interaction with a neighboring unit (or module). Such contribution might be the interaction with other residues in the repeat unit (or module), or the influence on the polypeptide backbone conformation as found in α-helices or β-sheets, or amino acid stretches forming linear polypeptides or loops.

The term "target interaction residues" refers to amino acid residues of the repeat units, or the corresponding amino acid residues of the repeat modules, which contribute to the interaction with target substances. Such contribution might be the direct interaction with the target substances, or the influence on other directly interacting residues, e.g. by stabilizing the conformation of the polypeptide of a repeat unit (or module) to allow or enhance the interaction of directly interacting residues with said target. Such framework and target interaction residues may be identified by analysis of the structural data obtained by physicochemical methods, such as X-ray crystallography, NMR and/or CD spectroscopy, or by comparison with known and related structural information well known to practitioners in structural biology and/or bioinformatics.

Preferably, the repeat units used for the deduction of a repeat sequence motif are homologous repeat units, wherein the repeat units comprise the same structural motif and wherein more than 70% of the framework residues of said repeat units are homologous to each other. Preferably, more than 80% of the framework residues of said repeat units are homologous. Most preferably, more than 90% of the framework residues of said repeat units are homologous. Computer programs to determine the percentage of homology between polypeptides, such as Fasta, Blast or Gap, are known to the person skilled in the art. Further preferably, the repeat units used for the deduction of a repeat sequence motif are homologous repeat units obtained from repeat domains selected on a defined target.

The term "repeat sequence motif" refers to an amino acid sequence, which is deduced from one or more repeat units or repeat modules. Preferably, said repeat units or repeat modules are from repeat domains having binding specificity for the same target. Such repeat sequence motifs comprise framework residue positions and target interaction residue positions. Said framework residue positions correspond to the positions of framework residues of the repeat units (or modules). Likewise, said target interaction residue positions correspond to the positions of target interaction residues of the repeat units (or modules). Repeat sequence motifs comprise fixed positions and randomized positions. The term "fixed position" refers to an amino acid position in a repeat sequence motif, wherein said position is set to a particular amino acid. Most often, such fixed positions correspond to the positions of framework residues and/or the positions of target interaction residues that are specific for a certain target. The term "randomized position" refers to an amino acid position in a repeat sequence motif, wherein two or more amino acids are allowed at said amino acid position, for example, wherein any of the usual twenty naturally occurring amino acids are allowed, or wherein most of the twenty naturally occurring amino acids are allowed, such as amino acids other than cysteine, or amino acids other than glycine, cysteine and proline. Most often, such randomized positions correspond to the positions of target interaction residues. However, some positions of framework residues may also be randomized.

The term "folding topology" refers to the tertiary structure of said repeat units or repeat modules. The folding topology will be determined by stretches of amino acids forming at least parts of α-helices or β-sheets, or amino acid stretches forming linear polypeptides or loops, or any combination of α-helices, β-sheets and/or linear polypeptides/loops. For example, an ankyrin repeat unit/module consists of a β-turn, followed by two antiparallel α-helices and a loop that reaches the turn of the next repeat unit/module.

The term "consecutive" refers to an arrangement, wherein the repeat units or repeat modules are arranged in tandem. In designed repeat proteins, there are at least 2, usually about 2 to 6, in particular at least about 6, frequently 20 or more repeat units (or modules). In most cases, repeat units (or modules) of a repeat domain will exhibit a high degree of sequence identity (same amino acid residues at corresponding positions) or sequence similarity (amino acid residues being different, but having similar physicochemical properties), and some of the amino acid residues might be key residues being strongly conserved. However, a high degree of sequence variability by amino acid insertions and/or deletions, and/or substitutions between the different repeat units (or modules) of a repeat domain may be possible as long as the common folding topology of the repeat units (or modules) is maintained.

Methods for directly determining the folding topology of repeat proteins by physico-chemical means such as X-ray crystallography, NMR or CD spectroscopy, are well known to the practitioner skilled in the art. Methods for identifying and determining repeat units or repeat sequence motifs or for identifying families of related proteins comprising such repeat units or motifs, such as homology searches (BLAST etc.), are well established in the field of bioinformatics, and are well known to the practitioner in the art. The step of refining an initial repeat sequence motif may comprise an iterative process.

The term "repeat modules" refers to the repeated amino acid sequences of the designed repeat domains, which are originally derived from the repeat units of naturally occurring repeat proteins. Each repeat module comprised in a repeat domain is derived from one or more repeat units of the family or subfamily of naturally occurring repeat proteins, e.g. the family of armadillo repeat proteins or ankyrin repeat proteins. Further preferably, each repeat module comprised in a repeat domain comprises a repeat sequence motif deduced from homologous repeat units obtained from repeat domains selected on a target, for example as described in Example 1 and having the same target specificity.

Accordingly, the term "ankyrin repeat module" shall mean a repeat module, which is originally derived from the repeat units of naturally occurring ankyrin repeat proteins. Ankyrin repeat proteins are well known to the person skilled in the art.

"Repeat modules" may comprise positions with amino acid residues present in all copies of corresponding repeat modules ("fixed positions") and positions with differing or "randomized" amino acid residues ("randomized positions").

The term "capping module" refers to a polypeptide fused to the N- or C-terminal repeat module of a repeat domain, wherein said capping module forms tight tertiary interactions (i.e. tertiary structure interactions) with said repeat module thereby providing a cap that shields the hydrophobic core of said repeat module at the side not in contact with the consecutive repeat module from the solvent. Said N- and/or C-terminal capping module may be, or may be derived from, a capping unit or other structural unit found in a naturally occurring repeat protein adjacent to a repeat unit. The term "capping unit" refers to a naturally occurring folded polypeptide, wherein said polypeptide defines a particular structural unit which is N- or C-terminally fused to a repeat unit, wherein said polypeptide forms tight tertiary structure interactions with said repeat unit thereby providing a cap that shields the hydrophobic core of said repeat unit at one side from the solvent. Preferably, capping modules or capping units are capping repeats. The term "capping repeat" refers to capping module or capping unit having a similar or the same fold as said adjacent repeat unit (or module) and/or sequence similarities to said adjacent repeat unit (or module). Capping modules and capping repeats are described in WO 2002/020565 and by Interlandi et al., 2008 (loc. cit.).

Examples of N-terminal ankyrin capping modules (i.e. N-terminal capping repeats) are SEQ ID NO: 1, 2, 3, 13, 14, 20, 26, 27 36, 40, 44, 45, 50, 54, 124, 128 and 132 and examples of ankyrin C-terminal capping modules (i.e. C-terminal capping repeats) are SEQ ID NO: 4, 5, 19, 24, 25, 33, 34, 35, 39, 43, 48, 49, 53, 57, 127, 131 and 135.

For example, the N-terminal ankyrin capping module of SEQ ID NO: 13 is encoded by the amino acids from position 1 to 32 and the C-terminal capping module of SEQ ID NO: 19 is encoded by the amino acids from position 99 to 126.

A recombinant binding protein according to the invention comprises at least one ankyrin repeat domain, wherein said ankyrin repeat domain has binding specificity for mammalian extracellular region of HER2.

The term "has binding specificity for a target", "specifically binding to a target" or "target specificity" and the like means that a binding protein or binding domain binds in PBS to a target with a lower dissociation constant than to an unrelated protein such as the $E.\ coli$ maltose binding protein (MBP). Preferably, the dissociation constant in PBS for the target is at least 10, more preferably at least $10^2$, even more preferably at least $10^3$, or most preferably at least $10^4$ times lower than the corresponding dissociation constant for MBP.

The term "consensus sequence" refers to an amino acid sequence, wherein said consensus sequence is obtained by structural and/or sequence aligning of multiple repeat units. Using two or more structural and/or sequence aligned repeat units, and allowing for gaps in the alignment, it is possible to determine the most frequent amino acid residue at each position. The consensus sequence is that sequence which comprises the amino acids which are most frequently represented at each position. In the event that two or more amino acids are represented above-average at a single position, the consensus sequence may include a subset of those amino acids. Said two or more repeat units may be taken from the repeat units comprised in a single repeat protein, or from two or more different repeat proteins.

Consensus sequences and methods to determine them are well known to the person skilled in the art.

A "consensus amino acid residue" is the amino acid found at a certain position in a consensus sequence. If two or more, e.g. three, four or five, amino acid residues are found with a similar probability in said two or more repeat units, the consensus amino acid may be one of the most frequently found amino acids or a combination of said two or more amino acid residues.

Further preferred are non-naturally occurring capping modules, repeat modules, binding proteins or binding domains.

The term "non-naturally occurring" means synthetic or not from nature, more specifically, the term means made from the hand of man. The term "non-naturally occurring binding protein" or "non-naturally occurring binding domain" means that said binding protein or said binding domain is synthetic (i.e. produced by chemical synthesis from amino acids) or recombinant and not from nature. "Non-naturally occurring binding protein" or "non-naturally occurring binding domain" is a man-made protein or domain, respectively, obtained by expression of correspondingly designed nucleic acids. Preferably, the expression is done in eukaryotic or bacterial cells, or by using a cell-free in vitro expression system. Further, the term means that the sequence of said binding protein or said binding domain is not present as a non-artificial sequence entry in a sequence database, for example in GenBank, EMBL-Bank or Swiss-Prot. These databases and other similar sequence databases are well known to the person skilled in the art.

General modifications and derivatives of the ankyrin repeat domains according to the invention; particularly of the ankyrin repeat modules and capping modules according to the invention:

Further preferred is a N-terminal or C-terminal ankyrin capping module comprising an N-terminal or C-terminal ankyrin capping repeat, respectively, wherein one or more of the amino acids residues in said capping repeat are replaced by an amino acid residue found at the corresponding position on alignment of a corresponding ankyrin capping unit or ankyrin repeat unit.

The replacement of amino acids can be by any of the 20 most often naturally occurring amino acids, preferably by amino acids selected from the group consisting of A, D, E, F, H, I, K, L, M, N, Q, R, S, T, V, W and Y; and more preferably from the group consisting of A, D, E, H, I, K, L, Q, R, S, T, V, and Y. Also preferably, the replacement of amino acids is by a homologous amino acid; i.e. an amino acid is replaced by an amino acid having a side chain with similar biophysical properties. For example, the negative charged amino acid D may be replaced by the negative charged amino acid E, or a hydrophobic amino acid such as L may be replaced by A, I or V. The replacement of an amino acid by a homologous amino acid is well known to the person skilled in the art.

Also preferred is a C-terminal ankyrin capping module comprising the amino acid A at position 27 and 28 of any of the above C-terminal capping modules based on SEQ ID NO: 4, 5, 19, 24, 25, 33, 34, 35, 39, 43, 48, 49, 53, 57, 127, 131 or 135

Also preferred is a C-terminal capping module comprising the amino acids from position 1 to 26 or from position 1 to 27 of any of the above C-terminal capping modules based on SEQ ID NO: 4, 5, 19, 24, 25, 33, 34, 35, 39, 43, 48, 49, 53, 57, 127, 131 or 135.

Amino acids G at position 1 and/or S at position 2 of SEQ ID NO: 1, 2, 3, 13, 14, 20, 26, 27, 36, 40, 44, 45, 50, 54, 124, 128 or 132 can be removed from N-terminal ankyrin capping modules without any apparent influence on the properties. These two amino acids serve as linkers to connect the ankyrin repeat domain to further amino acids and proteins. The invention also comprises such ankyrin repeat domains comprising N-terminal ankyrin capping modules wherein G at position 1 and/or S at position 2 are removed. It is understood that the amino acid positions (e.g. "position 33") in an ankyrin repeat domain as defined herein are adapted accordingly, resulting in a number shift, e.g. "position 33" will become "position 32", if one amino acid is missing, or "position 33" will become "position 31", if two amino acid are missing.

An ankyrin capping module of an ankyrin repeat domain of the invention can be exchanged by an ankyrin capping module by combining techniques, such as alignment of amino acid sequences, mutagenesis and gene synthesis, known to the person skilled in the art. For example, the C-terminal capping repeat of SEQ ID NO: 79 can be replaced by the C-terminal capping repeat of SEQ ID NO: 5 by (i) determination of the C-terminal capping repeat of SEQ ID NO: 79 (i.e. sequence position 99 to 126) by sequence alignment with SEQ ID NO: 5, (ii) replacing the sequence of the determined C-terminal capping repeat of SEQ ID NO: 79 with the sequence of SEQ ID NO: 5, (iii) generation of a gene encoding the repeat domain encoding the exchanged C-terminal capping module, (iv) expressing of the modified repeat domain in the cytoplasm of *E. coli* and (v) purification of the modified repeat domain by standard means. As a further example, the N-terminal capping repeat of SEQ ID NO: 79 can be replaced by the N-terminal capping repeat of SEQ ID NO: 3 by (i) determination of the N-terminal capping repeat of SEQ ID NO: 79 (i.e. sequence position 1 to 32) by sequence alignment with SEQ ID NO: 3, (ii) replacing the sequence of the determined N-terminal capping repeat of SEQ ID NO: 79 with the sequence of SEQ ID NO: 3, (iii) generation of a gene encoding the repeat domain encoding the exchanged N-terminal capping module, (iv) expressing of the modified repeat domain in the cytoplasm of *E. coli* and (v) purification of the modified repeat domain by standard means.

Furthermore, an ankyrin repeat domain of the invention can be constructed genetically by assembling a N-terminal ankyrin capping module (e.g. the N-terminal capping repeat of SEQ ID NO: 3) followed by one or more repeat modules (e.g. the two ankyrin repeat modules comprising the amino acid residues from position 33 to 99 of SEQ ID NO: 79) and a C-terminal capping module (e.g. the C-terminal capping repeat of SEQ ID NO: 5) by means of gene synthesis. The genetically assembled repeat domain gene can then be expressed in *E. coli* as described above.

Further preferred is a recombinant binding protein, repeat domain, repeat module, N-terminal capping module or C-terminal capping module having an amino acid sequence devoid of amino acids C, M or N.

Further preferred is a recombinant binding protein, repeat domain, repeat module, N-terminal capping module or C-terminal capping module having an amino acid sequence devoid of amino acid N followed by G.

Further preferred is a recombinant binding protein or repeat domain comprising any such N-terminal or C-terminal capping module.

In a further preferred embodiment of a recombinant binding protein comprising an ankyrin repeat domain according to the present invention, one or more of the amino acid residues of the N-terminal capping module of said repeat domain is exchanged by an amino acid residue found at the corresponding position on alignment of an N-terminal capping unit. Preferably, up to 30% of the amino acid residues are exchanged, more preferably, up to 20%, and even more preferably, up to 10% of the amino acid residues are exchanged. Most preferably, such an N-terminal capping unit is a naturally occurring N-terminal capping unit.

In a further preferred embodiment of a recombinant binding protein comprising an ankyrin repeat domain according to the present invention, one or more of the amino acid residues of the C-terminal capping module of said repeat domain is exchanged by an amino acid residue found at the corresponding position on alignment of a C-terminal capping unit. Preferably, up to 30% of the amino acid residues are exchanged, more preferably, up to 20%, and even more preferably, up to 10% of the amino acid residues are exchanged. Most preferably, such a C-terminal capping unit is a naturally occurring C-terminal capping unit.

In still another particular embodiment, up to 30% of the amino acid residues, more preferably, up to 20%, and even more preferably, up to 10% of the amino acid residues are exchanged with amino acids which are not found in the corresponding positions of repeat units, N-terminal capping units or C-terminal capping units.

In a further preferred embodiment of a recombinant binding protein comprising an ankyrin repeat domain according to the present invention, one or more of the amino acid residues of the repeat modules of said ankyrin repeat domain are exchanged by an amino acid residue found at the corresponding position on alignment of a repeat unit. Preferably, up to 30% of the amino acid residues are exchanged, more preferably, up to 20%, and even more preferably, up to 10% of the amino acid residues are exchanged. Most preferably, such a repeat unit is a naturally occurring repeat unit.

In still another particular embodiment, up to 30% of the amino acid residues, more preferably, up to 20%, and even more preferably, up to 10% of the amino acid residues are exchanged with amino acids which are not found in the corresponding positions of repeat units.

In further embodiments, any of the recombinant HER2 binding proteins or domains described herein may be covalently bound to one or more additional moieties, including, for example, a moiety that binds to a different target to create a dual-specificity binding agent, a bioactive compound, a labeling moiety (e.g. a fluorescent label such as fluorescein, or a radioactive tracer), a moiety that facilitates protein purification (e.g. a small peptide tag, such as a His- or strep-tag), a moiety that provides effector functions for improved therapeutic efficacy (e.g. the Fc part of an antibody to provide antibody-dependent cell-mediated cytotoxicity, a toxic protein moiety such as *Pseudomonas aeruginosa* exotoxin A (ETA) or a small molecular toxic agent such as maytansinoids or DNA alkylating agents) or a moiety that provides improved pharmacokinetics. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein between the concentration shortly after administration and the concentration shortly before the next administration). Moieties that tend to slow clearance of a protein from the blood include hydroxyethyl starch (HES), polyethylene glycol (PEG), sugars (e.g. sialic acid), well-tolerated protein moieties (e.g. Fc fragments or serum albumin), and binding domains or peptides with specificity and affinity for abundant serum proteins, such as antibody Fc fragments or serum albumin. Examples of such binding domains or repeat domains with affinity for serum albumin are provided in WO 2012/069654. The recombinant binding protein of the invention may be attached to a moiety that reduces the clearance rate of polypeptides in a mammal (e.g. in mouse, rat, or human) by greater than three-fold relative to the unmodified polypeptides.

In one particular embodiment the invention relates to a recombinant binding protein comprising the first repeat domain binding to HER2, the second repeat domain binding to HER2 and further comprising one or more ankyrin repeat domains specifically binding to human serum albumin. Examples of repeat domains with specificity for HER2 are given herein and examples of ankyrin repeat domains with specificity to human serum albumin are described in WO 2012/069654. Such domains can be linked by a polypeptide linker by genetic means by methods known to the person skilled in the art.

Another preferred embodiment is a recombinant binding protein wherein the first repeat domain and the second repeat domain are ankyrin repeat domains with binding specificity for HER2 comprising one, two, three or more internal repeat modules that will participate in binding to HER2. Preferably, such ankyrin repeat domains comprise an N-terminal capping module, one to four internal repeat modules, and a C-terminal capping module. Preferably, said capping modules are capping repeats. Also preferably, said capping modules will participate in binding to HER2.

Further, any of the above mentioned pharmaceutical composition is considered for the treatment of a disorder.

The invention further provides methods of treatment. The method comprises administering, to a patient in need thereof, a therapeutically effective amount of a recombinant binding protein of the invention.

Further, a method of treating a pathological condition in a mammal including man, comprising administering to a patient in need thereof an effective amount of the above mentioned pharmaceutical composition is considered.

EXAMPLES

All of the starting materials and reagents disclosed below are known to those skilled in the art, and are available commercially or can be prepared using well-known techniques.

Materials

Chemicals were purchased from Fluka (Switzerland). Oligonucleotides were from Microsynth (Switzerland). Unless stated otherwise, DNA polymerases, restriction enzymes and buffers were from New England Biolabs (USA) or Fermentas (Lithuania). The cloning and protein production strain was *E. coli* XL1-blue (Stratagene, USA) or BL21 (Novagen, USA). Recombinant human HER2 ectodomain (ErbB2 S22-N530-Flag and ErbB2 S22-E645-Flag produced in CHO cells by standard means) was purchased from CSIRO Enquiries (Australia). Biotinylated Her2 ectodomain was obtained chemically via coupling of the biotin moiety to primary amines of the protein using standard biotinylation reagents and methods (Pierce, USA). Cell lines were purchased from LGC/ATCC (France/USA; Cat. No: BT474-HTB-20, SKBR-3-HTB-30, NCI-N87-CRL5822, ZR75-30-CRL1504, HCC1419-CRL2326, MDA-MB175 VII-HTB-25). Cell culture media were from Invitrogen/Lubio (Switzerland). Fetal calf serum was from PAA. Assay reagent for detection of cell proliferation, Cell Proliferation ELISA, BrdU (colorimetric) (Cat. No. 1164722900) was from Roche, Switzerland and the assay reagent for detection of apoptosis, Caspase Glo 3/7 (Cat. No. G8091) was from Promega and the Switzerland and the Cell Death Detection ELISAPLUS system (11 774 425 001) from Roche, Switzerland. Cell transfection reagent, Lipofectamin 2000 (11668027) was from Invitrogen Switzerland. FACS analyses were performed using the FACS Canto II System from Becton-Dickinson (Switzerland). The binding of DARPins to Her2 was detected using an anti-Penta-His Alexa Fluor 647 conjugate (Cat. No. A21445; Lubio Switzerland). Accutase (Cat. No: L-11-007) was from PAA. Trastuzumab was purchased from Kantonal Apotheke Zurich and pertuzumab was synthesized by Evitra (Switzerland). The expression vector for GFP-tagged Her2 (Cat. No. RG212583) was from Origene USA.

Molecular Biology

Unless stated otherwise, methods are performed according to described protocols (Sambrook J., Fritsch E. F. and Maniatis T., Molecular Cloning: A Laboratory Manual, Cold Spring Harbor Laboratory 1989, New York).

Proliferation Analysis

Effects of DARPins on cell proliferation were determined by measuring DNA synthesis using BrdU-labeling (BrdU, Cell Proliferation ELISA, Roche). Briefly, 10000 BT474 cells were seeded per well in a 96 well plate in 100 ul complete medium and incubated for 24 h. DARPins and benchmarks were added for an additional 72 h. BrdU for cell labeling was added for the last 24 h. Labeled (proliferating) cells were detected according to the manufactures protocol. The data were analyzed using the GraphPad prism software, plotting log [c] on the x-axis against OD450-602 nm on the y-axis. Data were fitted using a non-linear regression fit (log(antagonist) vs. response—Variable slope (four parameters)).

Apoptosis Analysis

Induction of apoptosis by DARPins was determined by measuring Caspase3/7 activation using the Caspase 3/7-Glo systems (Promega, Switzerland). Briefly, 10000 BT474 cells were seeded per well in a 96 well plate in 100 ul complete medium and incubated for 24 h. DARPins and benchmarks were added for an additional 24 h. Caspase Glo reagent was added according to the manufactures protocol for 1 h. Caspase 3/7 activation was monitored by measuring luciferase activity.

Alternatively induction of apoptosis was determined using the Cell Death Detection ELISAPLUS system (Roche, Switzerland). The assay was performed according to the manufactures protocol. Cell number and incubations times were similar to the Caspase Glo readout.

The data were analyzed using the GraphPad prism software, plotting concentration on the x-axis against OD405/490 nm or RLU on the y-axis. Data were fitted using a non-linear regression fit (log(agonist) vs. response—Variable slope (four parameters)).

Designed Ankyrin Repeat Protein Libraries

Methods to generate designed ankyrin repeat protein libraries are described (WO 2002/020565; Binz et al. 2003, loc. cit.; Binz et al. 2004, loc. cit.). By such methods designed ankyrin repeat protein libraries having randomized ankyrin repeat modules and/or randomized capping modules can be constructed. For example, such libraries could accordingly be assembled based on a fixed N-terminal capping module (e.g. the N-terminal capping module of SEQ ID NO: 2) or a randomized N-terminal capping module according to the sequence motif of SEQ ID NO: 60, one or more randomized repeat modules according to the sequence motif of SEQ ID NO: 58 or 59, and a fixed C-terminal capping module (e.g. the C-terminal capping module of SEQ ID NO: 5) or a randomized C-terminal capping module according to the sequence motif of SEQ ID NO: 61. Preferably, such libraries are assembled to not have the amino acids C, G, M, N (in front of a G residue) or P at randomized positions of repeat or capping modules. In addition, randomized repeat modules according to the sequence motif of SEQ ID NO: 58 or 59 could be further randomized at position 10 and/or position 17; the randomized N-terminal capping module according to the sequence motif of SEQ ID NO: 60 could be further randomized at position 7 and/or position 9; and the randomized C-terminal capping modules according to the sequence motif of SEQ ID NO: 61 could be further randomized at positions 10, 11 and/or 17.

Furthermore, such randomized modules in such libraries may comprise additional polypeptide loop insertions with randomized amino acid positions. Examples of such polypeptide loop insertions are complement determining region (CDR) loop libraries of antibodies or de novo generated peptide libraries. For example, such a loop insertion could be designed using the structure of the N-terminal ankyrin repeat domain of human ribonuclease L (Tanaka, N., Nakanishi, M, Kusakabe, Y, Goto, Y., Kitade, Y, Nakamura, K. T., EMBO J. 23(30), 3929-3938, 2004) as guidance. In analogy to this ankyrin repeat domain where ten amino acids are inserted in the beta-turn present close to the boarder of two ankyrin repeats, ankyrin repeat proteins libraries may contain randomized loops (with fixed and randomized positions) of variable length (e.g. 1 to 20 amino acids) inserted in one or more beta-turns of an ankyrin repeat domain.

Any such N-terminal capping module of an ankyrin repeat protein library preferably possesses the RELLKA or RILKAA motif instead of the RILLAA motif (e.g. present from position 21 to 26 in SEQ ID NO: 65) and any such C-terminal capping module of an ankyrin repeat protein library preferably possesses the KAA or KLA motif instead of the KLN motif (e.g. the last three amino acids in SEQ ID NO: 65).

The design of such an ankyrin repeat protein library may be guided by known structures of an ankyrin repeat domain interacting with a target. Examples of such structures, identified by their Protein Data Bank (PDB) unique accession or identification codes (PDB-IDs), are 1WDY, 3V31, 3V30, 3V2X, 3V20, 3UXG, 3TWQ-3TWX, 1N11, 1S70 and 2ZGD.

Examples of designed ankyrin repeat protein libraries, such as the N2C and N3C designed ankyrin repeat protein libraries, are described (WO 2002/020565; Binz et al. 2003, loc. cit.; Binz et al. 2004, loc. cit.). The digit in N2C and N3C describes the number of randomized repeat modules present between the N-terminal and C-terminal capping modules.

The nomenclature used to define the positions inside the repeat units and modules is based on Binz et al. 2004, loc. cit. with the modification that borders of the ankyrin repeat modules and ankyrin repeat units are shifted by one amino acid position. For example, position 1 of an ankyrin repeat module of Binz et al. 2004 (loc. cit.) corresponds to position 2 of a ankyrin repeat module of the current disclosure and consequently position 33 of a ankyrin repeat module of Binz et al. 2004, loc. cit. corresponds to position 1 of a following ankyrin repeat module of the current disclosure.

All the DNA sequences were confirmed by sequencing, and the calculated molecular weight of all described proteins was confirmed by mass spectrometry.

Example 1: Selection of Binding Proteins Comprising Ankyrin Repeat Domains with Binding Specificity for HER2

Using ribosome display (Hanes, J. and Plückthun, A., PNAS 94, 4937-42, 1997) many designed ankyrin repeat proteins (DARPins) with binding specificity for the ectodomain of HER2 were selected from DARPin libraries as described by Binz et al. 2004 (loc. cit.). Their binding specificity was assessed by crude extract ELISA (see below) indicating that hundreds of HER2-specific binding proteins were selected. HER2-specific inhibition of proliferation and induction of apoptosis of the selected clones was measured by testing biparatopic DARPins for their ability to inhibit proliferation of BT474 cells.

For example, the ankyrin repeat domains of SEQ ID NO: 62 to 82, 112 to 121 constitute amino acid sequences of selected binding proteins comprising an ankyrin repeat domain with binding specificity for HER2. Individual ankyrin repeat modules from such ankyrin repeat domains with binding specificity to HER2 are provided in SEQ ID NO: 15 to 18, 21 to 23, 28 to 32, 37, 38, 41, 42, 46, 47, 51, 52, 55, 56, 125, 126, 129, 130, 133 and 134.

Individual capping modules of such ankyrin repeat domains with binding specificity to HER2 are provided in SEQ ID NO: 13, 14, 19, 20, 24 to 27, 33 to 36, 39, 40, 43 to 45, 48 to 50, 53, 54, 57, 124, 127, 128, 131, 132 and 135.

Selection of HER2 Specific Ankyrin Repeat Proteins by Ribosome Display

The selection of HER2 specific ankyrin repeat proteins was performed by ribosome display (Hanes and Plückthun, loc. cit.) using human HER2 as target proteins, libraries of designed ankyrin repeat proteins as described above and established protocols (Zahnd, C., Amstutz, P. and Plückthun, A., Nat. Methods 4, 69-79, 2007). The number of reverse transcription (RT)-PCR cycles after each selection round was constantly reduced from 45 to 30, adjusting to the yield due to enrichment of binders. The first four rounds of selection employed standard ribosome display selection, using decreasing target concentration and increasing washing stringency to increase selection pressure from round 1 to round 4 (Binz et al. 2004, loc. cit.). To enrich high affinity anti-HER2 DARPins, the output from the fourth round of standard ribosome display selection (above) was subjected to an off-rate selection round with increased selection stringency (Zahnd, 2007, loc. cit.). A final standard selection round was performed to amplify and recover the off-rate selected binding proteins.

Selected Clones Bind Specifically to HER2 as Shown by Crude Extract ELISA

Individual selected DARPins specifically binding the ectodomain of HER2 were identified by enzyme-linked immunosorbent assay (ELISA) using crude *Escherichia coli* extracts of DARPin expression cells using standard protocols. DARPins selected by ribosome display were cloned into the pQE30 (Qiagen) expression vector, transformed into *E. coli* XL1-Blue (Stratagene) and then grown overnight at 37° C. in a 96-deep-well plate (each clone in a single well) containing 1 ml growth medium (2YT containing 1% glucose and 100 μg/ml ampicillin). 1 ml of fresh 2YT containing 50 μg/ml ampicillin was inoculated with 100 μl of the overnight culture in a fresh 96-deep-well plate. After incubation for 2 h at 37° C., expression was induced with IPTG (1 mM final concentration) and continued for 3 h. Cells were harvested, resuspended in 100 μl B-PERII (Pierce) and incubated for 15 min at room temperature with shaking. Then, 900 μl PBS-TC (PBS supplemented with 0.25% Casein hydrolysate, 0.1% Tween 20®, pH 7.4) were added and cell debris were removed by centrifugation. 100 μl of each lysed clone were applied to a well of a Neutravidin coated MaxiSorp plate containing either HER2 or the unrelated MBP immobilized via their biotin moiety and incubated for 1 h at RT. After extensive washing with PBS-T (PBS supplemented with 0.1% Tween 20®, pH 7.4) the plate was developed using standard ELISA procedures using the monoclonal horse-radish-labeled anti-RGS(His)$_4$ antibody (34650, Qiagen) Binding was then detected by POD substrate (Roche). The color development was measured at 405 nm. Screening of several hundred clones by such a crude cell extract ELISA revealed more than hundred different DARPins with specificity for HER2. These binding proteins were chosen for further analysis. Examples of amino acid sequences of selected ankyrin repeat domains that specifically bind to the ectodomain HER2 are provided in SEQ ID NO: 62 to 82 and 112 to 121.

These ankyrin repeat domains with binding specificity for HER2 and a negative control ankyrin repeat domain with no binding specificity for HER2 (i.e. SEQ ID NO: 111) were cloned into a pQE (QIAgen, Germany) based expression vector providing an N-terminal His-tag to facilitate simple protein purification as described below. Thus, expression vectors encoding the following DARPins were constructed:

DARPin #1 (SEQ ID NO: 62 with a His-tag (SEQ ID NO: 6) fused to its N-terminus);
DARPin #2 (SEQ ID NO: 63 with a His-tag (SEQ ID NO: 6) fused to its N-terminus);
DARPin #3 (SEQ ID NO: 64 with a His-tag (SEQ ID NO: 6) fused to its N-terminus);
DARPin #5 (SEQ ID NO: 66 with a His-tag (SEQ ID NO: 6) fused to its N-terminus);
DARPin #6 (SEQ ID NO: 67 with a His-tag (SEQ ID NO: 6) fused to its N-terminus);
DARPin #7 (SEQ ID NO: 68 with a His-tag (SEQ ID NO: 6) fused to its N-terminus);
DARPin #8 (SEQ ID NO: 69 with a His-tag (SEQ ID NO: 6) fused to its N-terminus);
DARPin #9 (SEQ ID NO: 70 with a His-tag (SEQ ID NO: 6) fused to its N-terminus);
DARPin #10 (SEQ ID NO: 71 with a His-tag (SEQ ID NO: 6) fused to its N-terminus);
DARPin #11 (SEQ ID NO: 72 with a His-tag (SEQ ID NO: 6) fused to its N-terminus);
DARPin #12 (SEQ ID NO: 73 with a His-tag (SEQ ID NO: 6) fused to its N-terminus);
DARPin #13 (SEQ ID NO: 74 with a His-tag (SEQ ID NO: 6) fused to its N-terminus);
DARPin #14 (SEQ ID NO: 75 with a His-tag (SEQ ID NO: 6) fused to its N-terminus);
DARPin #15 (SEQ ID NO: 76 with a His-tag (SEQ ID NO: 6) fused to its N-terminus);
DARPin #16 (SEQ ID NO: 77 with a His-tag (SEQ ID NO: 6) fused to its N-terminus);
DARPin #17 (SEQ ID NO: 78 with a His-tag (SEQ ID NO: 6) fused to its N-terminus);
DARPin #18 (SEQ ID NO: 79 with a His-tag (SEQ ID NO: 6) fused to its N-terminus);
DARPin #19 (SEQ ID NO: 80 with a His-tag (SEQ ID NO: 6) fused to its N-terminus);
DARPin #20 (SEQ ID NO: 81 with a His-tag (SEQ ID NO: 6) fused to its N-terminus);
DARPin #21 (SEQ ID NO: 82 with a His-tag (SEQ ID NO: 6) fused to its N-terminus);
DARPin #50 (SEQ ID NO: 111 with a His-tag (SEQ ID NO: 6) fused to its N-terminus).
DARPin #51 (SEQ ID NO: 112 with a His-tag (SEQ ID NO: 6) fused to its N-terminus);
DARPin #52 (SEQ ID NO: 113 with a His-tag (SEQ ID NO: 6) fused to its N-terminus);
DARPin #53 (SEQ ID NO: 114 with a His-tag (SEQ ID NO: 6) fused to its N-terminus);
DARPin #54 (SEQ ID NO: 115 with a His-tag (SEQ ID NO: 6) fused to its N-terminus);
DARPin #55 (SEQ ID NO: 116 with a His-tag (SEQ ID NO: 6) fused to its N-terminus);
DARPin #56 (SEQ ID NO: 117 with a His-tag (SEQ ID NO: 6) fused to its N-terminus);
DARPin #57 (SEQ ID NO: 118 with a His-tag (SEQ ID NO: 6) fused to its N-terminus);
DARPin #58 (SEQ ID NO: 119 with a His-tag (SEQ ID NO: 6) fused to its N-terminus);
DARPin #59 (SEQ ID NO: 120 with a His-tag (SEQ ID NO: 6) fused to its N-terminus);
DARPin #60 (SEQ ID NO: 121 with a His-tag (SEQ ID NO: 6) fused to its N-terminus);

Examples of amino acid sequences of selected biparatopic ankyrin repeat proteins are provided in SEQ ID NO: 83 to 110, 122, 123, and 136 to 141. These biparatopic DARPins were cloned into a pQE (QIAgen, Germany) based expression vector providing an N-terminal His-tag to facilitate simple protein purification as described below. Thus, expression vectors encoding the following DARPins were constructed:

DARPin #22 (SEQ ID NO: 83 with a His-tag (SEQ ID NO: 6) fused to its N-terminus);
DARPin #23 (SEQ ID NO: 84 with a His-tag (SEQ ID NO: 6) fused to its N-terminus);
DARPin #24 (SEQ ID NO: 85 with a His-tag (SEQ ID NO: 6) fused to its N-terminus);
DARPin #25 (SEQ ID NO: 86 with a His-tag (SEQ ID NO: 6) fused to its N-terminus);
DARPin #26 (SEQ ID NO: 87 with a His-tag (SEQ ID NO: 6) fused to its N-terminus);
DARPin #27 (SEQ ID NO: 88 with a His-tag (SEQ ID NO: 6) fused to its N-terminus);
DARPin #28 (SEQ ID NO: 89 with a His-tag (SEQ ID NO: 6) fused to its N-terminus);
DARPin #29 (SEQ ID NO: 90 with a His-tag (SEQ ID NO: 6) fused to its N-terminus);

DARPin #30 (SEQ ID NO: 91 with a His-tag (SEQ ID NO: 6) fused to its N-terminus);
DARPin #31 (SEQ ID NO: 92 with a His-tag (SEQ ID NO: 6) fused to its N-terminus);
DARPin #32 (SEQ ID NO: 93 with a His-tag (SEQ ID NO: 6) fused to its N-terminus);
DARPin #33 (SEQ ID NO: 94 with a His-tag (SEQ ID NO: 6) fused to its N-terminus);
DARPin #34 (SEQ ID NO: 95 with a His-tag (SEQ ID NO: 6) fused to its N-terminus);
DARPin #35 (SEQ ID NO: 96 with a His-tag (SEQ ID NO: 6) fused to its N-terminus);
DARPin #36 (SEQ ID NO: 97 with a His-tag (SEQ ID NO: 6) fused to its N-terminus);
DARPin #37 (SEQ ID NO: 98 with a His-tag (SEQ ID NO: 6) fused to its N-terminus);
DARPin #38 (SEQ ID NO: 99 with a His-tag (SEQ ID NO: 6) fused to its N-terminus);
DARPin #39 (SEQ ID NO: 100 with a His-tag (SEQ ID NO: 6) fused to its N-terminus);
DARPin #40 (SEQ ID NO: 101 with a His-tag (SEQ ID NO: 6) fused to its N-terminus);
DARPin #41 (SEQ ID NO: 102 with a His-tag (SEQ ID NO: 6) fused to its N-terminus);
DARPin #42 (SEQ ID NO: 103 with a His-tag (SEQ ID NO: 6) fused to its N-terminus);
DARPin #43 (SEQ ID NO: 104 with a His-tag (SEQ ID NO: 6) fused to its N-terminus);
DARPin #44 (SEQ ID NO: 105 with a His-tag (SEQ ID NO: 6) fused to its N-terminus);
DARPin #45 (SEQ ID NO: 106 with a His-tag (SEQ ID NO: 6) fused to its N-terminus);
DARPin #46 (SEQ ID NO: 107 with a His-tag (SEQ ID NO: 6) fused to its N-terminus);
DARPin #47 (SEQ ID NO: 108 with a His-tag (SEQ ID NO: 6) fused to its N-terminus);
DARPin #48 (SEQ ID NO: 109 with a His-tag (SEQ ID NO: 6) fused to its N-terminus);
DARPin #49 (SEQ ID NO: 110 with a His-tag (SEQ ID NO: 6) fused to its N-terminus)
DARPin #61 (SEQ ID NO: 122 with a His-tag (SEQ ID NO: 6) fused to its N-terminus);
DARPin #62 (SEQ ID NO: 123 with a His-tag (SEQ ID NO: 6) fused to its N-terminus);
DARPin #63 (SEQ ID NO: 136 with a His-tag (SEQ ID NO: 6) fused to its N-terminus);
DARPin #64 (SEQ ID NO: 137 with a His-tag (SEQ ID NO: 6) fused to its N-terminus);
DARPin #65 (SEQ ID NO: 138 with a His-tag (SEQ ID NO: 6) fused to its N-terminus);
DARPin #66 (SEQ ID NO: 139 with a His-tag (SEQ ID NO: 6) fused to its N-terminus);
DARPin #67 (SEQ ID NO: 140 with a His-tag (SEQ ID NO: 6) fused to its N-terminus);
DARPin #68 (SEQ ID NO: 141 with a His-tag (SEQ ID NO: 6) fused to its N-terminus).

High Level and Soluble Expression of Monovalent DARPins

For further analysis, DARPins #1 to 50 were expressed in E. coli BL21 or XL1-Blue cells and purified using their His-tag using standard protocols. 25 ml of stationary overnight cultures (LB, 1% glucose, 100 mg/l of ampicillin; 37° C.) were used to inoculate 1 l cultures (same medium). At an absorbance of 0.7 at 600 nm, the cultures were induced with 0.5 mM IPTG and incubated at 37° C. for 4-5 h. The cultures were centrifuged and the resulting pellets were resuspended in 40 ml of TBS500 (50 mM Tris-HCl, 500 mM NaCl, pH 8) and sonicated. The lysate was recentrifuged, and glycerol (10% (v/v) final concentration) and imidazole (20 mM final concentration) were added to the resulting supernatant. Proteins were purified over a Ni-nitrilotriacetic acid column (2.5 ml column volume) according to the manufacturer's instructions (QIAgen, Germany). Alternatively, DARPins or selected repeat domains devoid of a 6xHis-tag were purified by anion exchange chromatography followed by size exclusion chromatography according to standard resins and protocols known to the person skilled in the art. Up to 200 mg of highly soluble DARPins with binding specificity to HER2 can be purified from one liter of E. coli culture with a purity>95% as estimated from SDS-15% PAGE. Such purified DARPins are used for further characterizations.

Example 2: Characterization of the DARPins with Binding for Specificity for HER2 by Surface Plasmon Resonance Analysis Protein binding kinetics of interesting purified HER2-binding DARPins were assayed by Surface Plasmon Resonance (SPR) analysis with a ProteOn array system (BioRad) using a setup, where biotinylated human HER2 was immobilized via neutravidin and the interaction was measured by adding free monovalent DARPin. The determination of Kd values was performed according to standard procedures.

Biotinylated ectodomain of human HER2 molecule was immobilized in a flow cell through binding to coated Streptavidin and the interaction with various selected DARPins was analyzed.

Surface Plasmon Resonance (SPR) Analysis

SPR was measured using a ProteOn instrument (BioRad) and measurement was performed according standard procedures known to the person skilled in the art. The running buffer was PBS, pH 7.4, containing 0.005% Tween 20®. Neutravidin was covalently immobilized on a GLC chip (BioRad) to a level of about 8000 resonance units (RU). Immobilization of HER2 on the neutravidin coated chip was then performed. The interaction of DARPin HER2 was then measured by injecting 100 µl running buffer (PBS containing 0.005% Tween®) containing serial dilutions of DARPins of concentration of 50, 25, 12.5, 6.25 and 3.125 nM (on-rate measurement), followed by a running buffer flow for between 10 minutes and up to 3 hours at a constant flow rate of 100 µl/min (off-rate measurement). The signals (i.e. resonance unit (RU) values) of an uncoated reference cell and a reference injection (i.e. injection of running buffer only) were subtracted from the RU traces obtained after injection of HER2 (double-referencing). From the SRP traces obtained from the on-rate and off-rate measurements the on- and off-rate of the corresponding DARPin HER2 interaction can be determined.

The results are summarized in Table 1. Dissociation constants (Kd) were calculated from the estimated on- and off-rates using standard procedures known to the person skilled in the art.

TABLE 1

Dissociation constants of selected DARPins for human HER2 as determined by SPR

| DARPin # | Kd [M] |
|---|---|
| 1 | 7.81E−11 |
| 2 | 8.75E−10 |
| 3 | 1.31E−11 |
| 4 | 1.86E−10 |

TABLE 1-continued

Dissociation constants of selected DARPins
for human HER2 as determined by SPR

| DARPin # | Kd [M] |
|---|---|
| 5 | 7.08E−11 |
| 6 | 2.92E−11 |
| 7 | 1.03E−09 |
| 8 | 4.83E−10 |
| 9 | 4.17E−10 |
| 10 | 1.03E−09 |
| 11 | 2.56E−10 |
| 12 | 1.41E−09 |
| 13 | n.d. |
| 14 | 1.88E−09 |
| 15 | 4.68E−10 |
| 16 | 2.67E−09 |
| 17 | 2.30E−09 |
| 18 | 3.35E−10 |
| 19 | 9.44E−10 |
| 20 | 2.58E−10 |
| 21 | 1.65E−09 |
| 51 | 1.3E−09 |
| 52 | 1.37E−10 |
| 53 | 1.46E−09 |
| 54 | 9.27E−12 |
| 55 | 8.73E−11 |
| 56 | 2.00E−09 |
| 57 | 6.04E−11 |
| 58 | 4.13E−11 |
| 59 | 3.33E−11 |
| 60 | 1.17E−11 | n.d.: not determined.

Example 3: Mapping Repeat Domain Binding to Specific Extracellular HER2 Epitopes The interaction of the repeat domains with the extracellular HER2 domains was analyzed by standard methods known to the person skilled in the art, such as quaternary structure analysis of the complexes by X-ray crystallography or NMR spectroscopy, or epitope mapping by using alanine mutagenesis of potential interaction residues or by using mass spectrometry and covalent tagging. Furthermore, various competition assays, such as competition enzyme-linked immunosorbent assays (ELISAs) know to the practitioner in the art were performed to identify the extracellular domains to which selected repeat protein bind or if they have overlapping epitopes on the extracellular domains of HER2 with other binding proteins, for example antibodies such as trastuzumab or pertuzumab.

The extracellular domains of HER2 were either purchased or produced as described (Jost et. al., loc. cit.)

Competition of interesting purified HER2-binding DARPins was performed by Surface Plasmon Resonance (SPR) analysis with a ProteOn array system (BioRad) using a setup, where biotinylated human ErbB2 S22-N530 and ErbB2 S22-E645 was immobilized via neutravidin and the competition was measured by adding the first monovalent DARPin at saturation (1 uM), followed by a 1:1 mixture of the first and the second DARPin (100 nM each). If the second DARPin bound, despite the presence of the first DARPin, the second DARPin was considered to bind a different epitope.

For example, competition ELISA (FIGS. 1A and 1B) data suggest that DARPin #54 binds to domain II in Her2 and DARPin #51 binds to domain I of HER2. Previously it was shown that DARPin #18 binds to domain IV of HER2 (Jost et al., loc. cit.). The DARPins (20 nM) were preincubated with HER2 domain I, domain I-III or domain III-IV (in each case at a domain concentration of 500 nM) in PBS for 45 min at room temperature. The mixture was added to 20 nM of full length Her2 coated on a F96 MaxiSorb Nunc (Cat. 442404) plate. Bound DARPins were specifically detected using a monoclonal mouse anti RGS-His antibody (Qiagen Cat.34650) as primary antibody and an anti-mouse antibody labeled with horse radish peroxidase (Pierce, Cat.31438) as secondary antibody. The primary antibody (mouse anti RGS-His antibody) was replaced by a monoclonal mouse anti-DARPin antibody for the ELISA depicted in FIG. 1B.

The read out was made at 450 nm. All the incubations steps were performed in PBS at pH 7.4 containing 0.1% Tween 20® and 0.25% Casein at room temperature for 2 h on a Heidolph Titramax 1000 shaker at 450 rpm except the plate coating, which was performed over-night at 4° C. using PBS at pH 7.4.

These findings were confirmed by competing binding of these DARPins to Her2 overexpressing cells (BT474) with recombinant domain I, domain I-II-III and domain III-IV of Her2 by Flow Cytometry (FACS). DARPins (100 nM) were preincubated with the individual Her2 constructs (1 uM) at 25° C. for 30 minutes. The mixture was applied to cells (100.000 cells in 100 ul) for 20 minutes on ice. DARPin binding to cells was monitored using an Alexa 647 labeled anti-Penta-His antibody (Qiagen Cat. No: 35370). The analyses confirmed the binding of DARPin #51 to domain I of HER2 and DARPin #1 to domain II in HER2 and DARPin#18 to domain IV of HER2.

Competition of DARPin #1 with pertuzumab and DARPin #18 with trastuzumab was also tested using Flow Cyotmetry. To this end BT474 cells were preincubated with pertuzumab, respectively trastuzumab (both 1 uM) before incubation with the respective DARPin (1 uM). Binding of DARPin to the cells was monitored using an Alexa 647 labeled anti-Penta-His antibody (Qiagen Cat. No: 35370) and binding of pertuzumab or trastuzumab was monitored using an Alexa 546 labeled anti-human-IgG antibody (Invitrogen Cat. No: A-21089). The experiment showed that none of the DARPins competes with binding of pertuzumab or trastuzumab to HER2 expressed by BT474 cells.

This finding was also observed by ELISA (FIG. 1C), where pertuzumab (coated on a F96 MaxiSorb Nunc (Cat. 442404) at 20 nM) was preincubated with 20 nM Her2 (domain 1-1111) before incubation with the respective DARPins (20 nM). The specific binding of the DARPin on the Her2-Pertuzumab complex was detected using a monoclonal mouse anti RGS-His antibody (Qiagen, Cat.34650) and an anti-mouse antibody labeled with horse radish peroxidase (Pierce, Cat.31438) (premixed for 45 min at room temperature). All the incubations steps were performed at room temperature for 2 h on a Heidolph Titramax 1000 shaker at 450 rpm except the plate coating, performed over-night at 4° C. PBS, 0.1% Tween 20® pH7.4, 0.25% Casein was used a blocking agent. All the N-terminal DARPins tested in this assay (DARPin #7, DARPin #52, DARPin #53, and DARPin #54) are binding Her2 in presence of pertuzumab, showing that they all bind a different epitope than the antibody.

Overall such experiments showed that the monovalent repeat domains encoded by SEQ ID NO: 62 to 68, 72, and 114 to 121_bind to domain II of HER2, the monovalent repeat domains encoded by SEQ ID NO: 69-71, 73, 112 and 113 bind to domain I of HER2 and the monovalent repeat domains encoded by SEQ ID NO: 74 to 82 bind to domain IV of HER2. None of the monovalent repeat domains binding to domain II of HER2 (SEQ ID NO: 62 to 68, 72, and 114 to 121 compete with pertuzumab on binding to HER2. Among the monovalent repeat domain binding to domain IV of HER2, the repeat domains encoded by the SEQ ID NO: 77, 78 and 82 compete with trastuzumab for binding to HER2 whereas the repeat domains encoded by the SEC ID NO: 74 to 76 and 79 to 81 do not compete with trastuzumab.

Example 4: Biparatopic Her2-Binding DARPins Block Growth of Her2-Overexpressing Tumor Cells Monovalent DARPins, mixtures of DARPins and biparatopic Her2-binding DARPins were tested for inhibition of BT474 cell proliferation. FIG. 2 shows that monovalent DARPins and mixtures of monovalent DARPins are not capable to block BT474 proliferation. In contrast, a subset of biparatopic DARPins induce proliferation inhibition (FIG. 2, and Table 2). Interestingly, DARPins repeat domain IV of HER2 have to be located at the C-terminus of the molecule (FIG. 2). Multiple combinations of monovalent DARPins in a biparatopic format resulted in proliferation inhibiting biparatopic DARPins. However, not all combinations are capable to block BT474 proliferation to 90-100% (FIG. 3), which allows ranking of certain DARPin combinations. These findings indicate that targeting a distinct subset of certain epitopes in HER2 in a biparatopic format is key for achieving potency. Induction of HER2 receptor internalization and degradation as reported by trastuzumab is not sufficient to induce potent inhibition of tumour cell proliferation (FIGS. 3 and 5). Both DARPin #41 and DARPin #43 induce degradation of Her2 similar to trastuzumab, but only DARPins such as DARPin #41 inhibits tumour cell proliferation.

Experiments were performed as described in the Methods section. Example results are summarized in Table 2. $IC_{50}$ values were calculated from the titration curves obtained as described above using standard procedures known to the person skilled in the art. Example titration curves are given for DARPin #41 in FIGS. 2 and 3.

TABLE 2

Inhibition potency by various DARPins of BTB474 cell proliferation

| DARPin # or antibody | IC50 [nM] | % activity vs. DARPin # 41 |
|---|---|---|
| 32 | 3.29 | 48.0 |
| 22 | 4.03 | 60.1 |
| 27 | 4.57 | 37.8 |
| 35 | 4.63 | 63.0 |
| 38 | 3.30 | 99.3 |
| 33 | 4.47 | 65.3 |
| 23 | 2.99 | 97.3 |
| 28 | 5.15 | 82.5 |
| 36 | 2.56 | 68.8 |
| 34 | 3.88 | 95.1 |
| 24 | 1.97 | 99.9 |
| 29 | 1.33 | 95.0 |
| 37 | 2.19 | 94.8 |
| 40 | 2.76 | 91.2 |
| 42 | 3.77 | 100 |
| 45 | 1.55 | 100 |
| 46 | 3.34 | 100 |
| 41 | 4.01 | 100 |
| 47 | n.i. | 6.8 |
| 43 | n.i. | n.i. |
| 44 | n.i. | n.i. |
| 48 | n.i. | n.i. |
| 49 | n.i. | n.i |
| 21 | n.i. | n.i. |
| 12 | n.i. | n.i. |

TABLE 2-continued

Inhibition potency by various DARPins of BTB474 cell proliferation

| DARPin # or antibody | IC50 [nM] | % activity vs. DARPin # 41 |
|---|---|---|
| 1 | n.i. | n.i. |
| 18 | n.i. | n.i. |
| 64 | 2.31 | 100 |
| 65 | 4.07 | 100 |
| 63 | 1.77 | 100 |
| 68 | 5.35 | 100 |
| 67 | 4.87 | 100 |
| 66 | 4.06 | 100 |
| 64 | 2.31 | 100 |
| trastuzumab | 3.05 | 52 |
| pertuzumab | n.i | n.i | n.i.: no inhibition observed

Example 5: Biparatopic Her2-Targeting DARPins Inhibit Proliferation of Various Her2 Overexpressing Cell Lines and Induces Apoptosis The potency of the biparatopic DARPin #41 was tested The DARPin inhibited proliferation in cell lines overexpressing Her2 in the range from Her2 IHC 3+ to 1+ and not in cells expressing wild type HER2 levels (FIG. 4; Table 3). Moreover the DARPin induces robustly apoptosis within 24 h of incubation in the listed cell lines (FIG. 5, Table 3).

Experiments were performed as described in the Methods section. Example results are summarized in Table 3. $IC_{50}$ and $EC_{50}$ values were calculated from the titration curves obtained as described above using standard procedures known to the person skilled in the art. Example titration curves are given for DARPin #41 on three different cell lines in FIGS. 4 and 5. The IC50 and EC50 values ranges between 0.2-10 nM, depending on the tested DARPin and the cell line. For example, it was shown that DARPin #41, #45 and #46 induce apoptosis in BT474, MDA-MB175 and NCI-N87 cells (Table 3). Similar results were obtained using other biparatopic binding proteins of the inventions.

TABLE 3

Potency of DARPin #41 on various different cell lines

| Cell line | Her2 status | Inhibition of proliferation IC50 [nM] | Induction of apoptosis EC50 [nM] |
|---|---|---|---|
| BT474 | IHC 3+ | 0.98 | 0.69 |
| SKBR-3 | IHC 3+ | 1.75 | n.a. |
| NCI-N87 | IHC 2+ | 0.94 | 0.26 |
| ZR75-30 | IHC 3+ | 0.60 | n.a. |
| HCC1419 | IHC 3+ | 3.17 | n.a. |
| MDA-MB175 | IHC 1+ | 3.42 | 5.94 |
| MCF7 | IHC 0/wt | n.i. | n.i. | n.a.: not analyzed
n.i.: no inhibition

Example 6: Biparatopic Her2-Targeting DARPins Inhibit Proliferation and Induces Apoptosis in BT474 Cells in Contrast to the Current Standard of Care Therapies The potency of the biparatopic DARPin #41 was compared to drugs approved for the treatment of Her2 positive breast cancers, trastuzumab and pertuzumab. The DARPin efficiently inhibits proliferation and is inducing apoptosis in contrast to trastuzumab, Pertuzumab or a combination of trastuzumab and pertuzumab (FIG. 6).

Experiments were performed as described in the Methods section. Example results are shown in FIG. 6. $IC_{50}$ and $EC_{50}$ values (Table 3) were calculated from the titration curves obtained as described above using standard procedures known to the person skilled in the art. Similar results were obtained using other biparatopic binding proteins of the inventions.

Example 7: Generation of Various DARPin Formats

Figure 7A:
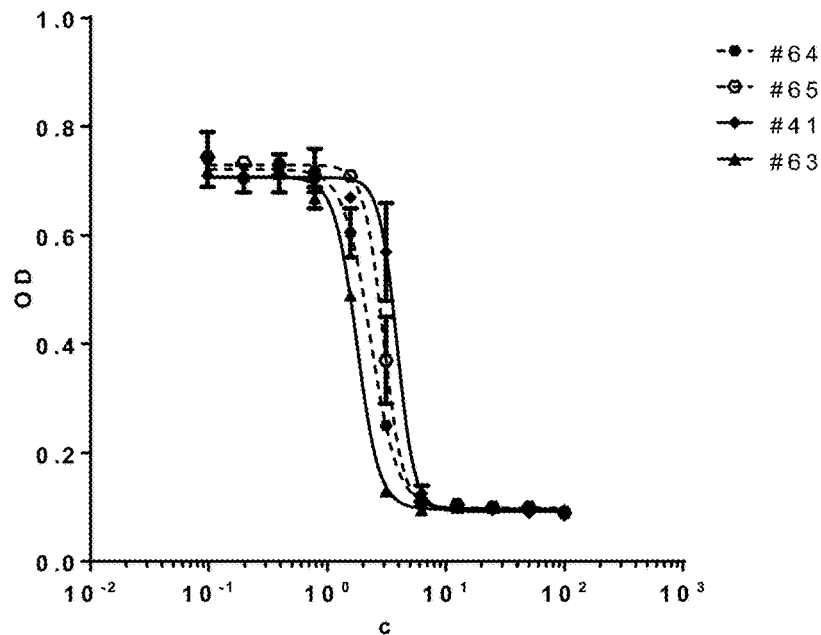
FIG. 7A shows the inhibition of proliferation by various concentrations of biparatopic DARPins, which were engineered to have a long serum half live, and the corresponding fitted inhibition curves are shown for a distinct single experiment. The biparatopic DARPin #63 is PEGylated at its C-terminal Cys residue, whereas the biparatopic DARPins #64 and #65 comprise an ankyrin repeat domain binding to serum albumin.
Figure 7B:
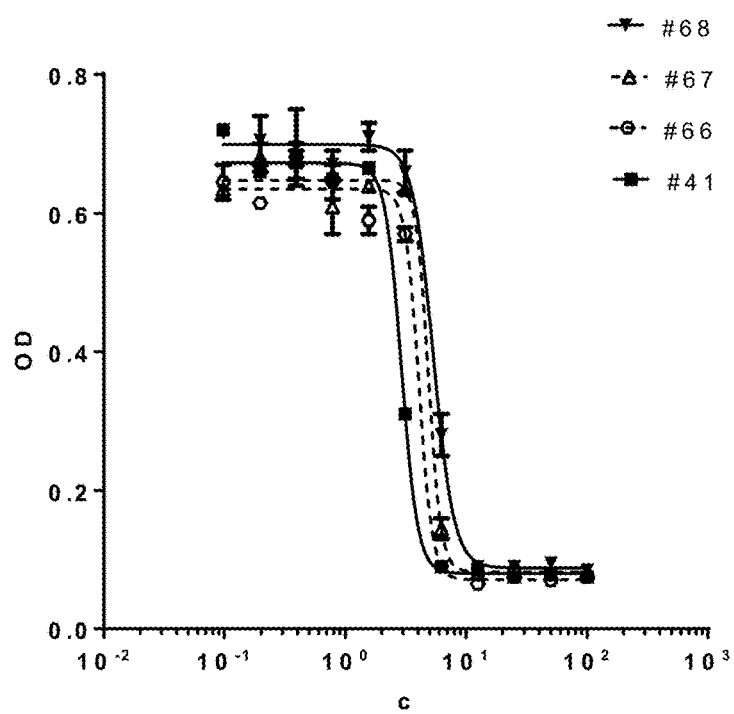
FIG. 7B shows the inhibition of proliferation by various concentrations of biparatopic DARPins comprising different linkers between the repeat domains binding HER2 and the corresponding fitted inhibition curves are shown for a distinct single experiment. The IC50 values for DARPins are listed in Table 2. Graph shows OD, optical density at 450 nm minus OD at 620 nm plotted against C, concentration of DARPins in nM. The X axis is shown in logarithmic scale. See below for the definitions of the DARPins. #66, DARPin #66, which comprises a short two amino acid long GS-linker between the two repeat domains; #67, DARPin #67, which comprises a five amino acid long GS-linker between the two repeat domains; #41, DARPin #41, which comprises a ten amino acid long GS-linker between the two repeat domains; #68, DARPin #68, which comprises a 24 amino acid long PT-linker between the two repeat domains. DARPin #1 is SEQ ID NO:62 with a His-tag (SEQ ID NO:6) fused to its N-terminus. DARPin #41 is SEQ ID NO:102 with a His-tag (SEQ ID NO:6) fused to its N-terminus. DARPin #63 is SEQ ID NO:136 with a His-tag (SEQ ID NO:6) fused to its N-terminus. DARPin #64 is SEQ ID NO:137 with a His-tag (SEQ ID NO:6) fused to its N-terminus. DARPin #65 is SEQ ID NO:138 with a His-tag (SEQ ID NO:6) fused to its N-terminus. DARPin #66 is SEQ ID NO:139 with a His-tag (SEQ ID NO: 6) fused to its N-terminus. DARPin #67 is SEQ ID NO:140 with a His-tag (SEQ ID NO: 6) fused to its N-terminus. DARPin #68 is SEQ ID NO:141 with a His-tag (SEQ ID NO: 6) fused to its N-terminus.

As an example, the potency of different formats of the biparatopic DARPin #41 were compared to DARPin #41 in inhibition of BT474 cell proliferation (FIG. 7, Table 2). PEGylation or fusion to a human serum albumin binding DARPin (DARPin #41, #63, #64, #65) to the N- or C-terminus did not affect potency (FIG. 7A). Moreover variation of the linkers between the DARPin moieties did not affect potency (FIG. 7B). The 1050 values range between 1.5-5.5 nM. Corresponding results were obtained using corresponding formats of the biparatopic DARPins #41, #66, #67, #68 was obtained. Overall, this clearly suggests that the biparatopic DARPins can be modified (by methods known to the person skilled in the art, such as PEGylation or fusion to serum albumin binding domains) to increase their in vivo half-life without the loss of potency. Furthermore, these experiments suggest that the linker between the two repeat domains binding to HER2 in a biparatopic construct can be varied at least from two to 24 amino acids without significantly influencing the efficacy of the biparatopic construct.

Example 8: DARPin/Her2 Interaction Mapping

The interaction of the biparatopic DARPins of the inventions with the HER2 ectodomain was further analyzed by chemical crosslinking of the complex formed by these two molecules in solution (i.e. in PBS pH 7.4), followed by a digest of the complex with a protease, and analysis of the resulting peptides by mass spectroscopy. In such an experiment regions of the DARPin can be covalently crosslinked to regions of HER2 only if they are in close proximity to the latter. The detection of peptides from the DARPin that are covalently crosslinked to a corresponding peptide of HER2 by such a mass spectroscopy analysis indicates that those peptides are in close proximity in the HER2/DRAPin complex. Such proximity analysis methods are well known to the person skilled in the art (e.g., Birch, C., et al., Anal. Chem., 82, 172-179, 2010) and are offered by various companies as a service (e.g., CovalX AG, Zurich, Switzerland).

For example, in such experiments it was found that the biparatopic DARPin #41, which binds domain II and domain IV of HER2, can form a 1 to 1 complex with HER2. Surprisingly, covalent crosslinks between the C-terminal repeat domain (binding to domain IV of HER2) and domain I of HER2 were observed, indicating close proximity of this repeat domain with domain I of HER2 in the complex, even though it binds to domain IV. Such crosslinks would not be expected to be seen if HER2 would be in a conformation as described in the prior art (e.g., Bublil and Yarden, loc. cit). Importantly, when the HER2 ectodomain was analyzed in complex with this C-terminal repeat domain binding to domain IV alone then no such crosslinks to domain I of HER2 could be observed, indicating that in the case of the complex formed by HER2 and the monomeric repeat domain binding to domain IV, no proximity of this repeat domain to domain I exists. Thus, the three dimensional domain arrangements for HER2 must be different in the complex formed with the biparatopic binding protein of the invention compared to the complex formed with the individual repeat domain binding domain IV of HER2.

Interestingly, the known structures of the ectodomain of HER2 would not allow the simultaneous binding of both repeat domains of a biparatopic binding protein of the invention to the same HER2 molecule, when considering the short linkers in the range of 2 to 24 amino acids between two repeat domains. This indicates that HER2 may be in a yet unknown conformation allowing the simultaneous binding of both repeat domains.

Overall, such experiments indicate that the biparatopic binding proteins of the invention may be able to intramolecularly interact with the ectodomain of HER2, and that they thereby fix the HER2 ectodomain in a novel conformation not known in the prior art, namely by bringing domain I and domain IV in a steric arrangement that allows the observed crosslink between the repeat domain (binding to domain IV of HER2) and domain I to occur. Thus, this novel conformation of HER2 seems to be stabilized by a biparatopic binding protein of the invention by simultaneously binding domain II and domain IV of HER2 in an intramolecular manner.

What is claimed is:

1. A recombinant protein comprising at least a first and a second ankyrin repeat domain, wherein each of said first and second ankyrin repeat domains binds the extracellular region of human epidermal growth factor receptor 2 (HER2), wherein said first ankyrin repeat domain binds domain II of HER2 and said second ankyrin repeat domain binds domain IV of HER2, wherein said first and second ankyrin repeat domains are located on the same polypeptide and wherein said first ankyrin repeat domain is located N-terminally to said second ankyrin repeat domain, and wherein
   a) said first ankyrin repeat domain comprises an amino acid sequence that has at least 91% amino acid sequence identity with an ankyrin repeat domain selected from the group consisting of SEQ ID NOs:62 to 68, 72, and 114 to 121, and
   b) said second ankyrin repeat domain comprises an amino acid sequence that has at least 91% amino acid sequence identity with an ankyrin repeat domain selected from the group consisting of SEQ ID NOs:74 to 82.

2. The recombinant protein of claim 1, wherein said first ankyrin repeat domain does not compete for binding to HER2 with pertuzumab.

3. The recombinant protein of claim 1, wherein said second ankyrin repeat domain does not compete for binding to HER2 with trastuzumab.

4. The recombinant protein of claim 1, wherein
   a) said first ankyrin repeat domain comprises an amino acid sequence that has at least 95% amino acid sequence identity with an ankyrin repeat domain selected from the group consisting of SEQ ID NOs:62 to 68, 72, and 114 to 121, and
   b) said second ankyrin repeat domain comprises an amino acid sequence that has at least 95% amino acid sequence identity with an ankyrin repeat domain selected from the group consisting of SEQ ID NOs:74 to 82.

5. The recombinant protein of claim 1, wherein said first ankyrin repeat domain binds the extracellular region of HER2 in PBS with a $K_d$ below $10^{-7}$M and said second ankyrin repeat domain binds the extracellular region of HER2 in PBS with a $K_d$ below $10^{-7}$M.

6. The recombinant protein of claim 1, wherein said protein inhibits stimulated proliferation of BT474 cells with an $IC_{50}$ value below 100 nM.

7. The recombinant protein of claim 1, wherein said protein induces apoptosis in BT474 cells with an $EC_{50}$ value below 100 nM.

8. The recombinant protein of claim 1, wherein said first and second ankyrin repeat domains are connected by a polypeptide linker.

9. The recombinant protein of claim 1, wherein
   a) said first ankyrin repeat domain comprises an amino acid sequence that has at least 98% amino acid sequence identity with an ankyrin repeat domain selected from the group consisting of SEQ ID NOs:62 to 68, 72, and 114 to 121, and
   b) said second ankyrin repeat domain comprises an amino acid sequence that has at least 98% amino acid sequence identity with an ankyrin repeat domain selected from the group consisting of SEQ ID NOs:74 to 82.

10. The recombinant protein of claim 1, wherein
a) said first ankyrin repeat domain is selected from the group consisting of SEQ ID NOs:62 to 68, 72, and 114 to 121, and
b) said second ankyrin repeat domain is selected from the group consisting of SEQ ID NOs:74 to 82, and wherein further
a) G at position 1 and/or S at position 2 of said ankyrin repeat domains are optionally missing; and
b) L at the second last position and/or N at the last position of said ankyrin repeat domains are optionally substituted with A.

11. A recombinant protein comprising at least a first and a second ankyrin repeat domain, wherein each of said two repeat domains binds the extracellular region of human epidermal growth factor receptor 2 (HER2), wherein said repeat domains are covalently linked, and wherein said recombinant protein comprises a polypeptide, wherein said polypeptide has at least 90% amino acid sequence identity with a polypeptide selected from the group consisting of SEQ ID NO:83 to 98, 102, 103, 122, 123, and 136 to 141.

12. A pharmaceutical formulation comprising a recombinant protein of claim 1 and a pharmaceutically acceptable carrier.

13. The recombinant protein of claim 11, wherein said first repeat domain binds domain II of HER2 and said second repeat domain binds domain IV of HER2, wherein said first and second repeat domains are located on the same polypeptide, and wherein said first repeat domain is located N-terminally to said second repeat domain.

14. The recombinant protein of claim 11, wherein said protein induces apoptosis in BT474 cells with an $EC_{50}$ value below 100 nM.

15. The recombinant protein of claim 11, wherein said polypeptide has at least 95% amino acid sequence identity with a polypeptide selected from the group consisting of SEQ ID NO:83 to 98, 102, 103, 122, 123, and 136 to 141.

16. The recombinant protein of claim 11, wherein said polypeptide has at least 98% amino acid sequence identity with a polypeptide selected from the group consisting of SEQ ID NO:83 to 98, 102, 103, 122, 123, and 136 to 141.

17. A pharmaceutical formulation comprising the recombinant protein of claim 11 and a pharmaceutically acceptable carrier.

18. A recombinant protein comprising at least a first and a second ankyrin repeat domain, wherein each of said two repeat domains binds the extracellular region of human epidermal growth factor receptor 2 (HER2), wherein said repeat domains are covalently linked, and wherein said recombinant protein comprises a polypeptide, wherein said polypeptide comprises said first and second ankyrin repeat domains and has at least 90% amino acid sequence identity with SEQ ID NO: 87.

19. The recombinant protein of claim 18, wherein said polypeptide has at least 95% amino acid sequence identity with SEQ ID NO: 87.

20. The recombinant protein of claim 18, wherein said polypeptide has the amino acid sequence of SEQ ID NO: 87.

21. The recombinant protein of claim 18, wherein said protein induces apoptosis in BT474 cells with an $EC_{50}$ value below 100 nM.

22. A pharmaceutical formulation comprising the recombinant protein of claim 18 and a pharmaceutically acceptable carrier.

23. A nucleic acid encoding the recombinant protein of claim 1.

* * * * *

SEQUENCE LISTING

```
<160> NUMBER OF SEQ ID NOS: 141

<210> SEQ ID NO 1
<211> LENGTH: 126
<212> TYPE: PRT
<213> ORGANISM: Artificial
<220> FEATURE:
<223> OTHER INFORMATION: Capping module

<400> SEQUENCE: 1

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Lys Asp Gly Tyr Thr Pro Leu His Leu Ala Ala Arg Glu Gly
        35                  40                  45
```

His Leu Glu Ile Val Glu Val Leu Leu Lys Ala Gly Ala Asp Val Asn
        50                  55                  60

Ala Lys Asp Lys Asp Gly Tyr Thr Pro Leu His Leu Ala Arg Glu
65                  70                  75                  80

Gly His Leu Glu Ile Val Glu Val Leu Leu Lys Ala Gly Ala Asp Val
                85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Leu Asn
            115                 120                 125

<210> SEQ ID NO 2
<211> LENGTH: 32
<212> TYPE: PRT
<213> ORGANISM: Artificial
<220> FEATURE:
<223> OTHER INFORMATION: Capping module

<400> SEQUENCE: 2

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
                20                  25                  30

<210> SEQ ID NO 3
<211> LENGTH: 32
<212> TYPE: PRT
<213> ORGANISM: Artificial
<220> FEATURE:
<223> OTHER INFORMATION: Capping module

<400> SEQUENCE: 3

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
                20                  25                  30

<210> SEQ ID NO 4
<211> LENGTH: 28
<212> TYPE: PRT
<213> ORGANISM: Artificial
<220> FEATURE:
<223> OTHER INFORMATION: Capping module

<400> SEQUENCE: 4

Gln Asp Lys Phe Gly Lys Thr Ala Phe Asp Ile Ser Ile Asp Asn Gly
1               5                   10                  15

Asn Glu Asp Leu Ala Glu Ile Leu Gln Lys Leu Asn
                20                  25

<210> SEQ ID NO 5
<211> LENGTH: 28
<212> TYPE: PRT
<213> ORGANISM: Artificial
<220> FEATURE:
<223> OTHER INFORMATION: Capping module

<400> SEQUENCE: 5

Gln Asp Lys Ser Gly Lys Thr Pro Ala Asp Leu Ala Ala Asp Ala Gly
1               5                   10                  15

His Glu Asp Ile Ala Glu Val Leu Gln Lys Leu Asn
                20                  25

```
<210> SEQ ID NO 6
<211> LENGTH: 10
<212> TYPE: PRT
<213> ORGANISM: Artificial
<220> FEATURE:
<223> OTHER INFORMATION: His-tag

<400> SEQUENCE: 6

Met Arg Gly Ser His His His His His His
1               5                   10

<210> SEQ ID NO 7
<211> LENGTH: 2
<212> TYPE: PRT
<213> ORGANISM: Artificial
<220> FEATURE:
<223> OTHER INFORMATION: GS-linker

<400> SEQUENCE: 7

Gly Ser
1

<210> SEQ ID NO 8
<211> LENGTH: 5
<212> TYPE: PRT
<213> ORGANISM: Artificial
<220> FEATURE:
<223> OTHER INFORMATION: GS-linker

<400> SEQUENCE: 8

Gly Gly Gly Gly Ser
1               5

<210> SEQ ID NO 9
<211> LENGTH: 10
<212> TYPE: PRT
<213> ORGANISM: Artificial
<220> FEATURE:
<223> OTHER INFORMATION: GS-linker

<400> SEQUENCE: 9

Gly Gly Gly Gly Ser Gly Gly Gly Gly Ser
1               5                   10

<210> SEQ ID NO 10
<211> LENGTH: 20
<212> TYPE: PRT
<213> ORGANISM: Artificial
<220> FEATURE:
<223> OTHER INFORMATION: GS-linker

<400> SEQUENCE: 10

Gly Gly Gly Gly Ser Gly Gly Gly Gly Ser Gly Gly Gly Gly Ser Gly
1               5                   10                  15

Gly Gly Gly Ser
            20

<210> SEQ ID NO 11
<211> LENGTH: 5
<212> TYPE: PRT
<213> ORGANISM: Artificial
<220> FEATURE:
<223> OTHER INFORMATION: PT-linker

<400> SEQUENCE: 11

Pro Thr Pro Thr Pro
```

```
<210> SEQ ID NO 12
<211> LENGTH: 20
<212> TYPE: PRT
<213> ORGANISM: Artificial
<220> FEATURE:
<223> OTHER INFORMATION: PT-linker

<400> SEQUENCE: 12

Pro Thr Pro Thr Pro Thr Thr Pro Thr Pro Thr Pro Thr Thr Pro Thr
1               5                   10                  15

Pro Thr Pro Thr
            20

<210> SEQ ID NO 13
<211> LENGTH: 32
<212> TYPE: PRT
<213> ORGANISM: Artificial
<220> FEATURE:
<223> OTHER INFORMATION: N-Cap module (Nr)

<400> SEQUENCE: 13

Gly Ser Asp Leu Gly Ile Lys Leu Leu Phe Ala Ala Lys Ser Gln
1               5                   10                  15

Asp Asp Glu Val Arg Ile Leu Leu Ala Ala Gly Ala Asp Val Asn Ala
            20                  25                  30

<210> SEQ ID NO 14
<211> LENGTH: 32
<212> TYPE: PRT
<213> ORGANISM: Artificial
<220> FEATURE:
<223> OTHER INFORMATION: N-Cap module (Nr)

<400> SEQUENCE: 14

Gly Ser Asp Leu Gly Val Asn Leu Leu Trp Ala Ala Thr Arg Gly Gln
1               5                   10                  15

Asp Asp Glu Val Arg Ile Leu Leu Ala Ala Gly Ala Asp Val Asn Ala
            20                  25                  30

<210> SEQ ID NO 15
<211> LENGTH: 33
<212> TYPE: PRT
<213> ORGANISM: Artificial
<220> FEATURE:
<223> OTHER INFORMATION: AR module (M1.1b)

<400> SEQUENCE: 15

Lys Asp Phe Gln Ser Val Thr Pro Leu His Ile Ala Ala Gln Ser Gly
1               5                   10                  15

His Leu Glu Ile Val Glu Val Leu Leu Lys Ala Gly Ala Asp Val Asn
            20                  25                  30

Ala

<210> SEQ ID NO 16
<211> LENGTH: 33
<212> TYPE: PRT
<213> ORGANISM: Artificial
<220> FEATURE:
<223> OTHER INFORMATION: AR module (M1.1b)

<400> SEQUENCE: 16

Lys Asp Phe Gln Gly Ile Thr Pro Leu His Ile Ala Ala Thr Ser Gly
```

His Leu Glu Ile Val Glu Val Leu Leu Lys Ala Gly Ala Asp Val Asn
            20                  25                  30

Ala

<210> SEQ ID NO 17
<211> LENGTH: 33
<212> TYPE: PRT
<213> ORGANISM: Artificial
<220> FEATURE:
<223> OTHER INFORMATION: AR module (M1.1b)

<400> SEQUENCE: 17

Lys Asp Phe Glu Gly Val Thr Pro Leu His Leu Ala Ala Gln Trp Gly
1               5                   10                  15

His Leu Glu Ile Val Glu Val Leu Leu Lys Ala Gly Ala Asp Val Asn
            20                  25                  30

Ala

<210> SEQ ID NO 18
<211> LENGTH: 33
<212> TYPE: PRT
<213> ORGANISM: Artificial
<220> FEATURE:
<223> OTHER INFORMATION: AR module (M1.1b)

<400> SEQUENCE: 18

Lys Asp Ile Thr Gly Glu Thr Pro Leu His His Ala Ala Asp Ser Gly
1               5                   10                  15

His Leu Glu Ile Val Glu Val Leu Leu Lys Ala Gly Ala Asp Val Asn
            20                  25                  30

Ala

<210> SEQ ID NO 19
<211> LENGTH: 28
<212> TYPE: PRT
<213> ORGANISM: Artificial
<220> FEATURE:
<223> OTHER INFORMATION: C-Cap module (Cr)

<400> SEQUENCE: 19

Gln Asp Lys Ala Gly Val Thr Pro Ala Asp Leu Ala Ala Ala Trp Gly
1               5                   10                  15

His Glu Asp Ile Ala Glu Val Leu Gln Lys Leu Asn
            20                  25

<210> SEQ ID NO 20
<211> LENGTH: 32
<212> TYPE: PRT
<213> ORGANISM: Artificial
<220> FEATURE:
<223> OTHER INFORMATION: N-Cap module (Nr)

<400> SEQUENCE: 20

Gly Ser Asp Leu Gly Trp Lys Leu Leu Trp Ala Ala Ala His Gly Gln
1               5                   10                  15

Asp Asp Glu Val Arg Ile Leu Leu Ala Ala Gly Ala Asp Val Asn Ala
            20                  25                  30

<210> SEQ ID NO 21
<211> LENGTH: 33
<212> TYPE: PRT

<213> ORGANISM: Artificial
<220> FEATURE:
<223> OTHER INFORMATION: AR module (M1.1b)

<400> SEQUENCE: 21

Lys Asp Trp Glu Gly Thr Thr Pro Leu His Leu Ala Ala His Thr Gly
1               5                   10                  15
His Leu Glu Ile Val Glu Val Leu Leu Lys Ala Gly Ala Asp Val Asn
            20                  25                  30
Ala

<210> SEQ ID NO 22
<211> LENGTH: 33
<212> TYPE: PRT
<213> ORGANISM: Artificial
<220> FEATURE:
<223> OTHER INFORMATION: AR module (M1.1b)

<400> SEQUENCE: 22

Lys Asp Thr Val Gly Thr Thr Pro Leu His Tyr Ala Ala Glu Asp Gly
1               5                   10                  15
His Leu Glu Ile Val Glu Val Leu Leu Lys Ala Gly Ala Asp Val Asn
            20                  25                  30
Ala

<210> SEQ ID NO 23
<211> LENGTH: 33
<212> TYPE: PRT
<213> ORGANISM: Artificial
<220> FEATURE:
<223> OTHER INFORMATION: AR module (M1.1b)

<400> SEQUENCE: 23

Lys Asp Glu Tyr Gly Phe Thr Pro Leu His Leu Ala Ala Gln Phe Asp
1               5                   10                  15
His Leu Glu Ile Val Glu Val Leu Leu Lys Ala Gly Ala Asp Val Asn
            20                  25                  30
Ala

<210> SEQ ID NO 24
<211> LENGTH: 28
<212> TYPE: PRT
<213> ORGANISM: Artificial
<220> FEATURE:
<223> OTHER INFORMATION: C-Cap module (Cr)

<400> SEQUENCE: 24

Gln Asp Trp Val Gly Gln Thr Pro Ala Asp Leu Ala Ala Ala Trp Gly
1               5                   10                  15
His Glu Asp Ile Ala Glu Val Leu Gln Lys Leu Asn
            20                  25

<210> SEQ ID NO 25
<211> LENGTH: 28
<212> TYPE: PRT
<213> ORGANISM: Artificial
<220> FEATURE:
<223> OTHER INFORMATION: C-Cap module (Cr)

<400> SEQUENCE: 25

Gln Asp Glu Arg Gly Trp Thr Pro Ala Asp Leu Ala Ala Asp Trp Gly
1               5                   10                  15

His Glu Asp Ile Ala Glu Val Leu Gln Lys Leu Asn
              20                  25

<210> SEQ ID NO 26
<211> LENGTH: 32
<212> TYPE: PRT
<213> ORGANISM: Artificial
<220> FEATURE:
<223> OTHER INFORMATION: N-Cap module (Nr)

<400> SEQUENCE: 26

Gly Ser Asp Leu Gly His Lys Leu Leu Glu Ala Ala Val Ala Gly Gln
1               5                   10                  15
Asp Asp Glu Val Arg Ile Leu Leu Ala Ala Gly Ala Asp Val Asn Ala
            20                  25                  30

<210> SEQ ID NO 27
<211> LENGTH: 32
<212> TYPE: PRT
<213> ORGANISM: Artificial
<220> FEATURE:
<223> OTHER INFORMATION: N-Cap module (Nr)

<400> SEQUENCE: 27

Gly Ser Asp Leu Gly Val Lys Leu Leu Trp Ala Ala Ser His Gly Gln
1               5                   10                  15
Asp Asp Glu Val Arg Ile Leu Leu Ala Ala Gly Ala Asp Val Asn Ala
            20                  25                  30

<210> SEQ ID NO 28
<211> LENGTH: 33
<212> TYPE: PRT
<213> ORGANISM: Artificial
<220> FEATURE:
<223> OTHER INFORMATION: AR module (M1.1b)

<400> SEQUENCE: 28

Lys Asp Trp Tyr Gly Lys Thr Pro Leu His Phe Ala Ala Gly Leu Gly
1               5                   10                  15
His Leu Glu Ile Val Glu Val Leu Leu Lys Ala Gly Ala Asp Val Asn
            20                  25                  30
Ala

<210> SEQ ID NO 29
<211> LENGTH: 32
<212> TYPE: PRT
<213> ORGANISM: Artificial
<220> FEATURE:
<223> OTHER INFORMATION: AR module (M1.1b)

<400> SEQUENCE: 29

Lys Asp Phe Phe Gly Ile Thr Pro Leu His Gln Ala Ala Trp Gly His
1               5                   10                  15
Leu Glu Ile Val Glu Val Leu Leu Lys Ala Gly Ala Asp Val Asn Ala
            20                  25                  30

<210> SEQ ID NO 30
<211> LENGTH: 33
<212> TYPE: PRT
<213> ORGANISM: Artificial
<220> FEATURE:
<223> OTHER INFORMATION: AR module (M1.1b)

<400> SEQUENCE: 30

Lys Asp Asp Phe Gly Thr Thr Pro Leu His Ala Ala Asp Tyr Gly
1               5                   10                  15

His Leu Glu Ile Val Glu Val Leu Leu Lys Ala Gly Ala Asp Val Asn
            20                  25                  30

Ala

<210> SEQ ID NO 31
<211> LENGTH: 33
<212> TYPE: PRT
<213> ORGANISM: Artificial
<220> FEATURE:
<223> OTHER INFORMATION: AR module (M1.1b)

<400> SEQUENCE: 31

Lys Asp Glu Asp Gly Gln Thr Pro Leu His Leu Ala Ala Ala Tyr Gly
1               5                   10                  15

His Leu Glu Ile Val Glu Val Leu Leu Lys Ala Gly Ala Asp Val Asn
            20                  25                  30

Ala

<210> SEQ ID NO 32
<211> LENGTH: 33
<212> TYPE: PRT
<213> ORGANISM: Artificial
<220> FEATURE:
<223> OTHER INFORMATION: AR module (M1.1b)

<400> SEQUENCE: 32

Lys Glu Glu Asp Gly Thr Thr Pro Leu His Leu Ala Ala Thr His Gly
1               5                   10                  15

His Leu Glu Ile Val Glu Val Leu Leu Lys Ala Gly Ala Asp Val Asn
            20                  25                  30

Ala

<210> SEQ ID NO 33
<211> LENGTH: 28
<212> TYPE: PRT
<213> ORGANISM: Artificial
<220> FEATURE:
<223> OTHER INFORMATION: C-Cap module (Cr)

<400> SEQUENCE: 33

Gln Asp Tyr Thr Gly His Thr Pro Ala Asp Leu Ala Ala Val Tyr Gly
1               5                   10                  15

His Glu Asp Ile Ala Ala Val Leu Gln Lys Leu Asn
            20                  25

<210> SEQ ID NO 34
<211> LENGTH: 28
<212> TYPE: PRT
<213> ORGANISM: Artificial
<220> FEATURE:
<223> OTHER INFORMATION: C-Cap module (Cr)

<400> SEQUENCE: 34

Gln Asp Asn Asp Gly Phe Thr Pro Ala Asp Leu Ala Ala Asp Ser Gly
1               5                   10                  15

His Glu Asp Ile Ala Glu Val Leu Gln Lys Leu Asn
            20                  25

<210> SEQ ID NO 35
<211> LENGTH: 28

```
<212> TYPE: PRT
<213> ORGANISM: Artificial
<220> FEATURE:
<223> OTHER INFORMATION: C-Cap module (Cr)

<400> SEQUENCE: 35

Gln Asp Trp Tyr Gly Thr Thr Pro Ala Asp Leu Ala Ala Trp Trp Gly
1               5                   10                  15
His Glu Asp Ile Ala Glu Val Leu Gln Lys Leu Asn
            20                  25

<210> SEQ ID NO 36
<211> LENGTH: 32
<212> TYPE: PRT
<213> ORGANISM: Artificial
<220> FEATURE:
<223> OTHER INFORMATION: N-Cap module (Nr)

<400> SEQUENCE: 36

Gly Ser Asp Leu Gly Ile Lys Leu Leu Phe Ala Ala Ser Arg Gly Gln
1               5                   10                  15
Asp Asp Glu Val Arg Glu Leu Leu Lys Ala Gly Ala Asp Val Asn Ala
            20                  25                  30

<210> SEQ ID NO 37
<211> LENGTH: 33
<212> TYPE: PRT
<213> ORGANISM: Artificial
<220> FEATURE:
<223> OTHER INFORMATION: AR module (M1.1b)

<400> SEQUENCE: 37

Lys Asp Phe Glu Gly Ile Thr Pro Leu His Ala Ala Ala Arg Ser Gly
1               5                   10                  15
His Leu Glu Ile Val Glu Val Leu Leu Lys Ala Gly Ala Asp Val Asn
            20                  25                  30
Ala

<210> SEQ ID NO 38
<211> LENGTH: 33
<212> TYPE: PRT
<213> ORGANISM: Artificial
<220> FEATURE:
<223> OTHER INFORMATION: AR module (M1.1b)

<400> SEQUENCE: 38

Lys Asp Val Glu Gly Trp Thr Pro Leu His Tyr Ala Ala Ser Ser Gly
1               5                   10                  15
His Leu Glu Ile Val Glu Val Leu Leu Lys Ala Gly Ala Asp Val Asn
            20                  25                  30
Ala

<210> SEQ ID NO 39
<211> LENGTH: 28
<212> TYPE: PRT
<213> ORGANISM: Artificial
<220> FEATURE:
<223> OTHER INFORMATION: C-Cap module (Cr)

<400> SEQUENCE: 39

Gln Asp Asn His Gly Ala Thr Pro Ala Asp Leu Ala Ala Gln Trp Gly
1               5                   10                  15
His Glu Asp Ile Ala Glu Val Leu Gln Lys Leu Asn
```

20                  25

<210> SEQ ID NO 40
<211> LENGTH: 32
<212> TYPE: PRT
<213> ORGANISM: Artificial
<220> FEATURE:
<223> OTHER INFORMATION: N-Cap module (Nr)

<400> SEQUENCE: 40

Gly Ser Asp Leu Gly Asn Lys Leu Leu Ile Ala Ala Ser Val Gly Gln
1               5                   10                  15

Asp Asp Glu Val Arg Ile Leu Leu Ala Ala Gly Ala Asp Val Asn Ala
                20                  25                  30

<210> SEQ ID NO 41
<211> LENGTH: 33
<212> TYPE: PRT
<213> ORGANISM: Artificial
<220> FEATURE:
<223> OTHER INFORMATION: AR module (M1.1b)

<400> SEQUENCE: 41

Lys Asp Glu Thr Gly Trp Thr Pro Leu His Leu Ala Ala Ala Trp Gly
1               5                   10                  15

His Leu Glu Ile Val Glu Val Leu Leu Lys Ala Gly Ala Asp Val Asn
                20                  25                  30

Ala

<210> SEQ ID NO 42
<211> LENGTH: 33
<212> TYPE: PRT
<213> ORGANISM: Artificial
<220> FEATURE:
<223> OTHER INFORMATION: AR module (M1.1b)

<400> SEQUENCE: 42

Lys Asp Val Lys Gly Gln Thr Pro Leu His Leu Ala Ala Ala Tyr Gly
1               5                   10                  15

His Leu Glu Ile Val Glu Val Leu Leu Lys Ala Gly Ala Asp Val Asn
                20                  25                  30

Ala

<210> SEQ ID NO 43
<211> LENGTH: 28
<212> TYPE: PRT
<213> ORGANISM: Artificial
<220> FEATURE:
<223> OTHER INFORMATION: C-Cap module (Cr)

<400> SEQUENCE: 43

Gln Asp Asn Asp Gly Tyr Thr Pro Ala Asp Leu Ala Ala Arg Tyr Gly
1               5                   10                  15

His Glu Asp Ile Ala Glu Val Leu Gln Lys Leu Asn
                20                  25

<210> SEQ ID NO 44
<211> LENGTH: 32
<212> TYPE: PRT
<213> ORGANISM: Artificial
<220> FEATURE:
<223> OTHER INFORMATION: N-Cap module (Nr)

<400> SEQUENCE: 44

```
Gly Ser Asp Leu Gly Lys Lys Leu Leu Asn Ala Ala Val Cys Gly Gln
1               5                   10                  15

Asp Asp Glu Val Arg Ile Leu Leu Val Ala Gly Ala Asp Val Asn Ala
                20                  25                  30

<210> SEQ ID NO 45
<211> LENGTH: 32
<212> TYPE: PRT
<213> ORGANISM: Artificial
<220> FEATURE:
<223> OTHER INFORMATION: N-Cap module (Nr)

<400> SEQUENCE: 45

Gly Ser Asp Leu Gly Thr Lys Leu Leu Asp Ala Ala Thr Tyr Gly Gln
1               5                   10                  15

Asp Asp Glu Val Arg Ile Leu Leu Ala Ala Gly Ala Asp Val Asn Ala
                20                  25                  30

<210> SEQ ID NO 46
<211> LENGTH: 33
<212> TYPE: PRT
<213> ORGANISM: Artificial
<220> FEATURE:
<223> OTHER INFORMATION: AR module (M1.1b)

<400> SEQUENCE: 46

Lys Asp Trp Arg Gly Phe Thr Pro Leu His Tyr Ala Ala Tyr Leu Gly
1               5                   10                  15

His Leu Glu Ile Val Glu Val Leu Leu Lys Ala Gly Ala Asp Val Asn
                20                  25                  30

Ala

<210> SEQ ID NO 47
<211> LENGTH: 33
<212> TYPE: PRT
<213> ORGANISM: Artificial
<220> FEATURE:
<223> OTHER INFORMATION: AR module (M1.1b)

<400> SEQUENCE: 47

Lys Asp Thr Ile Gly His Thr Pro Leu His Arg Ala Ala Phe Val Gly
1               5                   10                  15

Gln Leu Glu Ile Val Glu Val Leu Leu Lys Ala Gly Ala Asp Val Asn
                20                  25                  30

Ala

<210> SEQ ID NO 48
<211> LENGTH: 28
<212> TYPE: PRT
<213> ORGANISM: Artificial
<220> FEATURE:
<223> OTHER INFORMATION: C-Cap module (Cr)

<400> SEQUENCE: 48

Gln Asp Thr Ala Gly Tyr Thr Pro Ala Asp Leu Ala Ala Trp Thr Gly
1               5                   10                  15

His Glu Asp Ile Ala Glu Val Leu Gln Lys Leu Asn
                20                  25

<210> SEQ ID NO 49
<211> LENGTH: 28
<212> TYPE: PRT
```

```
<213> ORGANISM: Artificial
<220> FEATURE:
<223> OTHER INFORMATION: C-Cap module (Cr)

<400> SEQUENCE: 49

Gln Asp Asp Tyr Gly Trp Thr Pro Ala Asp Leu Ala Ala Asn Ser Gly
 1               5                  10                  15

His Glu Asp Ile Ala Glu Val Leu Gln Lys Leu Asn
            20                  25

<210> SEQ ID NO 50
<211> LENGTH: 32
<212> TYPE: PRT
<213> ORGANISM: Artificial
<220> FEATURE:
<223> OTHER INFORMATION: N-Cap module (Nr)

<400> SEQUENCE: 50

Gly Ser Asp Leu Gly Ile Lys Leu Leu Gln Ala Ala Asn Leu Gly Gln
 1               5                  10                  15

Asp Asp Glu Val Arg Ile Leu Leu Ala Thr Gly Ala Asp Val Asn Ala
            20                  25                  30

<210> SEQ ID NO 51
<211> LENGTH: 33
<212> TYPE: PRT
<213> ORGANISM: Artificial
<220> FEATURE:
<223> OTHER INFORMATION: AR module (M1.1b)

<400> SEQUENCE: 51

Lys Asp Ser Ile Gly Gln Thr Pro Leu His Trp Ala Ala Arg Arg Gly
 1               5                  10                  15

His Leu Glu Ile Val Glu Val Leu Leu Lys Ala Gly Ala Asp Val Asn
            20                  25                  30

Ala

<210> SEQ ID NO 52
<211> LENGTH: 33
<212> TYPE: PRT
<213> ORGANISM: Artificial
<220> FEATURE:
<223> OTHER INFORMATION: AR module (M1.1b)

<400> SEQUENCE: 52

Lys Asp Glu Tyr Gly Val Thr Pro Leu His Leu Ala Ala Ser Leu Gly
 1               5                  10                  15

His Leu Glu Ile Val Glu Val Leu Leu Lys Ala Gly Ala Asp Val Asn
            20                  25                  30

Ala

<210> SEQ ID NO 53
<211> LENGTH: 28
<212> TYPE: PRT
<213> ORGANISM: Artificial
<220> FEATURE:
<223> OTHER INFORMATION: C-Cap module (Cr)

<400> SEQUENCE: 53

Gln Asp Thr Ala Gly Gln Thr Pro Ala Asp Leu Ala Ala Asp Asp Gly
 1               5                  10                  15

His Glu Asp Ile Ala Val Val Leu Gln Lys Leu Asn
            20                  25
```

<210> SEQ ID NO 54
<211> LENGTH: 32
<212> TYPE: PRT
<213> ORGANISM: Artificial
<220> FEATURE:
<223> OTHER INFORMATION: N-Cap module (old)

<400> SEQUENCE: 54

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

<210> SEQ ID NO 55
<211> LENGTH: 33
<212> TYPE: PRT
<213> ORGANISM: Artificial
<220> FEATURE:
<223> OTHER INFORMATION: AR module (old)

<400> SEQUENCE: 55

Lys Asp Glu Tyr Gly Leu Thr Pro Leu Tyr Leu Ala Thr Ala His Gly
1               5                   10                  15

His Leu Glu Ile Val Glu Val Leu Leu Lys Ala Gly Ala Asp Val Asn
            20                  25                  30

Ala

<210> SEQ ID NO 56
<211> LENGTH: 33
<212> TYPE: PRT
<213> ORGANISM: Artificial
<220> FEATURE:
<223> OTHER INFORMATION: AR module (old)

<400> SEQUENCE: 56

Val Asp Ala Ile Gly Phe Thr Pro Leu His Leu Ala Ala Phe Ile Gly
1               5                   10                  15

His Leu Glu Ile Val Glu Val Leu Leu Lys Ala Gly Ala Asp Val Asn
            20                  25                  30

Ala

<210> SEQ ID NO 57
<211> LENGTH: 28
<212> TYPE: PRT
<213> ORGANISM: Artificial
<220> FEATURE:
<223> OTHER INFORMATION: C-Cap module (old)

<400> SEQUENCE: 57

Gln Asp Lys Ser Gly Lys Thr Pro Ala Asp Leu Ala Ala Gly Ala Gly
1               5                   10                  15

His Glu Asp Ile Ala Glu Val Leu Gln Lys Leu Asn
            20                  25

<210> SEQ ID NO 58
<211> LENGTH: 33
<212> TYPE: PRT
<213> ORGANISM: Artificial
<220> FEATURE:
<223> OTHER INFORMATION: AR sequence motif
<220> FEATURE:
<221> NAME/KEY: misc_feature
<222> LOCATION: (1)..(1)

```
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 58

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 59
<211> LENGTH: 33
<212> TYPE: PRT
<213> ORGANISM: Artificial
<220> FEATURE:
<223> OTHER INFORMATION: AR sequence motif
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 59

Lys Asp Xaa Xaa Gly Xaa Thr Pro Leu His Xaa Ala Ala Xaa Xaa Gly
1               5                   10                  15

His Leu Glu Ile Val Glu Val Leu Leu Lys Ala Gly Ala Asp Val Asn
            20                  25                  30

Ala

<210> SEQ ID NO 60
<211> LENGTH: 32
<212> TYPE: PRT
<213> ORGANISM: Artificial
<220> FEATURE:
<223> OTHER INFORMATION: AR sequence motif
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
```

```
<222> LOCATION: (13)..(14)
<223> OTHER INFORMATION: Xaa can be any naturally occurring amino acid

<400> SEQUENCE: 60

Gly Ser Asp Leu Gly Xaa Lys Leu Leu Xaa Ala Ala Xaa Xaa Gly Gln
1               5                   10                  15

Asp Asp Glu Val Arg Ile Leu Leu Ala Ala Gly Ala Asp Val Asn Ala
            20                  25                  30

<210> SEQ ID NO 61
<211> LENGTH: 28
<212> TYPE: PRT
<213> ORGANISM: Artificial
<220> FEATURE:
<223> OTHER INFORMATION: AR sequence motif
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 61

Gln Asp Xaa Xaa Gly Xaa Thr Pro Ala Asp Leu Ala Ala Xaa Xaa Gly
1               5                   10                  15

His Glu Asp Ile Ala Glu Val Leu Gln Lys Leu Asn
            20                  25

<210> SEQ ID NO 62
<211> LENGTH: 126
<212> TYPE: PRT
<213> ORGANISM: Artificial
<220> FEATURE:
<223> OTHER INFORMATION: AR domain (one-domain)

<400> SEQUENCE: 62

Gly Ser Asp Leu Gly Val Lys Leu Leu Trp Ala Ala Ala Arg Gly Gln
1               5                   10                  15

Asp Asp Glu Val Arg Ile Leu Leu Ala Ala Gly Ala Asp Val Asn Ala
            20                  25                  30

Lys Asp Phe Gln Gly Ile Thr Pro Leu His Ile Ala Ala Gln Ser Gly
        35                  40                  45

His Leu Glu Ile Val Glu Val Leu Leu Lys Ala Gly Ala Asp Val Asn
    50                  55                  60

Ala Lys Asp Val Thr Gly Asp Thr Pro Leu His Leu Ala Ala Gln His
65                  70                  75                  80

Gly His Leu Val Ile Val Glu Val Leu Leu Lys Ala Gly Ala Asp Val
                85                  90                  95

Asn Ala Gln Asp Glu Arg Gly Trp Thr Pro Ala Asp Leu Ala Ala Asp
            100                 105                 110

Trp Gly His Glu Asp Ile Ala Glu Val Leu Gln Lys Leu Asn
        115                 120                 125

<210> SEQ ID NO 63
<211> LENGTH: 126
<212> TYPE: PRT
<213> ORGANISM: Artificial
<220> FEATURE:
```

<223> OTHER INFORMATION: AR domain (one-domain)

<400> SEQUENCE: 63

Gly Ser Asp Leu Gly Val Lys Leu Leu Trp Ala Ala Ala Arg Gly Gln
1               5                   10                  15

Asp Asp Glu Val Arg Glu Leu Leu Lys Ala Gly Ala Asp Val Asn Ala
            20                  25                  30

Lys Asp Phe Gln Gly Ile Thr Pro Leu His Ile Ala Ala Thr Ser Gly
        35                  40                  45

His Leu Glu Ile Val Glu Val Leu Leu Lys Ala Gly Ala Asp Val Asn
    50                  55                  60

Ala Lys Asp Ile Thr Gly Glu Thr Pro Leu His Ala Ala Asp Ser
65                  70                  75                  80

Gly His Leu Glu Ile Val Glu Val Leu Leu Lys Ala Gly Ala Asp Val
                85                  90                  95

Asn Ala Gln Asp Lys Ala Gly Val Thr Pro Ala Asp Leu Ala Ala Ala
            100                 105                 110

Trp Gly His Glu Asp Ile Ala Glu Val Leu Gln Lys Leu Asn
        115                 120                 125

<210> SEQ ID NO 64
<211> LENGTH: 126
<212> TYPE: PRT
<213> ORGANISM: Artificial
<220> FEATURE:
<223> OTHER INFORMATION: AR domain (one-domain)

<400> SEQUENCE: 64

Gly Ser Asp Leu Gly Ile Lys Leu Leu Phe Ala Ala Ala Lys Ser Gln
1               5                   10                  15

Asp Asp Glu Val Arg Ile Leu Leu Ala Ala Gly Ala Asp Val Asn Ala
            20                  25                  30

Lys Asp Phe Gln Ser Val Thr Pro Leu His Ile Ala Ala Gln Ser Gly
        35                  40                  45

His Leu Glu Ile Val Glu Val Leu Leu Lys Ala Gly Ala Asp Val Asn
    50                  55                  60

Ala Lys Asp Val Thr Gly Asp Thr Pro Leu His Leu Ala Ala Gln His
65                  70                  75                  80

Gly His Leu Glu Ile Val Glu Val Leu Leu Lys Ala Gly Ala Asp Val
                85                  90                  95

Asn Ala Gln Asp Glu Arg Gly Trp Thr Pro Ala Asp Leu Ala Ala Asp
            100                 105                 110

Trp Gly His Glu Asp Ile Ala Glu Val Leu Gln Lys Leu Asn
        115                 120                 125

<210> SEQ ID NO 65
<211> LENGTH: 126
<212> TYPE: PRT
<213> ORGANISM: Artificial
<220> FEATURE:
<223> OTHER INFORMATION: AR domain (one-domain)

<400> SEQUENCE: 65

Gly Ser Asp Leu Gly Val Lys Leu Leu Trp Ala Ala Ala Arg Gly Gln
1               5                   10                  15

Asp Asp Glu Val Arg Glu Leu Leu Lys Ala Gly Ala Asp Val Asn Ala
            20                  25                  30

Lys Asp Phe Gln Gly Ile Thr Pro Leu His Ile Ala Ala Gln Ser Gly

```
            35                  40                  45
His Leu Glu Ile Val Glu Val Leu Lys Ala Gly Ala Asp Val Asn
        50                  55                  60
Ala Lys Asp Val Thr Gly Asp Thr Pro Leu His Leu Ala Ala Gln His
 65                  70                  75                  80
Gly His Leu Glu Ile Val Glu Val Leu Leu Lys Ala Gly Ala Asp Val
                85                  90                  95
Asn Ala Gln Asp Glu Arg Gly Lys Thr Pro Ala Asp Leu Ala Ala Asp
                100                 105                 110
Trp Gly His Glu Asp Ile Ala Glu Val Leu Gln Lys Leu Asn
            115                 120                 125
```

<210> SEQ ID NO 66
<211> LENGTH: 126
<212> TYPE: PRT
<213> ORGANISM: Artificial
<220> FEATURE:
<223> OTHER INFORMATION: AR domain (one-domain)

<400> SEQUENCE: 66

```
Gly Ser Asp Leu Gly Val Lys Leu Leu Trp Ala Ala Ala Arg Gly Gln
 1               5                   10                  15
Asp Asp Glu Val Arg Ile Leu Leu Ala Ala Gly Ala Asp Val Asn Ala
                20                  25                  30
Lys Asp Phe Gln Gly Ile Thr Pro Leu His Ile Ala Ala Thr Asn Gly
            35                  40                  45
His Leu Glu Ile Val Glu Val Leu Leu Lys Ala Gly Ala Asp Val Asn
        50                  55                  60
Ala Lys Asp Ile Thr Gly Glu Thr Pro Leu His His Ala Ala Asp Ser
 65                  70                  75                  80
Gly His Leu Glu Ile Val Glu Val Leu Leu Lys Ala Gly Ala Asp Val
                85                  90                  95
Asn Ala Gln Asp Lys Ala Gly Val Thr Pro Ala Asp Leu Ala Ala Ala
                100                 105                 110
Trp Gly His Glu Asp Ile Ala Glu Val Leu Gln Lys Leu Asn
            115                 120                 125
```

<210> SEQ ID NO 67
<211> LENGTH: 126
<212> TYPE: PRT
<213> ORGANISM: Artificial
<220> FEATURE:
<223> OTHER INFORMATION: AR domain (one-domain)

<400> SEQUENCE: 67

```
Gly Ser Asp Leu Gly Val Asn Leu Leu Trp Ala Ala Thr Arg Gly Gln
 1               5                   10                  15
Asp Asp Glu Val Arg Ile Leu Leu Ala Ala Gly Ala Asp Val Asn Ala
                20                  25                  30
Lys Asp Phe Glu Gly Val Thr Pro Leu His Leu Ala Ala Gln Trp Gly
            35                  40                  45
His Leu Glu Ile Val Glu Val Leu Leu Lys Ala Gly Ala Asp Val Asn
        50                  55                  60
Ala Lys Asp Val Thr Gly Asp Thr Pro Leu His Leu Ala Ala Gln His
 65                  70                  75                  80
Gly His Leu Glu Ile Val Glu Val Leu Leu Lys Ala Gly Ala Asp Val
                85                  90                  95
```

```
Asn Ala Gln Asp Glu Arg Gly Trp Thr Pro Ala Asp Leu Ala Ala Asp
                100                 105                 110

Trp Gly His Glu Asp Ile Ala Glu Val Leu Gln Lys Leu Asn
        115                 120                 125
```

<210> SEQ ID NO 68
<211> LENGTH: 126
<212> TYPE: PRT
<213> ORGANISM: Artificial
<220> FEATURE:
<223> OTHER INFORMATION: AR domain (one-domain)

<400> SEQUENCE: 68

```
Gly Ser Asp Leu Gly Ile Lys Leu Leu Phe Ala Ala Lys Gly Gln
1               5                   10                  15

Asp Asp Glu Val Arg Ile Leu Leu Ala Ala Gly Ala Asp Val Asn Ala
                20                  25                  30

Lys Asp Phe Glu Gly Tyr Thr Pro Leu His Val Ala Ala Tyr Asp Gly
            35                  40                  45

His Leu Glu Ile Val Glu Val Leu Leu Lys Ala Gly Ala Asp Val Asn
    50                  55                  60

Ala Lys Asp Ser Gln Gly Arg Thr Pro Leu His Glu Ala Ala Tyr Ser
65                  70                  75                  80

Gly His Leu Glu Ile Val Glu Val Leu Leu Lys Ala Gly Ala Asp Val
                85                  90                  95

Asn Ala Gln Asp Asp Ala Gly Glu Thr Pro Ala Asp Leu Ala Ala Ala
                100                 105                 110

Trp Gly His Glu Asp Ile Ala Glu Val Leu Gln Lys Leu Asn
        115                 120                 125
```

<210> SEQ ID NO 69
<211> LENGTH: 126
<212> TYPE: PRT
<213> ORGANISM: Artificial
<220> FEATURE:
<223> OTHER INFORMATION: AR domain (one-domain)

<400> SEQUENCE: 69

```
Gly Ser Asp Leu Gly Ile Lys Leu Leu Trp Ala Ala Ala His Gly Gln
1               5                   10                  15

Asp Asp Glu Val Arg Ile Leu Leu Ala Ala Ala Asp Val Asn Ala
                20                  25                  30

Lys Asp Trp Tyr Gly Thr Thr Pro Leu His Ile Ala Ala Val Ala Gly
            35                  40                  45

His Leu Glu Ile Val Glu Val Leu Leu Lys Ala Gly Ala Asp Val Asn
    50                  55                  60

Ala Lys Asp Asp Phe Gly Thr Thr Pro Leu His Leu Ala Ala Tyr His
65                  70                  75                  80

Gly His Leu Glu Ile Val Glu Val Leu Leu Lys Ala Gly Ala Asp Val
                85                  90                  95

Asn Ala Gln Asp Trp Gln Gly Gln Thr Pro Ala Asp Leu Ala Ala Gln
                100                 105                 110

Asp Gly His Glu Asp Ile Ala Glu Val Leu Gln Lys Leu Asn
        115                 120                 125
```

<210> SEQ ID NO 70
<211> LENGTH: 126
<212> TYPE: PRT
<213> ORGANISM: Artificial

<220> FEATURE:
<223> OTHER INFORMATION: AR domain (one-domain)

<400> SEQUENCE: 70

Gly Ser Asp Leu Gly His Lys Leu Leu Glu Ala Ala Val Ala Gly Gln
1               5                   10                  15

Asp Asp Glu Val Arg Ile Leu Leu Ala Ala Gly Ala Asp Val Asn Ala
            20                  25                  30

Lys Asp Trp Tyr Gly Lys Thr Pro Leu His Phe Ala Ala Gly Leu Gly
        35                  40                  45

His Leu Glu Ile Val Glu Val Leu Leu Lys Ala Gly Ala Asp Val Asn
    50                  55                  60

Ala Lys Asp Glu Asp Gly Gln Thr Pro Leu His Leu Ala Ala Ala Tyr
65                  70                  75                  80

Gly His Leu Glu Ile Val Glu Val Leu Leu Lys Ala Gly Ala Asp Val
            85                  90                  95

Asn Ala Gln Asp Asn Asp Gly Phe Thr Pro Ala Asp Leu Ala Ala Asp
                100                 105                 110

Ser Gly His Glu Asp Ile Ala Glu Val Leu Gln Lys Leu Asn
        115                 120                 125

<210> SEQ ID NO 71
<211> LENGTH: 125
<212> TYPE: PRT
<213> ORGANISM: Artificial
<220> FEATURE:
<223> OTHER INFORMATION: AR domain (one-domain)

<400> SEQUENCE: 71

Gly Ser Asp Leu Gly Val Lys Leu Leu Trp Ala Ala Ser His Gly Gln
1               5                   10                  15

Asp Asp Glu Val Arg Ile Leu Leu Ala Ala Gly Ala Asp Val Asn Ala
            20                  25                  30

Lys Asp Phe Phe Gly Ile Thr Pro Leu His Gln Ala Ala Trp Gly His
        35                  40                  45

Leu Glu Ile Val Glu Val Leu Leu Lys Ala Gly Ala Asp Val Asn Ala
    50                  55                  60

Lys Glu Glu Asp Gly Thr Thr Pro Leu His Leu Ala Ala Thr His Gly
65                  70                  75                  80

His Leu Glu Ile Val Glu Val Leu Leu Lys Ala Gly Ala Asp Val Asn
            85                  90                  95

Ala Gln Asp Trp Tyr Gly Thr Thr Pro Ala Asp Leu Ala Ala Trp Trp
                100                 105                 110

Gly His Glu Asp Ile Ala Glu Val Leu Gln Lys Leu Asn
        115                 120                 125

<210> SEQ ID NO 72
<211> LENGTH: 126
<212> TYPE: PRT
<213> ORGANISM: Artificial
<220> FEATURE:
<223> OTHER INFORMATION: AR domain (one-domain)

<400> SEQUENCE: 72

Gly Ser Asp Leu Gly Ile Lys Leu Leu Phe Ala Ala Ser Arg Gly Gln
1               5                   10                  15

Asp Asp Glu Val Arg Ile Leu Leu Ala Ala Gly Ala Asp Val Asn Ala
            20                  25                  30

```
Lys Asp Phe Glu Gly Ile Thr Pro Leu His Ala Ala Arg Ser Gly
         35                  40                  45

His Leu Glu Ile Val Glu Val Leu Leu Lys Ala Gly Ala Asp Val Asn
 50                  55                  60

Ala Lys Asp Val Glu Gly Trp Thr Pro Leu His Tyr Ala Ala Ser Tyr
 65                  70                  75                  80

Gly His Leu Glu Ile Val Glu Val Leu Leu Lys Ala Gly Ala Asp Val
                 85                  90                  95

Asn Ala Gln Asp Asn His Gly Ala Thr Pro Ala Asp Leu Ala Ala Gln
                100                 105                 110

Trp Gly His Glu Asp Ile Ala Glu Val Leu Gln Lys Leu Asn
                115                 120                 125
```

<210> SEQ ID NO 73
<211> LENGTH: 159
<212> TYPE: PRT
<213> ORGANISM: Artificial
<220> FEATURE:
<223> OTHER INFORMATION: AR domain (one-domain)

<400> SEQUENCE: 73

```
Gly Ser Asp Leu Gly Lys Lys Leu Leu Glu Ala Ala Arg Ala Gly Gln
  1               5                  10                  15

Asp Asp Glu Val Arg Ile Leu Met Ala Asn Gly Ala Asp Val Asn Ala
                 20                  25                  30

Lys Asp Phe Tyr Gly Ile Thr Pro Leu His Leu Ala Ala Ala Tyr Gly
                 35                  40                  45

His Leu Glu Ile Val Glu Val Leu Leu Lys His Gly Ala Asp Val Asn
 50                  55                  60

Ala His Asp Trp Asn Gly Trp Thr Pro Leu His Leu Ala Ala Lys Tyr
 65                  70                  75                  80

Gly His Leu Glu Ile Val Glu Val Leu Leu Lys His Gly Ala Asp Val
                 85                  90                  95

Asn Ala Ile Asp Asn Ala Gly Lys Thr Pro Leu His Leu Ala Ala Ala
                100                 105                 110

His Gly His Leu Glu Ile Val Glu Val Leu Leu Lys Tyr Gly Ala Asp
                115                 120                 125

Val Asn Ala Gln Asp Lys Phe Gly Lys Thr Ala Phe Asp Ile Ser Ile
                130                 135                 140

Asp Asn Gly Asn Glu Asp Leu Ala Glu Ile Leu Gln Lys Leu Asn
145                 150                 155
```

<210> SEQ ID NO 74
<211> LENGTH: 93
<212> TYPE: PRT
<213> ORGANISM: Artificial
<220> FEATURE:
<223> OTHER INFORMATION: AR domain (one-domain)

<400> SEQUENCE: 74

```
Gly Ser Asp Leu Gly Lys Lys Leu Leu Asn Ala Ala Val Cys Gly Gln
  1               5                  10                  15

Asp Asp Glu Val Arg Ile Leu Leu Val Ala Gly Ala Asp Val Asn Ala
                 20                  25                  30

Lys Asp Trp Arg Gly Phe Thr Pro Leu His Tyr Ala Ala Tyr Leu Gly
                 35                  40                  45

His Leu Glu Ile Val Glu Val Leu Leu Lys Ala Gly Ala Asp Val Asn
 50                  55                  60
```

```
Ala Gln Asp Thr Ala Gly Tyr Thr Pro Ala Asp Leu Ala Ala Trp Thr
 65                  70                  75                  80

Gly His Glu Asp Ile Ala Glu Val Leu Gln Lys Leu Asn
                 85                  90

<210> SEQ ID NO 75
<211> LENGTH: 93
<212> TYPE: PRT
<213> ORGANISM: Artificial
<220> FEATURE:
<223> OTHER INFORMATION: AR domain (one-domain)

<400> SEQUENCE: 75

Gly Ser Asp Leu Gly Ala Lys Leu Leu Ile Ala Ala Thr Val Gly Gln
  1               5                  10                  15

Asp Asp Glu Val Arg Ile Leu Leu Ala Ala Gly Ala Asp Val Asn Ala
                 20                  25                  30

Lys Asp Thr Ile Gly His Thr Pro Leu His Arg Ala Ala Phe Val Gly
             35                  40                  45

Gln Leu Glu Ile Val Glu Val Leu Leu Lys Ala Gly Ala Asp Val Asn
         50                  55                  60

Ala Gln Asp Asp Tyr Gly Trp Thr Pro Ala Asp Leu Ala Ala Asn Ser
 65                  70                  75                  80

Gly His Glu Asp Ile Ala Glu Val Leu Gln Lys Leu Asn
                 85                  90

<210> SEQ ID NO 76
<211> LENGTH: 93
<212> TYPE: PRT
<213> ORGANISM: Artificial
<220> FEATURE:
<223> OTHER INFORMATION: AR domain (one-domain)

<400> SEQUENCE: 76

Gly Ser Asp Leu Gly Ala Lys Leu Leu Val Ala Ala Thr Ser Gly Gln
  1               5                  10                  15

Asp Asp Glu Val Arg Ile Leu Leu Ala Ala Gly Ala Asp Val Asn Ala
                 20                  25                  30

Lys Asp Arg Ile Gly Phe Thr Pro Leu His Arg Ala Ala Phe Val Gly
             35                  40                  45

His Leu Glu Ile Val Glu Val Leu Leu Lys Ala Gly Ala Asp Val Asn
         50                  55                  60

Ala Gln Asp Asp Phe Gly His Thr Pro Ala Asp Leu Ala Ala Ser Leu
 65                  70                  75                  80

Gly His Glu Asp Ile Ala Glu Val Leu Gln Lys Leu Asn
                 85                  90

<210> SEQ ID NO 77
<211> LENGTH: 126
<212> TYPE: PRT
<213> ORGANISM: Artificial
<220> FEATURE:
<223> OTHER INFORMATION: AR domain (one-domain)

<400> SEQUENCE: 77

Gly Ser Asp Leu Gly Ile Lys Leu Leu Gln Ala Ala Asn Leu Gly Gln
  1               5                  10                  15

Asp Asp Glu Val Arg Glu Leu Leu Lys Ala Gly Ala Asp Val Asn Ala
                 20                  25                  30
```

```
Lys Asp Ser Ile Gly Gln Thr Pro Leu His Trp Ala Ala Arg Arg Gly
            35                  40                  45

His Leu Glu Ile Val Glu Val Leu Leu Lys Ala Gly Ala Asp Val Asn
 50                  55                  60

Ala Lys Asp Glu Tyr Gly Val Thr Pro Leu His Leu Ala Ala Ser Leu
 65                  70                  75                  80

Gly His Leu Glu Ile Val Glu Val Leu Leu Lys Ala Gly Ala Asp Val
                 85                  90                  95

Asn Ala Gln Asp Glu Ser Gly Glu Thr Pro Ala Asp Leu Ala Ala Leu
                100                 105                 110

His Gly His Glu Asp Ile Ala Glu Val Leu Gln Lys Leu Asn
            115                 120                 125
```

<210> SEQ ID NO 78
<211> LENGTH: 126
<212> TYPE: PRT
<213> ORGANISM: Artificial
<220> FEATURE:
<223> OTHER INFORMATION: AR domain (one-domain)

<400> SEQUENCE: 78

```
Gly Ser Asp Leu Gly Leu Lys Leu Leu Gln Ala Ala Asn Leu Gly Gln
 1               5                  10                  15

Asp Asp Glu Val Arg Ile Leu Leu Ala Ala Gly Ala Asp Val Asn Ala
                 20                  25                  30

Lys Asp Ser Ile Gly Gln Thr Pro Leu His Trp Ala Ala Arg Arg Gly
            35                  40                  45

His Leu Glu Ile Val Glu Val Leu Leu Lys Ala Gly Ala Asp Val Asn
 50                  55                  60

Ala Lys Asp Glu Tyr Gly Val Thr Pro Leu His Leu Ala Ala Ser Leu
 65                  70                  75                  80

Gly His Leu Glu Ile Val Glu Val Leu Leu Lys Ala Gly Ala Asp Val
                 85                  90                  95

Asn Ala Gln Asp Thr Ala Gly Gln Thr Pro Ala Asp Leu Ala Ala Asp
                100                 105                 110

Asp Gly His Glu Asp Ile Ala Val Val Leu Gln Lys Leu Asn
            115                 120                 125
```

<210> SEQ ID NO 79
<211> LENGTH: 126
<212> TYPE: PRT
<213> ORGANISM: Artificial
<220> FEATURE:
<223> OTHER INFORMATION: AR domain (one-domain)

<400> SEQUENCE: 79

```
Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                 20                  25                  30

Lys Asp Glu Tyr Gly Leu Thr Pro Leu Tyr Leu Ala Thr Ala His Gly
            35                  40                  45

His Leu Glu Ile Val Glu Val Leu Leu Lys Asn Gly Ala Asp Val Asn
 50                  55                  60

Ala Val Asp Ala Ile Gly Phe Thr Pro Leu His Leu Ala Ala Phe Ile
 65                  70                  75                  80

Gly His Leu Glu Ile Ala Glu Val Leu Leu Lys His Gly Ala Asp Val
                 85                  90                  95
```

-continued

Asn Ala Gln Asp Lys Phe Gly Lys Thr Ala Phe Asp Ile Ser Ile Gly
                100                 105                 110

Asn Gly Asn Glu Asp Leu Ala Glu Ile Leu Gln Lys Leu Asn
            115                 120                 125

<210> SEQ ID NO 80
<211> LENGTH: 126
<212> TYPE: PRT
<213> ORGANISM: Artificial
<220> FEATURE:
<223> OTHER INFORMATION: AR domain (one-domain)

<400> SEQUENCE: 80

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Glu Tyr Gly Leu Thr Pro Leu Tyr Leu Ala Thr Ala His Gly
        35                  40                  45

His Leu Glu Ile Val Glu Val Leu Leu Lys Asn Gly Ala Asp Val Asn
    50                  55                  60

Ala Val Asp Ala Ile Gly Phe Thr Pro Leu His Leu Ala Ala Phe Ile
65                  70                  75                  80

Gly His Leu Glu Ile Ala Glu Val Leu Leu Lys His Gly Ala Asp Val
                85                  90                  95

Asn Ala Gln Asp Lys Ser Gly Lys Thr Pro Ala Asp Leu Ala Ala Gly
                100                 105                 110

Ala Gly His Glu Asp Ile Ala Glu Val Leu Gln Lys Leu Asn
            115                 120                 125

<210> SEQ ID NO 81
<211> LENGTH: 126
<212> TYPE: PRT
<213> ORGANISM: Artificial
<220> FEATURE:
<223> OTHER INFORMATION: AR domain (one-domain)

<400> SEQUENCE: 81

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Glu Tyr Gly Leu Thr Pro Leu Tyr Leu Ala Thr Ala His Gly
        35                  40                  45

His Leu Glu Ile Val Glu Val Leu Leu Lys Ala Gly Ala Asp Val Asn
    50                  55                  60

Ala Val Asp Ala Ile Gly Phe Thr Pro Leu His Leu Ala Ala Phe Ile
65                  70                  75                  80

Gly His Leu Glu Ile Ala Glu Val Leu Leu Lys Ala Gly Ala Asp Val
                85                  90                  95

Asn Ala Gln Asp Lys Phe Gly Lys Thr Pro Ala Asp Ile Ala Ala Gly
                100                 105                 110

Ala Gly Asn Glu Asp Ile Ala Glu Val Leu Gln Lys Leu Asn
            115                 120                 125

<210> SEQ ID NO 82
<211> LENGTH: 159
<212> TYPE: PRT

<213> ORGANISM: Artificial
<220> FEATURE:
<223> OTHER INFORMATION: AR domain (one-domain)

<400> SEQUENCE: 82

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Thr Asp Ile His Gly His Thr Pro Leu His Leu Ala Ala Met Gly
        35                  40                  45

His Leu Glu Ile Val Glu Val Leu Leu Lys Asn Gly Ala Asp Val Asn
    50                  55                  60

Ala Asn Asp Trp Arg Gly Phe Thr Pro Leu His Leu Ala Ala Leu Asn
65                  70                  75                  80

Gly His Leu Glu Ile Val Glu Val Leu Leu Lys Asn Gly Ala Asp Val
                85                  90                  95

Asn Ala Thr Asp Thr Ala Gly Asn Thr Pro Leu His Leu Ala Ala Trp
            100                 105                 110

Phe Gly His Leu Glu Ile Val Glu Val Leu Leu Lys Asn Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Leu Asn
145                 150                 155

<210> SEQ ID NO 83
<211> LENGTH: 270
<212> TYPE: PRT
<213> ORGANISM: Artificial
<220> FEATURE:
<223> OTHER INFORMATION: AR domain (two-domain)

<400> SEQUENCE: 83

Gly Ser Asp Leu Gly Asp Lys Leu Leu Gln Ser Asp Leu Gly Ile Lys
1               5                   10                  15

Leu Leu Phe Ala Ala Lys Ser Gln Asp Asp Glu Val Arg Ile Leu
            20                  25                  30

Leu Ala Ala Gly Ala Asp Val Asn Ala Lys Asp Phe Gln Ser Val Thr
        35                  40                  45

Pro Leu His Ile Ala Ala Gln Ser Gly His Leu Glu Ile Val Glu Val
    50                  55                  60

Leu Leu Lys Ala Gly Ala Asp Val Asn Ala Lys Asp Val Thr Gly Asp
65                  70                  75                  80

Thr Pro Leu His Leu Ala Ala Gln His Gly His Leu Glu Ile Val Glu
                85                  90                  95

Val Leu Leu Lys Ala Gly Ala Asp Val Asn Ala Gln Asp Glu Arg Gly
            100                 105                 110

Trp Thr Pro Ala Asp Leu Ala Ala Asp Trp Gly His Glu Asp Ile Ala
        115                 120                 125

Glu Val Leu Gln Lys Leu Gly Gly Gly Ser Gly Gly Gly Ser
    130                 135                 140

Arg Ser Asp Leu Gly Ile Lys Leu Leu Gln Ala Ala Asn Leu Gly Gln
145                 150                 155                 160

Asp Asp Glu Val Arg Ile Leu Leu Ala Thr Gly Ala Asp Val Asn Ala
                165                 170                 175

Lys Asp Ser Ile Gly Gln Thr Pro Leu His Trp Ala Ala Arg Arg Gly
            180                 185                 190

His Leu Glu Ile Val Glu Val Leu Lys Ala Gly Ala Asp Val Asn
        195                 200                 205

Ala Lys Asp Glu Tyr Gly Val Thr Pro Leu His Leu Ala Ala Ser Leu
    210                 215                 220

Gly His Leu Glu Ile Val Glu Val Leu Leu Lys Ala Gly Ala Asp Val
225                 230                 235                 240

Asn Ala Gln Asp Glu Ser Gly Glu Thr Pro Ala Asp Leu Ala Ala Leu
                245                 250                 255

His Gly His Glu Asp Ile Ala Glu Val Leu Gln Lys Leu Asn
        260                 265                 270

<210> SEQ ID NO 84
<211> LENGTH: 237
<212> TYPE: PRT
<213> ORGANISM: Artificial
<220> FEATURE:
<223> OTHER INFORMATION: AR domain (two-domain)

<400> SEQUENCE: 84

Gly Ser Asp Leu Gly Asp Lys Leu Leu Gln Ser Asp Leu Gly Ile Lys
1               5                   10                  15

Leu Leu Phe Ala Ala Ala Lys Ser Gln Asp Asp Glu Val Arg Ile Leu
            20                  25                  30

Leu Ala Ala Gly Ala Asp Val Asn Ala Lys Asp Phe Gln Ser Val Thr
        35                  40                  45

Pro Leu His Ile Ala Ala Gln Ser Gly His Leu Glu Ile Val Glu Val
    50                  55                  60

Leu Leu Lys Ala Gly Ala Asp Val Asn Ala Lys Asp Val Thr Gly Asp
65                  70                  75                  80

Thr Pro Leu His Leu Ala Ala Gln His Gly His Leu Glu Ile Val Glu
                85                  90                  95

Val Leu Leu Lys Ala Gly Ala Asp Val Asn Ala Gln Asp Glu Arg Gly
            100                 105                 110

Trp Thr Pro Ala Asp Leu Ala Ala Asp Trp Gly His Glu Asp Ile Ala
        115                 120                 125

Glu Val Leu Gln Lys Leu Gly Gly Gly Ser Gly Gly Gly Gly Ser
    130                 135                 140

Arg Ser Asp Leu Gly Ala Lys Leu Leu Val Ala Ala Thr Ser Gly Gln
145                 150                 155                 160

Asp Asp Glu Val Arg Ile Leu Leu Ala Ala Gly Ala Asp Val Asn Ala
                165                 170                 175

Lys Asp Arg Ile Gly Phe Thr Pro Leu His Arg Ala Ala Phe Val Gly
            180                 185                 190

His Leu Glu Ile Val Glu Val Leu Leu Lys Ala Gly Ala Asp Val Asn
        195                 200                 205

Ala Gln Asp Asp Phe Gly His Thr Pro Ala Asp Leu Ala Ala Ser Leu
    210                 215                 220

Gly His Glu Asp Ile Ala Glu Val Leu Gln Lys Leu Asn
225                 230                 235

<210> SEQ ID NO 85
<211> LENGTH: 270
<212> TYPE: PRT
<213> ORGANISM: Artificial
<220> FEATURE:

<223> OTHER INFORMATION: AR domain (two-domain)

<400> SEQUENCE: 85

Gly Ser Asp Leu Gly Asp Lys Leu Leu Gln Ser Asp Leu Gly Ile Lys
1               5                   10                  15

Leu Leu Phe Ala Ala Lys Ser Gln Asp Asp Glu Val Arg Ile Leu
            20                  25                  30

Leu Ala Ala Gly Ala Asp Val Asn Ala Lys Asp Phe Gln Ser Val Thr
        35                  40                  45

Pro Leu His Ile Ala Ala Gln Ser Gly His Leu Glu Ile Val Glu Val
    50                  55                  60

Leu Leu Lys Ala Gly Ala Asp Val Asn Ala Lys Asp Val Thr Gly Asp
65                  70                  75                  80

Thr Pro Leu His Leu Ala Ala Gln His Gly His Leu Glu Ile Val Glu
                85                  90                  95

Val Leu Leu Lys Ala Gly Ala Asp Val Asn Ala Gln Asp Glu Arg Gly
            100                 105                 110

Trp Thr Pro Ala Asp Leu Ala Ala Asp Trp Gly His Glu Asp Ile Ala
        115                 120                 125

Glu Val Leu Gln Lys Leu Gly Gly Gly Ser Gly Gly Gly Gly Ser
    130                 135                 140

Arg Ser Asp Leu Gly Lys Lys Leu Leu Glu Ala Ala Arg Ala Gly Gln
145                 150                 155                 160

Asp Asp Glu Val Arg Ile Leu Met Ala Asn Gly Ala Asp Val Asn Ala
                165                 170                 175

Lys Asp Glu Tyr Gly Leu Thr Pro Leu Tyr Leu Ala Thr Ala His Gly
            180                 185                 190

His Leu Glu Ile Val Glu Val Leu Leu Lys Asn Gly Ala Asp Val Asn
        195                 200                 205

Ala Val Asp Ala Ile Gly Phe Thr Pro Leu His Leu Ala Ala Phe Ile
    210                 215                 220

Gly His Leu Glu Ile Ala Glu Val Leu Leu Lys His Gly Ala Asp Val
225                 230                 235                 240

Asn Ala Gln Asp Lys Phe Gly Lys Thr Ala Phe Asp Ile Ser Ile Gly
                245                 250                 255

Asn Gly Asn Glu Asp Leu Ala Glu Ile Leu Gln Lys Leu Asn
            260                 265                 270

<210> SEQ ID NO 86
<211> LENGTH: 272
<212> TYPE: PRT
<213> ORGANISM: Artificial
<220> FEATURE:
<223> OTHER INFORMATION: AR domain (two-domain)

<400> SEQUENCE: 86

Gly Ser Asp Leu Gly Ile Lys Leu Leu Phe Ala Ala Lys Gly Gln
1               5                   10                  15

Asp Asp Glu Val Arg Glu Leu Leu Lys Ala Gly Ala Asp Val Asn Ala
                20                  25                  30

Lys Asp Phe Gln Gly Val Thr Pro Leu His Ile Ala Ala Gln Ser Gly
            35                  40                  45

His Leu Glu Ile Val Glu Val Leu Leu Lys Ala Gly Ala Asp Val Asn
        50                  55                  60

Ala Lys Asp Val Thr Gly Asp Thr Pro Leu His Leu Ala Ala Gln His
65                  70                  75                  80

Gly His Leu Glu Ile Val Glu Val Leu Leu Lys Ala Gly Ala Asp Val
                85                  90                  95

Asn Ala Gln Asp Glu Arg Gly Trp Thr Pro Ala Asp Leu Ala Ala Asp
            100                 105                 110

Trp Gly His Glu Asp Ile Ala Glu Val Leu Gln Lys Ala Ala Gly Gly
        115                 120                 125

Gly Gly Ser Gly Gly Gly Ser Gly Gly Gly Ser Gly Gly Gly
    130                 135                 140

Gly Ser Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
                165                 170                 175

Asn Ala Lys Asp Glu Tyr Gly Leu Thr Pro Leu Tyr Leu Ala Thr Ala
            180                 185                 190

His Gly His Leu Glu Ile Val Glu Val Leu Leu Lys Ala Gly Ala Asp
        195                 200                 205

Val Asn Ala Val Asp Ala Ile Gly Phe Thr Pro Leu His Leu Ala Ala
    210                 215                 220

Phe Ile Gly His Leu Glu Ile Ala Glu Val Leu Leu Lys Ala Gly Ala
225                 230                 235                 240

Asp Val Asn Ala Gln Asp Lys Phe Gly Lys Thr Pro Ala Asp Ile Ala
                245                 250                 255

Ala Gly Ala Gly Asn Glu Asp Ile Ala Glu Val Leu Gln Lys Ala Ala
            260                 265                 270

<210> SEQ ID NO 87
<211> LENGTH: 274
<212> TYPE: PRT
<213> ORGANISM: Artificial
<220> FEATURE:
<223> OTHER INFORMATION: AR domain (two-domain)

<400> SEQUENCE: 87

Gly Ser Asp Leu Gly Ile Lys Leu Leu Phe Ala Ala Lys Gly Gln
1               5                   10                  15

Asp Asp Glu Val Arg Glu Leu Leu Lys Ala Gly Ala Asp Val Asn Ala
                20                  25                  30

Lys Asp Phe Gln Gly Val Thr Pro Leu His Ile Ala Ala Gln Ser Gly
            35                  40                  45

His Leu Glu Ile Val Glu Val Leu Leu Lys Ala Gly Ala Asp Val Asn
        50                  55                  60

Ala Lys Asp Val Thr Gly Asp Thr Pro Leu His Leu Ala Ala Gln His
65                  70                  75                  80

Gly His Leu Glu Ile Val Glu Val Leu Leu Lys Ala Gly Ala Asp Val
                85                  90                  95

Asn Ala Gln Asp Glu Arg Gly Trp Thr Pro Ala Asp Leu Ala Ala Asp
            100                 105                 110

Trp Gly His Glu Asp Ile Ala Glu Val Leu Gln Lys Ala Ala Gly Ser
        115                 120                 125

Pro Thr Pro Thr Pro Thr Thr Pro Thr Pro Thr Pro Thr Thr Pro Thr
130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

```
Asp Val Asn Ala Lys Asp Glu Tyr Gly Leu Thr Pro Leu Tyr Leu Ala
            180                 185                 190

Thr Ala His Gly His Leu Glu Ile Val Glu Val Leu Leu Lys Ala Gly
        195                 200                 205

Ala Asp Val Asn Ala Val Asp Ala Ile Gly Phe Thr Pro Leu His Leu
210                 215                 220

Ala Ala Phe Ile Gly His Leu Glu Ile Ala Glu Val Leu Leu Lys Ala
225                 230                 235                 240

Gly Ala Asp Val Asn Ala Gln Asp Lys Phe Gly Lys Thr Pro Ala Asp
                245                 250                 255

Ile Ala Ala Gly Ala Gly Asn Glu Asp Ile Ala Glu Val Leu Gln Lys
            260                 265                 270

Ala Ala

<210> SEQ ID NO 88
<211> LENGTH: 261
<212> TYPE: PRT
<213> ORGANISM: Artificial
<220> FEATURE:
<223> OTHER INFORMATION: AR domain (two-domain)

<400> SEQUENCE: 88

Gly Ser Asp Leu Gly Val Lys Leu Leu Trp Ala Ala Ala Arg Gly Gln
1               5                   10                  15

Asp Asp Glu Val Arg Ile Leu Leu Ala Ala Gly Ala Asp Val Asn Ala
                20                  25                  30

Lys Asp Phe Gln Gly Ile Thr Pro Leu His Ile Ala Ala Thr Asn Gly
            35                  40                  45

His Leu Glu Ile Val Glu Val Leu Leu Lys Ala Gly Ala Asp Val Asn
        50                  55                  60

Ala Lys Asp Ile Thr Gly Glu Thr Pro Leu His His Ala Ala Asp Ser
65                  70                  75                  80

Gly His Leu Glu Ile Val Glu Val Leu Leu Lys Ala Gly Ala Asp Val
                85                  90                  95

Asn Ala Gln Asp Lys Ala Gly Val Thr Pro Ala Asp Leu Ala Ala Ala
                100                 105                 110

Trp Gly His Glu Asp Ile Ala Glu Val Leu Gln Lys Leu Gly Gly Gly
            115                 120                 125

Gly Ser Gly Gly Gly Gly Ser Arg Ser Asp Leu Gly Ile Lys Leu Leu
130                 135                 140

Gln Ala Ala Asn Leu Gly Gln Asp Asp Glu Val Arg Ile Leu Leu Ala
145                 150                 155                 160

Thr Gly Ala Asp Val Asn Ala Lys Asp Ser Ile Gly Gln Thr Pro Leu
                165                 170                 175

His Trp Ala Ala Arg Arg Gly His Leu Glu Ile Val Glu Val Leu Leu
            180                 185                 190

Lys Ala Gly Ala Asp Val Asn Ala Lys Asp Glu Tyr Gly Val Thr Pro
        195                 200                 205

Leu His Leu Ala Ala Ser Leu Gly His Leu Glu Ile Val Glu Val Leu
    210                 215                 220

Leu Lys Ala Gly Ala Asp Val Asn Ala Gln Asp Glu Ser Gly Glu Thr
225                 230                 235                 240

Pro Ala Asp Leu Ala Ala Leu His Gly His Glu Asp Ile Ala Glu Val
                245                 250                 255
```

Leu Gln Lys Leu Asn
        260

<210> SEQ ID NO 89
<211> LENGTH: 228
<212> TYPE: PRT
<213> ORGANISM: Artificial
<220> FEATURE:
<223> OTHER INFORMATION: AR domain (two-domain)

<400> SEQUENCE: 89

Gly Ser Asp Leu Gly Val Lys Leu Leu Trp Ala Ala Ala Arg Gly Gln
1               5                   10                  15

Asp Asp Glu Val Arg Ile Leu Leu Ala Ala Gly Ala Asp Val Asn Ala
            20                  25                  30

Lys Asp Phe Gln Gly Ile Thr Pro Leu His Ile Ala Ala Thr Asn Gly
        35                  40                  45

His Leu Glu Ile Val Glu Val Leu Leu Lys Ala Gly Ala Asp Val Asn
50                  55                  60

Ala Lys Asp Ile Thr Gly Glu Thr Pro Leu His His Ala Ala Asp Ser
65                  70                  75                  80

Gly His Leu Glu Ile Val Glu Val Leu Leu Lys Ala Gly Ala Asp Val
                85                  90                  95

Asn Ala Gln Asp Lys Ala Gly Val Thr Pro Ala Asp Leu Ala Ala Ala
            100                 105                 110

Trp Gly His Glu Asp Ile Ala Glu Val Leu Gln Lys Leu Gly Gly Gly
        115                 120                 125

Gly Ser Gly Gly Gly Ser Arg Ser Asp Leu Gly Ala Lys Leu Leu
    130                 135                 140

Val Ala Ala Thr Ser Gly Gln Asp Asp Glu Val Arg Ile Leu Leu Ala
145                 150                 155                 160

Ala Gly Ala Asp Val Asn Ala Lys Asp Arg Ile Gly Phe Thr Pro Leu
                165                 170                 175

His Arg Ala Ala Phe Val Gly His Leu Glu Ile Val Glu Val Leu Leu
            180                 185                 190

Lys Ala Gly Ala Asp Val Asn Ala Gln Asp Phe Gly His Thr Pro
        195                 200                 205

Ala Asp Leu Ala Ala Ser Leu Gly His Glu Asp Ile Ala Glu Val Leu
    210                 215                 220

Gln Lys Leu Asn
225

<210> SEQ ID NO 90
<211> LENGTH: 261
<212> TYPE: PRT
<213> ORGANISM: Artificial
<220> FEATURE:
<223> OTHER INFORMATION: AR domain (two-domain)

<400> SEQUENCE: 90

Gly Ser Asp Leu Gly Val Lys Leu Leu Trp Ala Ala Ala Arg Gly Gln
1               5                   10                  15

Asp Asp Glu Val Arg Ile Leu Leu Ala Ala Gly Ala Asp Val Asn Ala
            20                  25                  30

Lys Asp Phe Gln Gly Ile Thr Pro Leu His Ile Ala Ala Thr Asn Gly
        35                  40                  45

His Leu Glu Ile Val Glu Val Leu Leu Lys Ala Gly Ala Asp Val Asn
50                  55                  60

```
Ala Lys Asp Ile Thr Gly Glu Thr Pro Leu His His Ala Ala Asp Ser
 65                  70                  75                  80

Gly His Leu Glu Ile Val Glu Val Leu Leu Lys Ala Gly Ala Asp Val
                 85                  90                  95

Asn Ala Gln Asp Lys Ala Gly Val Thr Pro Ala Asp Leu Ala Ala Ala
                100                 105                 110

Trp Gly His Glu Asp Ile Ala Glu Val Leu Gln Lys Leu Gly Gly Gly
            115                 120                 125

Gly Ser Gly Gly Gly Ser Arg Ser Asp Leu Gly Lys Lys Leu Leu
130                 135                 140

Glu Ala Ala Arg Ala Gly Gln Asp Asp Glu Val Arg Ile Leu Met Ala
145                 150                 155                 160

Asn Gly Ala Asp Val Asn Ala Lys Asp Glu Tyr Gly Leu Thr Pro Leu
                165                 170                 175

Tyr Leu Ala Thr Ala His Gly His Leu Glu Ile Val Glu Val Leu Leu
            180                 185                 190

Lys Asn Gly Ala Asp Val Asn Ala Val Asp Ala Ile Gly Phe Thr Pro
            195                 200                 205

Leu His Leu Ala Ala Phe Ile Gly His Leu Glu Ile Ala Glu Val Leu
    210                 215                 220

Leu Lys His Gly Ala Asp Val Asn Ala Gln Asp Lys Phe Gly Lys Thr
225                 230                 235                 240

Ala Phe Asp Ile Ser Ile Gly Asn Gly Asn Glu Asp Leu Ala Glu Ile
                245                 250                 255

Leu Gln Lys Leu Asn
            260

<210> SEQ ID NO 91
<211> LENGTH: 272
<212> TYPE: PRT
<213> ORGANISM: Artificial
<220> FEATURE:
<223> OTHER INFORMATION: AR domain (two-domain)

<400> SEQUENCE: 91

Gly Ser Asp Leu Gly Val Lys Leu Leu Trp Ala Ala Ala Arg Gly Gln
 1               5                  10                  15

Asp Asp Glu Val Arg Glu Leu Leu Lys Ala Gly Ala Asp Val Asn Ala
                 20                  25                  30

Lys Asp Phe Gln Gly Ile Thr Pro Leu His Ile Ala Ala Thr Asn Gly
             35                  40                  45

His Leu Glu Ile Val Glu Val Leu Leu Lys Ala Gly Ala Asp Val Asn
 50                  55                  60

Ala Lys Asp Ile Thr Gly Glu Thr Pro Leu His His Ala Ala Asp Ser
 65                  70                  75                  80

Gly His Leu Glu Ile Val Glu Val Leu Leu Lys Ala Gly Ala Asp Val
                 85                  90                  95

Asn Ala Gln Asp Lys Ala Gly Val Thr Pro Ala Asp Leu Ala Ala Ala
                100                 105                 110

Trp Gly His Glu Asp Ile Ala Glu Val Leu Gln Lys Ala Ala Gly Gly
            115                 120                 125

Gly Gly Ser Gly Gly Gly Gly Ser Gly Gly Gly Ser Gly Gly Gly
130                 135                 140

Gly Ser Gly Ser Asp Leu Gly Lys Lys Leu Leu Glu Ala Ala Arg Ala
145                 150                 155                 160
```

Gly Gln Asp Asp Glu Val Arg Glu Leu Leu Lys Ala Gly Ala Asp Val
            165                 170                 175

Asn Ala Lys Asp Glu Tyr Gly Leu Thr Pro Leu Tyr Leu Ala Thr Ala
            180                 185                 190

His Gly His Leu Glu Ile Val Glu Val Leu Leu Lys Ala Gly Ala Asp
            195                 200                 205

Val Asn Ala Val Asp Ala Ile Gly Phe Thr Pro Leu His Leu Ala Ala
            210                 215                 220

Phe Ile Gly His Leu Glu Ile Ala Glu Val Leu Leu Lys Ala Gly Ala
225                 230                 235                 240

Asp Val Asn Ala Gln Asp Lys Phe Gly Lys Thr Pro Ala Asp Ile Ala
            245                 250                 255

Ala Gly Ala Gly Asn Glu Asp Ile Ala Glu Val Leu Gln Lys Ala Ala
            260                 265                 270

<210> SEQ ID NO 92
<211> LENGTH: 274
<212> TYPE: PRT
<213> ORGANISM: Artificial
<220> FEATURE:
<223> OTHER INFORMATION: AR domain (two-domain)

<400> SEQUENCE: 92

Gly Ser Asp Leu Gly Val Lys Leu Leu Trp Ala Ala Ala Arg Gly Gln
1               5                   10                  15

Asp Asp Glu Val Arg Glu Leu Leu Lys Ala Gly Ala Asp Val Asn Ala
            20                  25                  30

Lys Asp Phe Gln Gly Ile Thr Pro Leu His Ile Ala Ala Thr Asn Gly
            35                  40                  45

His Leu Glu Ile Val Glu Val Leu Leu Lys Ala Gly Ala Asp Val Asn
        50                  55                  60

Ala Lys Asp Ile Thr Gly Glu Thr Pro Leu His His Ala Ala Asp Ser
65                  70                  75                  80

Gly His Leu Glu Ile Val Glu Val Leu Leu Lys Ala Gly Ala Asp Val
            85                  90                  95

Asn Ala Gln Asp Lys Ala Gly Val Thr Pro Ala Asp Leu Ala Ala Ala
            100                 105                 110

Trp Gly His Glu Asp Ile Ala Glu Val Leu Gln Lys Ala Ala Gly Ser
            115                 120                 125

Pro Thr Pro Thr Pro Thr Thr Pro Thr Pro Thr Thr Pro Thr
            130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
            165                 170                 175

Asp Val Asn Ala Lys Asp Glu Tyr Gly Leu Thr Pro Leu Tyr Leu Ala
            180                 185                 190

Thr Ala His Gly His Leu Glu Ile Val Glu Val Leu Leu Lys Ala Gly
            195                 200                 205

Ala Asp Val Asn Ala Val Asp Ala Ile Gly Phe Thr Pro Leu His Leu
            210                 215                 220

Ala Ala Phe Ile Gly His Leu Glu Ile Ala Glu Val Leu Leu Lys Ala
225                 230                 235                 240

Gly Ala Asp Val Asn Ala Gln Asp Lys Phe Gly Lys Thr Pro Ala Asp
            245                 250                 255

Ile Ala Ala Gly Ala Gly Asn Glu Asp Ile Ala Glu Val Leu Gln Lys
          260                 265                 270

Ala Ala

<210> SEQ ID NO 93
<211> LENGTH: 261
<212> TYPE: PRT
<213> ORGANISM: Artificial
<220> FEATURE:
<223> OTHER INFORMATION: AR domain (two-domain)

<400> SEQUENCE: 93

Gly Ser Asp Leu Gly Ile Lys Leu Leu Phe Ala Ala Ser Arg Gly Gln
1               5                   10                  15

Asp Asp Glu Val Arg Ile Leu Leu Ala Ala Gly Ala Asp Val Asn Ala
            20                  25                  30

Lys Asp Phe Glu Gly Ile Thr Pro Leu His Ala Ala Ala Arg Ser Gly
        35                  40                  45

His Leu Glu Ile Val Glu Val Leu Leu Lys Ala Gly Ala Asp Val Asn
    50                  55                  60

Ala Lys Asp Val Glu Gly Trp Thr Pro Leu His Tyr Ala Ala Ser Tyr
65                  70                  75                  80

Gly His Leu Glu Ile Val Glu Val Leu Leu Lys Ala Gly Ala Asp Val
                85                  90                  95

Asn Ala Gln Asp Asn His Gly Ala Thr Pro Ala Asp Leu Ala Ala Gln
            100                 105                 110

Trp Gly His Glu Asp Ile Ala Glu Val Leu Gln Lys Leu Gly Gly Gly
        115                 120                 125

Gly Ser Gly Gly Gly Ser Arg Ser Asp Leu Gly Ile Lys Leu Leu
    130                 135                 140

Gln Ala Ala Asn Leu Gly Gln Asp Asp Glu Val Arg Ile Leu Leu Ala
145                 150                 155                 160

Thr Gly Ala Asp Val Asn Ala Lys Asp Ser Ile Gly Gln Thr Pro Leu
                165                 170                 175

His Trp Ala Ala Arg Arg Gly His Leu Glu Ile Val Glu Val Leu Leu
            180                 185                 190

Lys Ala Gly Ala Asp Val Asn Ala Lys Asp Glu Tyr Gly Val Thr Pro
        195                 200                 205

Leu His Leu Ala Ala Ser Leu Gly His Leu Glu Ile Val Glu Val Leu
    210                 215                 220

Leu Lys Ala Gly Ala Asp Val Asn Ala Gln Asp Glu Ser Gly Glu Thr
225                 230                 235                 240

Pro Ala Asp Leu Ala Ala Leu His Gly His Glu Asp Ile Ala Glu Val
                245                 250                 255

Leu Gln Lys Leu Asn
            260

<210> SEQ ID NO 94
<211> LENGTH: 228
<212> TYPE: PRT
<213> ORGANISM: Artificial
<220> FEATURE:
<223> OTHER INFORMATION: AR domain (two-domain)

<400> SEQUENCE: 94

Gly Ser Asp Leu Gly Ile Lys Leu Leu Phe Ala Ala Ser Arg Gly Gln
1               5                   10                  15

Asp Asp Glu Val Arg Ile Leu Leu Ala Ala Gly Ala Asp Val Asn Ala
            20                  25                  30

Lys Asp Phe Glu Gly Ile Thr Pro Leu His Ala Ala Arg Ser Gly
        35                  40                  45

His Leu Glu Ile Val Glu Val Leu Leu Lys Ala Gly Ala Asp Val Asn
 50                  55                  60

Ala Lys Asp Val Glu Gly Trp Thr Pro Leu His Tyr Ala Ala Ser Tyr
65                  70                  75                  80

Gly His Leu Glu Ile Val Glu Val Leu Leu Lys Ala Gly Ala Asp Val
                85                  90                  95

Asn Ala Gln Asp Asn His Gly Ala Thr Pro Ala Asp Leu Ala Ala Gln
                100                 105                 110

Trp Gly His Glu Asp Ile Ala Glu Val Leu Gln Lys Leu Gly Gly Gly
            115                 120                 125

Gly Ser Gly Gly Gly Gly Ser Arg Ser Asp Leu Gly Ala Lys Leu Leu
130                 135                 140

Val Ala Ala Thr Ser Gly Gln Asp Asp Glu Val Arg Ile Leu Leu Ala
145                 150                 155                 160

Ala Gly Ala Asp Val Asn Ala Lys Asp Arg Ile Gly Phe Thr Pro Leu
                165                 170                 175

His Arg Ala Ala Phe Val Gly His Leu Glu Ile Val Glu Val Leu Leu
            180                 185                 190

Lys Ala Gly Ala Asp Val Asn Ala Gln Asp Phe Gly His Thr Pro
            195                 200                 205

Ala Asp Leu Ala Ala Ser Leu Gly His Glu Asp Ile Ala Glu Val Leu
    210                 215                 220

Gln Lys Leu Asn
225

<210> SEQ ID NO 95
<211> LENGTH: 261
<212> TYPE: PRT
<213> ORGANISM: Artificial
<220> FEATURE:
<223> OTHER INFORMATION: AR domain (two-domain)

<400> SEQUENCE: 95

Gly Ser Asp Leu Gly Ile Lys Leu Leu Phe Ala Ala Ser Arg Gly Gln
1               5                   10                  15

Asp Asp Glu Val Arg Ile Leu Leu Ala Ala Gly Ala Asp Val Asn Ala
            20                  25                  30

Lys Asp Phe Glu Gly Ile Thr Pro Leu His Ala Ala Arg Ser Gly
        35                  40                  45

His Leu Glu Ile Val Glu Val Leu Leu Lys Ala Gly Ala Asp Val Asn
 50                  55                  60

Ala Lys Asp Val Glu Gly Trp Thr Pro Leu His Tyr Ala Ala Ser Tyr
65                  70                  75                  80

Gly His Leu Glu Ile Val Glu Val Leu Leu Lys Ala Gly Ala Asp Val
                85                  90                  95

Asn Ala Gln Asp Asn His Gly Ala Thr Pro Ala Asp Leu Ala Ala Gln
                100                 105                 110

Trp Gly His Glu Asp Ile Ala Glu Val Leu Gln Lys Leu Gly Gly Gly
            115                 120                 125

Gly Ser Gly Gly Gly Gly Ser Arg Ser Asp Leu Gly Lys Lys Leu Leu
130                 135                 140

Glu Ala Ala Arg Ala Gly Gln Asp Asp Glu Val Arg Ile Leu Met Ala
145                 150                 155                 160

Asn Gly Ala Asp Val Asn Ala Lys Asp Glu Tyr Gly Leu Thr Pro Leu
                165                 170                 175

Tyr Leu Ala Thr Ala His Gly His Leu Glu Ile Val Glu Val Leu Leu
            180                 185                 190

Lys Asn Gly Ala Asp Val Asn Ala Val Asp Ala Ile Gly Phe Thr Pro
            195                 200                 205

Leu His Leu Ala Ala Phe Ile Gly His Leu Glu Ile Ala Glu Val Leu
            210                 215                 220

Leu Lys His Gly Ala Asp Val Asn Ala Gln Asp Lys Phe Gly Lys Thr
225                 230                 235                 240

Ala Phe Asp Ile Ser Ile Gly Asn Gly Asn Glu Asp Leu Ala Glu Ile
                245                 250                 255

Leu Gln Lys Leu Asn
            260

<210> SEQ ID NO 96
<211> LENGTH: 261
<212> TYPE: PRT
<213> ORGANISM: Artificial
<220> FEATURE:
<223> OTHER INFORMATION: AR domain (two-domain)

<400> SEQUENCE: 96

Gly Ser Asp Leu Gly Ile Lys Leu Leu Phe Ala Ala Ala Lys Gly Gln
1               5                   10                  15

Asp Asp Glu Val Arg Ile Leu Leu Ala Ala Gly Ala Asp Val Asn Ala
                20                  25                  30

Lys Asp Phe Glu Gly Tyr Thr Pro Leu His Val Ala Ala Tyr Asp Gly
            35                  40                  45

His Leu Glu Ile Val Glu Val Leu Leu Lys Ala Gly Ala Asp Val Asn
        50                  55                  60

Ala Lys Asp Ser Gln Gly Arg Thr Pro Leu His Glu Ala Ala Tyr Ser
65                  70                  75                  80

Gly His Leu Glu Ile Val Glu Val Leu Leu Lys Ala Gly Ala Asp Val
                85                  90                  95

Asn Ala Gln Asp Asp Ala Gly Glu Thr Pro Ala Asp Leu Ala Ala Ala
                100                 105                 110

Trp Gly His Glu Asp Ile Ala Glu Val Leu Gln Lys Leu Gly Gly Gly
            115                 120                 125

Gly Ser Gly Gly Gly Gly Ser Arg Ser Asp Leu Gly Ile Lys Leu Leu
130                 135                 140

Gln Ala Ala Asn Leu Gly Gln Asp Asp Glu Val Arg Ile Leu Leu Ala
145                 150                 155                 160

Thr Gly Ala Asp Val Asn Ala Lys Asp Ser Ile Gly Gln Thr Pro Leu
                165                 170                 175

His Trp Ala Ala Arg Arg Gly His Leu Glu Ile Val Glu Val Leu Leu
            180                 185                 190

Lys Ala Gly Ala Asp Val Asn Ala Lys Asp Glu Tyr Gly Val Thr Pro
            195                 200                 205

Leu His Leu Ala Ala Ser Leu Gly His Leu Glu Ile Val Glu Val Leu
            210                 215                 220

Leu Lys Ala Gly Ala Asp Val Asn Ala Gln Asp Glu Ser Gly Glu Thr
225                 230                 235                 240

Pro Ala Asp Leu Ala Ala Leu His Gly His Glu Asp Ile Ala Glu Val
            245                 250                 255

Leu Gln Lys Leu Asn
            260

<210> SEQ ID NO 97
<211> LENGTH: 228
<212> TYPE: PRT
<213> ORGANISM: Artificial
<220> FEATURE:
<223> OTHER INFORMATION: AR domain (two-domain)

<400> SEQUENCE: 97

Gly Ser Asp Leu Gly Ile Lys Leu Leu Phe Ala Ala Lys Gly Gln
1               5                   10                  15

Asp Asp Glu Val Arg Ile Leu Leu Ala Ala Gly Ala Asp Val Asn Ala
                20                  25                  30

Lys Asp Phe Glu Gly Tyr Thr Pro Leu His Val Ala Ala Tyr Asp Gly
            35                  40                  45

His Leu Glu Ile Val Glu Val Leu Leu Lys Ala Gly Ala Asp Val Asn
50                  55                  60

Ala Lys Asp Ser Gln Gly Arg Thr Pro Leu His Glu Ala Ala Tyr Ser
65                  70                  75                  80

Gly His Leu Glu Ile Val Glu Val Leu Leu Lys Ala Gly Ala Asp Val
                85                  90                  95

Asn Ala Gln Asp Asp Ala Gly Glu Thr Pro Ala Asp Leu Ala Ala Ala
                100                 105                 110

Trp Gly His Glu Asp Ile Ala Glu Val Leu Gln Lys Leu Gly Gly Gly
            115                 120                 125

Gly Ser Gly Gly Gly Ser Arg Ser Asp Leu Gly Ala Lys Leu Leu
            130                 135                 140

Val Ala Ala Thr Ser Gly Gln Asp Asp Glu Val Arg Ile Leu Leu Ala
145                 150                 155                 160

Ala Gly Ala Asp Val Asn Ala Lys Asp Arg Ile Gly Phe Thr Pro Leu
                165                 170                 175

His Arg Ala Ala Phe Val Gly His Leu Glu Ile Val Glu Val Leu Leu
            180                 185                 190

Lys Ala Gly Ala Asp Val Asn Ala Gln Asp Asp Phe Gly His Thr Pro
            195                 200                 205

Ala Asp Leu Ala Ala Ser Leu Gly His Glu Asp Ile Ala Glu Val Leu
            210                 215                 220

Gln Lys Leu Asn
225

<210> SEQ ID NO 98
<211> LENGTH: 261
<212> TYPE: PRT
<213> ORGANISM: Artificial
<220> FEATURE:
<223> OTHER INFORMATION: AR domain (two-domain)

<400> SEQUENCE: 98

Gly Ser Asp Leu Gly Ile Lys Leu Leu Phe Ala Ala Lys Gly Gln
1               5                   10                  15

Asp Asp Glu Val Arg Ile Leu Leu Ala Ala Gly Ala Asp Val Asn Ala
                20                  25                  30

Lys Asp Phe Glu Gly Tyr Thr Pro Leu His Val Ala Ala Tyr Asp Gly

```
              35                  40                  45
His Leu Glu Ile Val Glu Val Leu Lys Ala Gly Ala Asp Val Asn
 50                  55                  60

Ala Lys Asp Ser Gln Gly Arg Thr Pro Leu His Glu Ala Ala Tyr Ser
 65                  70                  75                  80

Gly His Leu Glu Ile Val Glu Val Leu Leu Lys Ala Gly Ala Asp Val
                     85                  90                  95

Asn Ala Gln Asp Asp Ala Gly Glu Thr Pro Ala Asp Leu Ala Ala Ala
                100                 105                 110

Trp Gly His Glu Asp Ile Ala Glu Val Leu Gln Lys Leu Gly Gly Gly
                115                 120                 125

Gly Ser Gly Gly Gly Ser Arg Ser Asp Leu Gly Lys Lys Leu Leu
130                 135                 140

Glu Ala Ala Arg Ala Gly Gln Asp Asp Glu Val Arg Ile Leu Met Ala
145                 150                 155                 160

Asn Gly Ala Asp Val Asn Ala Lys Asp Glu Tyr Gly Leu Thr Pro Leu
                165                 170                 175

Tyr Leu Ala Thr Ala His Gly His Leu Glu Ile Val Glu Val Leu Leu
                180                 185                 190

Lys Asn Gly Ala Asp Val Asn Ala Val Asp Ala Ile Gly Phe Thr Pro
                195                 200                 205

Leu His Leu Ala Ala Phe Ile Gly His Leu Glu Ile Ala Glu Val Leu
210                 215                 220

Leu Lys His Gly Ala Asp Val Asn Ala Gln Asp Lys Phe Gly Lys Thr
225                 230                 235                 240

Ala Phe Asp Ile Ser Ile Gly Asn Gly Asn Glu Asp Leu Ala Glu Ile
                245                 250                 255

Leu Gln Lys Leu Asn
            260

<210> SEQ ID NO 99
<211> LENGTH: 261
<212> TYPE: PRT
<213> ORGANISM: Artificial
<220> FEATURE:
<223> OTHER INFORMATION: AR domain (two-domain)

<400> SEQUENCE: 99

Gly Ser Asp Leu Gly His Lys Leu Leu Glu Ala Ala Val Ala Gly Gln
 1               5                  10                  15

Asp Asp Glu Val Arg Ile Leu Leu Ala Ala Gly Ala Asp Val Asn Ala
                 20                  25                  30

Lys Asp Trp Tyr Gly Lys Thr Pro Leu His Phe Ala Ala Gly Leu Gly
                 35                  40                  45

His Leu Glu Ile Val Glu Val Leu Leu Lys Ala Gly Ala Asp Val Asn
 50                  55                  60

Ala Lys Asp Glu Asp Gly Gln Thr Pro Leu His Leu Ala Ala Ala Tyr
 65                  70                  75                  80

Gly His Leu Glu Ile Val Glu Val Leu Leu Lys Ala Gly Ala Asp Val
                     85                  90                  95

Asn Ala Gln Asp Asn Asp Gly Phe Thr Pro Ala Asp Leu Ala Ala Asp
                100                 105                 110

Ser Gly His Glu Asp Ile Ala Glu Val Leu Gln Lys Leu Gly Gly Gly
                115                 120                 125

Gly Ser Gly Gly Gly Gly Ser Arg Ser Asp Leu Gly Ile Lys Leu Leu
```

```
              130                 135                 140
Gln Ala Ala Asn Leu Gly Gln Asp Asp Glu Val Arg Ile Leu Leu Ala
145                 150                 155                 160

Thr Gly Ala Asp Val Asn Ala Lys Asp Ser Ile Gly Gln Thr Pro Leu
                165                 170                 175

His Trp Ala Ala Arg Arg Gly His Leu Glu Ile Val Glu Val Leu Leu
                180                 185                 190

Lys Ala Gly Ala Asp Val Asn Ala Lys Asp Glu Tyr Gly Val Thr Pro
            195                 200                 205

Leu His Leu Ala Ala Ser Leu Gly His Leu Glu Ile Val Glu Val Leu
        210                 215                 220

Leu Lys Ala Gly Ala Asp Val Asn Ala Gln Asp Glu Ser Gly Glu Thr
225                 230                 235                 240

Pro Ala Asp Leu Ala Ala Leu His Gly His Glu Asp Ile Ala Glu Val
                245                 250                 255

Leu Gln Lys Leu Asn
            260

<210> SEQ ID NO 100
<211> LENGTH: 228
<212> TYPE: PRT
<213> ORGANISM: Artificial
<220> FEATURE:
<223> OTHER INFORMATION: AR domain (two-domain)

<400> SEQUENCE: 100

Gly Ser Asp Leu Gly His Lys Leu Leu Glu Ala Ala Val Ala Gly Gln
1               5                   10                  15

Asp Asp Glu Val Arg Ile Leu Leu Ala Ala Gly Ala Asp Val Asn Ala
                20                  25                  30

Lys Asp Trp Tyr Gly Lys Thr Pro Leu His Phe Ala Ala Gly Leu Gly
            35                  40                  45

His Leu Glu Ile Val Glu Val Leu Leu Lys Ala Gly Ala Asp Val Asn
        50                  55                  60

Ala Lys Asp Glu Asp Gly Gln Thr Pro Leu His Leu Ala Ala Ala Tyr
65                  70                  75                  80

Gly His Leu Glu Ile Val Glu Val Leu Leu Lys Ala Gly Ala Asp Val
                85                  90                  95

Asn Ala Gln Asp Asn Asp Gly Phe Thr Pro Ala Asp Leu Ala Ala Asp
                100                 105                 110

Ser Gly His Glu Asp Ile Ala Glu Val Leu Gln Lys Leu Gly Gly Gly
            115                 120                 125

Gly Ser Gly Gly Gly Gly Ser Arg Ser Asp Leu Gly Ala Lys Leu Leu
        130                 135                 140

Val Ala Ala Thr Ser Gly Gln Asp Asp Glu Val Arg Ile Leu Leu Ala
145                 150                 155                 160

Ala Gly Ala Asp Val Asn Ala Lys Asp Arg Ile Gly Phe Thr Pro Leu
                165                 170                 175

His Arg Ala Ala Phe Val Gly His Leu Glu Ile Val Glu Val Leu Leu
                180                 185                 190

Lys Ala Gly Ala Asp Val Asn Ala Gln Asp Asp Phe Gly His Thr Pro
            195                 200                 205

Ala Asp Leu Ala Ala Ser Leu Gly His Glu Asp Ile Ala Glu Val Leu
        210                 215                 220

Gln Lys Leu Asn
```

<210> SEQ ID NO 101
<211> LENGTH: 261
<212> TYPE: PRT
<213> ORGANISM: Artificial
<220> FEATURE:
<223> OTHER INFORMATION: AR domain (two-domain)

<400> SEQUENCE: 101

Gly Ser Asp Leu Gly His Lys Leu Leu Glu Ala Ala Val Ala Gly Gln
1               5                   10                  15

Asp Asp Glu Val Arg Ile Leu Leu Ala Ala Gly Ala Asp Val Asn Ala
            20                  25                  30

Lys Asp Trp Tyr Gly Lys Thr Pro Leu His Phe Ala Ala Gly Leu Gly
        35                  40                  45

His Leu Glu Ile Val Glu Val Leu Leu Lys Ala Gly Ala Asp Val Asn
    50                  55                  60

Ala Lys Asp Glu Asp Gly Gln Thr Pro Leu His Leu Ala Ala Ala Tyr
65                  70                  75                  80

Gly His Leu Glu Ile Val Glu Val Leu Leu Lys Ala Gly Ala Asp Val
                85                  90                  95

Asn Ala Gln Asp Asn Asp Gly Phe Thr Pro Ala Asp Leu Ala Ala Asp
            100                 105                 110

Ser Gly His Glu Asp Ile Ala Glu Val Leu Gln Lys Leu Gly Gly Gly
        115                 120                 125

Gly Ser Gly Gly Gly Ser Arg Ser Asp Leu Gly Lys Lys Leu Leu
130                 135                 140

Glu Ala Ala Arg Ala Gly Gln Asp Asp Glu Val Arg Ile Leu Met Ala
145                 150                 155                 160

Asn Gly Ala Asp Val Asn Ala Lys Asp Glu Tyr Gly Leu Thr Pro Leu
                165                 170                 175

Tyr Leu Ala Thr Ala His Gly His Leu Glu Ile Val Glu Val Leu Leu
            180                 185                 190

Lys Asn Gly Ala Asp Val Asn Ala Val Asp Ala Ile Gly Phe Thr Pro
        195                 200                 205

Leu His Leu Ala Ala Phe Ile Gly His Leu Glu Ile Ala Glu Val Leu
    210                 215                 220

Leu Lys His Gly Ala Asp Val Asn Ala Gln Asp Lys Phe Gly Lys Thr
225                 230                 235                 240

Ala Phe Asp Ile Ser Ile Gly Asn Gly Asn Glu Asp Leu Ala Glu Ile
                245                 250                 255

Leu Gln Lys Leu Asn
            260

<210> SEQ ID NO 102
<211> LENGTH: 269
<212> TYPE: PRT
<213> ORGANISM: Artificial
<220> FEATURE:
<223> OTHER INFORMATION: AR domain (two-domain)

<400> SEQUENCE: 102

Gly Ser Asp Leu Gly Ala Lys Leu Leu Ser Asp Leu Gly Val Lys Leu
1               5                   10                  15

Leu Trp Ala Ala Ala Arg Gly Gln Asp Asp Glu Val Arg Ile Leu Leu
            20                  25                  30

```
Ala Ala Gly Ala Asp Val Asn Ala Lys Asp Phe Gln Gly Ile Thr Pro
            35                  40                  45

Leu His Ile Ala Ala Gln Ser Gly His Leu Glu Ile Val Glu Val Leu
 50                  55                  60

Leu Lys Ala Gly Ala Asp Val Asn Ala Lys Asp Val Thr Gly Asp Thr
 65                  70                  75                  80

Pro Leu His Leu Ala Ala Gln His Gly His Leu Val Ile Val Glu Val
                85                  90                  95

Leu Leu Lys Ala Gly Ala Asp Val Asn Ala Gln Asp Glu Arg Gly Trp
            100                 105                 110

Thr Pro Ala Asp Leu Ala Ala Asp Trp Gly His Glu Asp Ile Ala Glu
            115                 120                 125

Val Leu Gln Lys Leu Gly Gly Gly Ser Gly Gly Gly Ser Arg
130                 135                 140

Ser Asp Leu Gly Lys Lys Leu Leu Glu Ala Ala Arg Ala Gly Gln Asp
145                 150                 155                 160

Asp Glu Val Arg Ile Leu Met Ala Asn Gly Ala Asp Val Asn Ala Lys
                165                 170                 175

Asp Glu Tyr Gly Leu Thr Pro Leu Tyr Leu Ala Thr Ala His Gly His
            180                 185                 190

Leu Glu Ile Val Glu Val Leu Leu Lys Asn Gly Ala Asp Val Asn Ala
            195                 200                 205

Val Asp Ala Ile Gly Phe Thr Pro Leu His Leu Ala Ala Phe Ile Gly
            210                 215                 220

His Leu Glu Ile Ala Glu Val Leu Leu Lys His Gly Ala Asp Val Asn
225                 230                 235                 240

Ala Gln Asp Lys Phe Gly Lys Thr Ala Phe Asp Ile Ser Ile Gly Asn
                245                 250                 255

Gly Asn Glu Asp Leu Ala Glu Ile Leu Gln Lys Leu Asn
            260                 265

<210> SEQ ID NO 103
<211> LENGTH: 302
<212> TYPE: PRT
<213> ORGANISM: Artificial
<220> FEATURE:
<223> OTHER INFORMATION: AR domain (two-domain)

<400> SEQUENCE: 103

Gly Ser Asp Leu Gly Ala Lys Leu Leu Ser Asp Leu Gly Val Lys Leu
 1               5                   10                  15

Leu Trp Ala Ala Ala Arg Gly Gln Asp Asp Glu Val Arg Ile Leu Leu
                20                  25                  30

Ala Ala Gly Ala Asp Val Asn Ala Lys Asp Phe Gln Gly Ile Thr Pro
            35                  40                  45

Leu His Ile Ala Ala Gln Ser Gly His Leu Glu Ile Val Glu Val Leu
 50                  55                  60

Leu Lys Ala Gly Ala Asp Val Asn Ala Lys Asp Val Thr Gly Asp Thr
 65                  70                  75                  80

Pro Leu His Leu Ala Ala Gln His Gly His Leu Val Ile Val Glu Val
                85                  90                  95

Leu Leu Lys Ala Gly Ala Asp Val Asn Ala Gln Asp Glu Arg Gly Trp
            100                 105                 110

Thr Pro Ala Asp Leu Ala Ala Asp Trp Gly His Glu Asp Ile Ala Glu
            115                 120                 125
```

Val Leu Gln Lys Leu Gly Gly Gly Ser Gly Gly Gly Ser Arg
        130                 135                 140

Ser Asp Leu Gly Lys Lys Leu Leu Glu Ala Ala Arg Ala Gly Gln Asp
145                 150                 155                 160

Asp Glu Val Arg Ile Leu Met Ala Asn Gly Ala Asp Val Asn Ala Thr
                165                 170                 175

Asp Ile His Gly His Thr Pro Leu His Leu Ala Ala Ala Met Gly His
                180                 185                 190

Leu Glu Ile Val Glu Val Leu Leu Lys Asn Gly Ala Asp Val Asn Ala
                195                 200                 205

Asn Asp Trp Arg Gly Phe Thr Pro Leu His Leu Ala Ala Leu Asn Gly
        210                 215                 220

His Leu Glu Ile Val Glu Val Leu Leu Lys Asn Gly Ala Asp Val Asn
225                 230                 235                 240

Ala Thr Asp Thr Ala Gly Asn Thr Pro Leu His Leu Ala Ala Trp Phe
                245                 250                 255

Gly His Leu Glu Ile Val Glu Val Leu Leu Lys Asn Gly Ala Asp Val
                260                 265                 270

Asn Ala Gln Asp Lys Phe Gly Lys Thr Ala Phe Asp Ile Ser Ile Asp
        275                 280                 285

Asn Gly Asn Glu Asp Leu Ala Glu Ile Leu Gln Lys Leu Asn
        290                 295                 300

<210> SEQ ID NO 104
<211> LENGTH: 270
<212> TYPE: PRT
<213> ORGANISM: Artificial
<220> FEATURE:
<223> OTHER INFORMATION: AR domain (two-domain)

<400> SEQUENCE: 104

Gly Ser Asp Leu Gly Asp Lys Leu Leu Gln Ser Asp Leu Gly Asn Lys
1               5                   10                  15

Leu Leu Ile Ala Ala Ser Val Gly Gln Asp Asp Glu Val Arg Ile Leu
                20                  25                  30

Leu Ala Ala Gly Ala Asp Val Asn Ala Lys Asp Glu Thr Gly Trp Thr
            35                  40                  45

Pro Leu His Leu Ala Ala Ala Trp Gly His Leu Glu Ile Val Glu Val
        50                  55                  60

Leu Leu Lys Ala Gly Ala Asp Val Asn Ala Lys Asp Val Lys Gly Gln
65                  70                  75                  80

Thr Pro Leu His Leu Ala Ala Ala Tyr Gly His Leu Glu Ile Val Glu
                85                  90                  95

Val Leu Leu Lys Ala Gly Ala Asp Val Asn Ala Gln Asp Asn Asp Gly
                100                 105                 110

Tyr Thr Pro Ala Asp Leu Ala Ala Arg Tyr Gly His Glu Asp Ile Ala
            115                 120                 125

Glu Val Leu Gln Lys Leu Gly Gly Gly Ser Gly Gly Gly Gly Ser
                130                 135                 140

Arg Ser Asp Leu Gly Lys Lys Leu Leu Glu Ala Ala Arg Ala Gly Gln
145                 150                 155                 160

Asp Asp Glu Val Arg Ile Leu Met Ala Asn Gly Ala Asp Val Asn Ala
                165                 170                 175

Lys Asp Glu Tyr Gly Leu Thr Pro Leu Tyr Leu Ala Thr Ala His Gly
                180                 185                 190

His Leu Glu Ile Val Glu Val Leu Lys Asn Gly Ala Asp Val Asn
            195                 200                 205

Ala Val Asp Ala Ile Gly Phe Thr Pro Leu His Leu Ala Ala Phe Ile
            210                 215                 220

Gly His Leu Glu Ile Ala Glu Val Leu Lys His Gly Ala Asp Val
225                 230                 235                 240

Asn Ala Gln Asp Lys Phe Gly Lys Thr Ala Phe Asp Ile Ser Ile Gly
            245                 250                 255

Asn Gly Asn Glu Asp Leu Ala Glu Ile Leu Gln Lys Leu Asn
            260                 265                 270

<210> SEQ ID NO 105
<211> LENGTH: 303
<212> TYPE: PRT
<213> ORGANISM: Artificial
<220> FEATURE:
<223> OTHER INFORMATION: AR domain (two-domain)

<400> SEQUENCE: 105

Gly Ser Asp Leu Gly Asp Lys Leu Leu Gln Ser Asp Leu Gly Asn Lys
1               5                   10                  15

Leu Leu Ile Ala Ala Ser Val Gly Gln Asp Asp Glu Val Arg Ile Leu
            20                  25                  30

Leu Ala Ala Gly Ala Asp Val Asn Ala Lys Asp Glu Thr Gly Trp Thr
            35                  40                  45

Pro Leu His Leu Ala Ala Ala Trp Gly His Leu Glu Ile Val Glu Val
            50                  55                  60

Leu Leu Lys Ala Gly Ala Asp Val Asn Ala Lys Asp Val Lys Gly Gln
65                  70                  75                  80

Thr Pro Leu His Leu Ala Ala Ala Tyr Gly His Leu Glu Ile Val Glu
            85                  90                  95

Val Leu Leu Lys Ala Gly Ala Asp Val Asn Ala Gln Asp Asn Asp Gly
            100                 105                 110

Tyr Thr Pro Ala Asp Leu Ala Ala Arg Tyr Gly His Glu Asp Ile Ala
            115                 120                 125

Glu Val Leu Gln Lys Leu Gly Gly Gly Ser Gly Gly Gly Ser
            130                 135                 140

Arg Ser Asp Leu Gly Lys Lys Leu Leu Glu Ala Ala Arg Ala Gly Gln
145                 150                 155                 160

Asp Asp Glu Val Arg Ile Leu Met Ala Asn Gly Ala Asp Val Asn Ala
            165                 170                 175

Thr Asp Ile His Gly His Thr Pro Leu His Leu Ala Ala Met Gly
            180                 185                 190

His Leu Glu Ile Val Glu Val Leu Lys Asn Gly Ala Asp Val Asn
            195                 200                 205

Ala Asn Asp Trp Arg Gly Phe Thr Pro Leu His Leu Ala Ala Leu Asn
            210                 215                 220

Gly His Leu Glu Ile Val Glu Val Leu Lys Asn Gly Ala Asp Val
225                 230                 235                 240

Asn Ala Thr Asp Thr Ala Gly Asn Thr Pro Leu His Leu Ala Ala Trp
            245                 250                 255

Phe Gly His Leu Glu Ile Val Glu Val Leu Lys Asn Gly Ala Asp
            260                 265                 270

Val Asn Ala Gln Asp Lys Phe Gly Lys Thr Ala Phe Asp Ile Ser Ile
            275                 280                 285

Asp Asn Gly Asn Glu Asp Leu Ala Glu Ile Leu Gln Lys Leu Asn
    290             295                 300

<210> SEQ ID NO 106
<211> LENGTH: 294
<212> TYPE: PRT
<213> ORGANISM: Artificial
<220> FEATURE:
<223> OTHER INFORMATION: AR domain (two-domain)

<400> SEQUENCE: 106

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Phe Tyr Gly Ile Thr Pro Leu His Leu Ala Ala Tyr Gly
        35                  40                  45

His Leu Glu Ile Val Glu Val Leu Leu Lys His Gly Ala Asp Val Asn
    50                  55                  60

Ala His Asp Trp Asn Gly Trp Thr Pro Leu His Leu Ala Ala Lys Tyr
65                  70                  75                  80

Gly His Leu Glu Ile Val Glu Val Leu Leu Lys His Gly Ala Asp Val
                85                  90                  95

Asn Ala Ile Asp Asn Ala Gly Lys Thr Pro Leu His Leu Ala Ala
            100                 105                 110

His Gly His Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
130                 135                 140

Asp Asn Gly Asn Glu Asp Leu Ala Glu Ile Leu Gln Lys Leu Gly Gly
145                 150                 155                 160

Gly Gly Ser Gly Gly Gly Gly Ser Arg Ser Asp Leu Gly Lys Lys Leu
                165                 170                 175

Leu Glu Ala Ala Arg Ala Gly Gln Asp Asp Glu Val Arg Ile Leu Met
            180                 185                 190

Ala Asn Gly Ala Asp Val Asn Ala Lys Asp Glu Tyr Gly Leu Thr Pro
        195                 200                 205

Leu Tyr Leu Ala Thr Ala His Gly His Leu Glu Ile Val Glu Val Leu
    210                 215                 220

Leu Lys Asn Gly Ala Asp Val Asn Ala Val Asp Ala Ile Gly Phe Thr
225                 230                 235                 240

Pro Leu His Leu Ala Ala Phe Ile Gly His Leu Glu Ile Ala Glu Val
                245                 250                 255

Leu Leu Lys His Gly Ala Asp Val Asn Ala Gln Asp Lys Phe Gly Lys
            260                 265                 270

Thr Ala Phe Asp Ile Ser Ile Gly Asn Gly Asn Glu Asp Leu Ala Glu
        275                 280                 285

Ile Leu Gln Lys Leu Asn
    290

<210> SEQ ID NO 107
<211> LENGTH: 327
<212> TYPE: PRT
<213> ORGANISM: Artificial
<220> FEATURE:
<223> OTHER INFORMATION: AR domain (two-domain)

<400> SEQUENCE: 107

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Lys Asp Phe Tyr Gly Ile Thr Pro Leu His Leu Ala Ala Ala Tyr Gly
            35                  40                  45

His Leu Glu Ile Val Glu Val Leu Leu Lys His Gly Ala Asp Val Asn
50                      55                  60

Ala His Asp Trp Asn Gly Trp Thr Pro Leu His Leu Ala Ala Lys Tyr
65                  70                  75                  80

Gly His Leu Glu Ile Val Glu Val Leu Leu Lys His Gly Ala Asp Val
                85                  90                  95

Asn Ala Ile Asp Asn Ala Gly Lys Thr Pro Leu His Leu Ala Ala Ala
                100                 105                 110

His Gly His Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
130                 135                 140

Asp Asn Gly Asn Glu Asp Leu Ala Glu Ile Leu Gln Lys Leu Gly Gly
145                 150                 155                 160

Gly Gly Ser Gly Gly Gly Ser Arg Ser Asp Leu Gly Lys Lys Leu
                165                 170                 175

Leu Glu Ala Ala Arg Ala Gly Gln Asp Asp Glu Val Arg Ile Leu Met
            180                 185                 190

Ala Asn Gly Ala Asp Val Asn Ala Thr Asp Ile His Gly His Thr Pro
            195                 200                 205

Leu His Leu Ala Ala Ala Met Gly His Leu Glu Ile Val Glu Val Leu
        210                 215                 220

Leu Lys Asn Gly Ala Asp Val Asn Ala Asn Asp Trp Arg Gly Phe Thr
225                 230                 235                 240

Pro Leu His Leu Ala Ala Leu Asn Gly His Leu Glu Ile Val Glu Val
            245                 250                 255

Leu Leu Lys Asn Gly Ala Asp Val Asn Ala Thr Asp Thr Ala Gly Asn
            260                 265                 270

Thr Pro Leu His Leu Ala Ala Trp Phe Gly His Leu Glu Ile Val Glu
            275                 280                 285

Val Leu Leu Lys Asn Gly Ala Asp Val Asn Ala Gln Asp Lys Phe Gly
            290                 295                 300

Lys Thr Ala Phe Asp Ile Ser Ile Asp Asn Gly Asn Glu Asp Leu Ala
305                 310                 315                 320

Glu Ile Leu Gln Lys Leu Asn
                325

<210> SEQ ID NO 108
<211> LENGTH: 270
<212> TYPE: PRT
<213> ORGANISM: Artificial
<220> FEATURE:
<223> OTHER INFORMATION: AR domain (two-domain)

<400> SEQUENCE: 108

Gly Ser Asp Leu Gly Asp Lys Leu Leu Gln Ser Asp Leu Gly Ile Lys
1               5                   10                  15

Leu Leu Phe Ala Ala Ala Lys Ser Gln Asp Asp Glu Val Arg Ile Leu
                20                  25                  30
```

Leu Ala Ala Gly Ala Asp Val Asn Ala Lys Asp Phe Gln Ser Val Thr
                35                  40                  45

Pro Leu His Ile Ala Ala Gln Ser Gly His Leu Glu Ile Val Glu Val
    50                  55                  60

Leu Leu Lys Ala Gly Ala Asp Val Asn Ala Lys Asp Val Thr Gly Asp
65                  70                  75                  80

Thr Pro Leu His Leu Ala Ala Gln His Gly His Leu Glu Ile Val Glu
                85                  90                  95

Val Leu Leu Lys Ala Gly Ala Asp Val Asn Ala Gln Asp Glu Arg Gly
                100                 105                 110

Trp Thr Pro Ala Asp Leu Ala Ala Asp Trp Gly His Glu Asp Ile Ala
            115                 120                 125

Glu Val Leu Gln Lys Leu Gly Gly Gly Ser Gly Gly Gly Gly Ser
130                 135                 140

Arg Ser Asp Leu Gly Ile Lys Leu Leu Val Ala Ala Ala Gln Gly Gln
145                 150                 155                 160

Asp Asp Glu Val Arg Ile Leu Leu Ala Ala Gly Ala Asp Val Asn Ala
                165                 170                 175

Lys Asp Gln Gln Gly Ala Thr Pro Leu His Leu Ala Ala Trp Lys Gly
                180                 185                 190

His Leu Glu Ile Val Glu Val Leu Leu Lys Ala Gly Ala Asp Val Asn
                195                 200                 205

Ala Lys Asp Leu Ser Gly Asp Thr Pro Leu His Ile Ala Ala Trp Phe
                210                 215                 220

Gly His Leu Glu Ile Val Glu Val Leu Leu Lys Ala Gly Ala Asp Val
225                 230                 235                 240

Asn Ala Gln Asp Thr Glu Gly Tyr Thr Pro Ala Asp Leu Ala Ala Leu
                245                 250                 255

Tyr Gly His Glu Asp Ile Ala Glu Val Leu Gln Lys Leu Asn
                260                 265                 270

<210> SEQ ID NO 109
<211> LENGTH: 294
<212> TYPE: PRT
<213> ORGANISM: Artificial
<220> FEATURE:
<223> OTHER INFORMATION: AR domain (two-domain)

<400> SEQUENCE: 109

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Lys Asp Glu Tyr Gly Leu Thr Pro Leu Tyr Leu Ala Thr Ala His Gly
                35                  40                  45

His Leu Glu Ile Val Glu Val Leu Leu Lys Asn Gly Ala Asp Val Asn
                50                  55                  60

Ala Val Asp Ala Ile Gly Phe Thr Pro Leu His Leu Ala Ala Phe Ile
65                  70                  75                  80

Gly His Leu Glu Ile Ala Glu Val Leu Leu Lys His Gly Ala Asp Val
                85                  90                  95

Asn Ala Gln Asp Lys Phe Gly Lys Thr Ala Phe Asp Ile Ser Ile Gly
                100                 105                 110

Asn Gly Asn Glu Asp Leu Ala Glu Ile Leu Gln Lys Leu Gly Gly Gly
                115                 120                 125

```
Gly Ser Gly Gly Gly Ser Arg Ser Asp Leu Gly Lys Lys Leu Leu
            130                 135                 140
Glu Ala Ala Arg Ala Gly Gln Asp Asp Glu Val Arg Ile Leu Met Ala
145                 150                 155                 160
Asn Gly Ala Asp Val Asn Ala Lys Asp Phe Tyr Gly Ile Thr Pro Leu
                165                 170                 175
His Leu Ala Ala Ala Tyr Gly His Leu Glu Ile Val Glu Val Leu Leu
            180                 185                 190
Lys His Gly Ala Asp Val Asn Ala His Asp Trp Asn Gly Trp Thr Pro
        195                 200                 205
Leu His Leu Ala Ala Lys Tyr Gly His Leu Glu Ile Val Glu Val Leu
        210                 215                 220
Leu Lys His Gly Ala Asp Val Asn Ala Ile Asp Asn Ala Gly Lys Thr
225                 230                 235                 240
Pro Leu His Leu Ala Ala His Gly His Leu Glu Ile Val Glu Val
            245                 250                 255
Leu Leu Lys Tyr Gly Ala Asp Val Asn Ala Gln Asp Lys Phe Gly Lys
            260                 265                 270
Thr Ala Phe Asp Ile Ser Ile Asp Asn Gly Asn Glu Asp Leu Ala Glu
            275                 280                 285
Ile Leu Gln Lys Leu Asn
            290

<210> SEQ ID NO 110
<211> LENGTH: 269
<212> TYPE: PRT
<213> ORGANISM: Artificial
<220> FEATURE:
<223> OTHER INFORMATION: AR domain (two-domain)

<400> SEQUENCE: 110

Gly Ser Asp Leu Gly Lys Lys Leu Leu Glu Ala Ala Arg Ala Gly Gln
1               5                   10                  15
Asp Asp Glu Val Arg Ile Leu Met Ala Asn Gly Ala Asp Val Asn Ala
            20                  25                  30
Lys Asp Glu Tyr Gly Leu Thr Pro Leu Tyr Leu Ala Thr Ala His Gly
        35                  40                  45
His Leu Glu Ile Val Glu Val Leu Leu Lys Asn Gly Ala Asp Val Asn
    50                  55                  60
Ala Val Asp Ala Ile Gly Phe Thr Pro Leu His Leu Ala Ala Phe Ile
65                  70                  75                  80
Gly His Leu Glu Ile Ala Glu Val Leu Leu Lys His Gly Ala Asp Val
            85                  90                  95
Asn Ala Gln Asp Lys Phe Gly Lys Thr Ala Phe Asp Ile Ser Ile Gly
            100                 105                 110
Asn Gly Asn Glu Asp Leu Ala Glu Ile Leu Gln Lys Leu Gly Gly Gly
            115                 120                 125
Gly Ser Gly Gly Gly Gly Ser Arg Ser Asp Leu Gly Ala Lys Leu Leu
            130                 135                 140
Ser Asp Leu Gly Val Lys Leu Leu Trp Ala Ala Arg Ala Gly Gln Asp
145                 150                 155                 160
Asp Glu Val Arg Ile Leu Leu Ala Ala Gly Ala Asp Val Asn Ala Lys
                165                 170                 175
Asp Phe Gln Gly Ile Thr Pro Leu His Ile Ala Ala Gln Ser Gly His
            180                 185                 190
```

Leu Glu Ile Val Glu Val Leu Leu Lys Ala Gly Ala Asp Val Asn Ala
        195                 200                 205

Lys Asp Val Thr Gly Asp Thr Pro Leu His Leu Ala Ala Gln His Gly
        210                 215                 220

His Leu Val Ile Val Glu Val Leu Leu Lys Ala Gly Ala Asp Val Asn
225                 230                 235                 240

Ala Gln Asp Glu Arg Gly Trp Thr Pro Ala Asp Leu Ala Ala Asp Trp
                245                 250                 255

Gly His Glu Asp Ile Ala Glu Val Leu Gln Lys Leu Asn
                260                 265

<210> SEQ ID NO 111
<211> LENGTH: 126
<212> TYPE: PRT
<213> ORGANISM: Artificial
<220> FEATURE:
<223> OTHER INFORMATION: AR domain (one-domain) Negative Control

<400> SEQUENCE: 111

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Lys Asp Lys Asp Gly Tyr Thr Pro Leu His Leu Ala Ala Arg Glu Gly
            35                  40                  45

His Leu Glu Ile Val Glu Val Leu Leu Lys Ala Gly Ala Asp Val Asn
        50                  55                  60

Ala Lys Asp Lys Asp Gly Tyr Thr Pro Leu His Leu Ala Ala Arg Glu
65                  70                  75                  80

Gly His Leu Glu Ile Val Glu Val Leu Leu Lys Ala Gly Ala Asp Val
                85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Leu Asn
            115                 120                 125

<210> SEQ ID NO 112
<211> LENGTH: 126
<212> TYPE: PRT
<213> ORGANISM: Artificial Sequence
<220> FEATURE:
<223> OTHER INFORMATION: AR domain (one-domain)

<400> SEQUENCE: 112

Gly Ser Asp Leu Gly Asn Lys Leu Leu Ile Ala Ala Ser Val Gly Gln
1               5                   10                  15

Asp Asp Glu Val Arg Ile Leu Leu Ala Ala Gly Ala Asp Val Asn Ala
                20                  25                  30

Lys Asp Glu Thr Gly Trp Thr Pro Leu His Leu Ala Ala Ala Trp Gly
            35                  40                  45

His Leu Glu Ile Val Glu Val Leu Leu Lys Ala Gly Ala Asp Val Asn
        50                  55                  60

Ala Lys Asp Val Lys Gly Gln Thr Pro Leu His Leu Ala Ala Ala Tyr
65                  70                  75                  80

Gly His Leu Glu Ile Val Glu Val Leu Leu Lys Ala Gly Ala Asp Val
                85                  90                  95

Asn Ala Gln Asp Asn Asp Gly Tyr Thr Pro Ala Asp Leu Ala Ala Arg

```
                100             105             110
Tyr Gly His Glu Asp Ile Ala Glu Val Leu Gln Lys Leu Asn
        115                 120             125

<210> SEQ ID NO 113
<211> LENGTH: 126
<212> TYPE: PRT
<213> ORGANISM: Artificial Sequence
<220> FEATURE:
<223> OTHER INFORMATION: AR domain (one-domain)

<400> SEQUENCE: 113

Gly Ser Asp Leu Gly Val Lys Leu Leu Trp Ala Ala His Gly Gln
1               5                   10                  15

Asp Asp Glu Val Arg Ile Leu Leu Ala Ala Asp Ala Asp Val Asn Ala
            20                  25                  30

Lys Asp Trp Tyr Gly Thr Thr Pro Leu His Ile Ala Ala Val Ala Gly
        35                  40                  45

His Leu Glu Ile Val Glu Val Leu Leu Lys Ala Gly Ala Asp Val Asn
    50                  55                  60

Ala Lys Asp Asp Phe Gly Thr Thr Pro Leu His Ala Ala Ala Asp Tyr
65                  70                  75                  80

Gly His Leu Glu Ile Val Glu Val Leu Leu Lys Ala Gly Ala Asp Val
                85                  90                  95

Asn Ala Gln Asp Tyr Thr Gly His Thr Pro Ala Asp Leu Ala Ala Val
            100                 105                 110

Tyr Gly His Glu Asp Ile Ala Ala Val Leu Gln Lys Leu Asn
        115                 120             125

<210> SEQ ID NO 114
<211> LENGTH: 126
<212> TYPE: PRT
<213> ORGANISM: Artificial Sequence
<220> FEATURE:
<223> OTHER INFORMATION: AR domain (one-domain)

<400> SEQUENCE: 114

Gly Ser Asp Leu Gly Ala Lys Leu Leu Trp Ala Ala Lys Gly Gln
1               5                   10                  15

Asp Asp Glu Val Arg Ile Leu Leu Ala Ala Gly Ala Asp Val Asn Ala
            20                  25                  30

Lys Asp Trp Glu Gly Val Thr Pro Leu His Ile Ala Ala His Ala Gly
        35                  40                  45

His Leu Glu Ile Val Glu Val Leu Leu Lys Ala Gly Ala Asp Val Asn
    50                  55                  60

Ala Lys Asp Ile Ile Gly Trp Thr Pro Leu His Ser Ala Ala Val Tyr
65                  70                  75                  80

Gly His Leu Glu Ile Val Glu Val Leu Leu Lys Ala Gly Ala Asp Val
                85                  90                  95

Asn Ala Gln Asp Trp Tyr Gly Thr Thr Pro Ala Asp Leu Ala Ala Trp
            100                 105                 110

Trp Gly His Glu Asp Ile Ala Val Val Leu Gln Lys Leu Asn
        115                 120             125

<210> SEQ ID NO 115
<211> LENGTH: 126
<212> TYPE: PRT
<213> ORGANISM: Artificial Sequence
<220> FEATURE:
```

<223> OTHER INFORMATION: AR domain (one-domain)

<400> SEQUENCE: 115

Gly Ser Asp Leu Gly Ile Lys Leu Leu Phe Ala Ala Lys Gly Gln
1               5                   10                  15

Asp Asp Glu Val Arg Glu Leu Lys Ala Gly Ala Asp Val Asn Ala
            20                  25                  30

Lys Asp Phe Gln Gly Val Thr Pro Leu His Ile Ala Ala Gln Ser Gly
        35                  40                  45

His Leu Glu Ile Val Glu Val Leu Leu Lys Ala Gly Ala Asp Val Asn
    50                  55                  60

Ala Lys Asp Val Thr Gly Asp Thr Pro Leu His Leu Ala Ala Gln His
65                  70                  75                  80

Gly His Leu Glu Ile Val Glu Val Leu Leu Lys Ala Gly Ala Asp Val
                85                  90                  95

Asn Ala Gln Asp Glu Arg Gly Trp Thr Pro Ala Asp Leu Ala Ala Asp
            100                 105                 110

Trp Gly His Glu Asp Ile Ala Glu Val Leu Gln Lys Leu Asn
        115                 120                 125

<210> SEQ ID NO 116
<211> LENGTH: 126
<212> TYPE: PRT
<213> ORGANISM: Artificial Sequence
<220> FEATURE:
<223> OTHER INFORMATION: AR doamin (one-domain)

<400> SEQUENCE: 116

Gly Ser Asp Leu Gly Ile Lys Leu Leu Ile Ala Ala Ser His Gly Gln
1               5                   10                  15

Asp Asp Glu Val Arg Ile Leu Leu Ala Ala Gly Ala Asn Val Asn Ala
            20                  25                  30

Lys Asp Phe Gln Gly Val Thr Pro Leu His Ile Ala Ala Gln Ser Gly
        35                  40                  45

His Leu Glu Ile Val Glu Val Leu Leu Lys Ala Gly Ala Asp Val Asn
    50                  55                  60

Ala Lys Asp Val Thr Gly Asp Thr Pro Leu His Leu Ala Ala Gln His
65                  70                  75                  80

Gly His Leu Glu Ile Val Glu Val Leu Leu Lys Ala Gly Ala Asp Val
                85                  90                  95

Asn Ala Gln Asp Glu Arg Gly Trp Thr Pro Ala Asp Leu Ala Ala Asp
            100                 105                 110

Trp Gly His Glu Asp Ile Ala Glu Val Leu Gln Lys Leu Asn
        115                 120                 125

<210> SEQ ID NO 117
<211> LENGTH: 126
<212> TYPE: PRT
<213> ORGANISM: Artificial Sequence
<220> FEATURE:
<223> OTHER INFORMATION: AR domain (one-domain)

<400> SEQUENCE: 117

Gly Ser Asp Leu Gly Gln Lys Leu Leu Ile Ala Ala Ser Arg Gly Gln
1               5                   10                  15

Asp Asp Glu Val Arg Ile Leu Leu Ala Ala Gly Ala Asp Val Asn Ala
            20                  25                  30

Lys Asp Phe Gln Gly Val Thr Pro Leu His Ile Ala Ala Gln Ser Gly

```
              35                  40                  45

His Leu Glu Ile Val Glu Val Leu Leu Lys Ala Gly Ala Asp Val Asn
 50                  55                  60

Ala Lys Asp Val Thr Gly Asp Thr Pro Leu His Leu Ala Ala Gln His
65                  70                  75                  80

Gly His Leu Glu Ile Val Glu Val Leu Leu Lys Ala Gly Ala Asp Val
                85                  90                  95

Asn Ala Gln Asp Glu Arg Gly Trp Thr Pro Thr Asp Leu Ala Ala Asp
                100                 105                 110

Trp Gly His Glu Asp Ile Ala Glu Val Leu Gln Lys Leu Asn
        115                 120                 125

<210> SEQ ID NO 118
<211> LENGTH: 126
<212> TYPE: PRT
<213> ORGANISM: Artificial Sequence
<220> FEATURE:
<223> OTHER INFORMATION: AR domain (one-domain)

<400> SEQUENCE: 118

Gly Ser Asp Leu Gly Ile Lys Leu Leu Trp Ala Ala Ala Gln Gly Gln
  1               5                  10                  15

Asp Asp Glu Val Arg Ile Leu Leu Ala Ala Gly Ala Asp Val Asn Ala
                20                  25                  30

Lys Asp Phe Gln Gly Val Thr Pro Leu His Ile Ala Ala Gln Ser Gly
                35                  40                  45

His Leu Glu Val Val Glu Val Leu Leu Lys Ala Gly Ala Asp Val Asn
 50                  55                  60

Ala Lys Asp Val Thr Gly Asp Thr Pro Leu His Leu Ala Ala Gln His
65                  70                  75                  80

Gly His Leu Glu Ile Val Glu Val Leu Leu Lys Ala Gly Ala Asp Val
                85                  90                  95

Asn Ala Gln Asp Glu Arg Gly Trp Thr Pro Ala Asp Leu Ala Ala Asp
                100                 105                 110

Trp Gly His Glu Asp Ile Ala Glu Val Leu Gln Lys Leu Asn
        115                 120                 125

<210> SEQ ID NO 119
<211> LENGTH: 126
<212> TYPE: PRT
<213> ORGANISM: Artificial Sequence
<220> FEATURE:
<223> OTHER INFORMATION: AR domain (one-domain)

<400> SEQUENCE: 119

Gly Ser Asp Leu Gly Phe Lys Leu Leu Phe Ala Ala Lys Ser Gln
  1               5                  10                  15

Asp Asp Glu Val Arg Ile Leu Leu Ala Ala Gly Ala Asp Val Asn Ala
                20                  25                  30

Lys Asp Phe Gln Gly Val Thr Ser Leu His Ile Ala Ala Gln Ser Gly
                35                  40                  45

His Leu Glu Ile Val Glu Val Leu Leu Lys Ala Gly Ala Asp Val Asn
 50                  55                  60

Ala Lys Asp Val Thr Gly Asp Thr Pro Leu His Leu Ala Ala Gln His
65                  70                  75                  80

Gly His Leu Glu Ile Val Glu Val Leu Leu Lys Ala Gly Ala Asp Val
                85                  90                  95
```

Asn Ala Gln Asp Glu Arg Gly Trp Thr Pro Ala Asp Leu Ala Ala Asp
                100                 105                 110

Trp Gly His Glu Asp Ile Ala Glu Val Leu Gln Lys Leu Asn
            115                 120                 125

<210> SEQ ID NO 120
<211> LENGTH: 126
<212> TYPE: PRT
<213> ORGANISM: Artificial Sequence
<220> FEATURE:
<223> OTHER INFORMATION: AR domain (one-domain)

<400> SEQUENCE: 120

Gly Ser Asp Leu Gly Val Lys Leu Leu Trp Ala Ala Ala Arg Gly Gln
1               5                   10                  15

Asp Asp Glu Val Arg Glu Leu Leu Lys Ala Gly Ala Asp Val Asn Ala
            20                  25                  30

Lys Asp Phe Gln Gly Ile Thr Pro Leu His Ile Ala Ala Thr Asn Gly
        35                  40                  45

His Leu Glu Ile Val Glu Val Leu Leu Lys Ala Gly Ala Asp Val Asn
    50                  55                  60

Ala Lys Asp Ile Thr Gly Glu Thr Pro Leu His His Ala Ala Asp Ser
65                  70                  75                  80

Gly His Leu Glu Ile Val Glu Val Leu Leu Lys Ala Gly Ala Asp Val
                85                  90                  95

Asn Ala Gln Asp Lys Ala Gly Val Thr Pro Ala Asp Leu Ala Ala Ala
            100                 105                 110

Trp Gly His Glu Asp Ile Ala Glu Val Leu Gln Lys Leu Asn
        115                 120                 125

<210> SEQ ID NO 121
<211> LENGTH: 126
<212> TYPE: PRT
<213> ORGANISM: Artificial Sequence
<220> FEATURE:
<223> OTHER INFORMATION: AR domain (one-domain)

<400> SEQUENCE: 121

Gly Ser Asp Leu Gly Val Lys Leu Leu Trp Ala Ala Ala Arg Gly Gln
1               5                   10                  15

Asp Asp Glu Val Arg Glu Leu Leu Lys Ala Gly Ala Asp Val Asn Ala
            20                  25                  30

Lys Asp Phe Gln Gly Ile Thr Pro Leu His Ile Ala Ala Gln Ser Gly
        35                  40                  45

His Leu Glu Ile Val Glu Val Leu Leu Lys Ala Gly Ala Asp Val Asn
    50                  55                  60

Ala Lys Asp Val Thr Gly Asp Thr Pro Leu His Leu Ala Ala Gln His
65                  70                  75                  80

Gly His Leu Glu Ile Val Glu Val Leu Leu Lys Ala Gly Ala Asp Val
                85                  90                  95

Asn Ala Gln Asp Glu Arg Gly Trp Thr Pro Ala Asp Leu Ala Ala Asp
            100                 105                 110

Trp Gly His Glu Asp Ile Ala Glu Val Leu Gln Lys Leu Asn
        115                 120                 125

<210> SEQ ID NO 122
<211> LENGTH: 274
<212> TYPE: PRT
<213> ORGANISM: Artificial Sequence
<220> FEATURE:
<223> OTHER INFORMATION: AR domain (two-domain)

<400> SEQUENCE: 122

Gly Ser Asp Leu Gly Val Lys Leu Leu Trp Ala Ala Ala Arg Gly Gln
1               5                   10                  15

Asp Asp Glu Val Arg Glu Leu Leu Lys Ala Gly Ala Asp Val Asn Ala
            20                  25                  30

Lys Asp Phe Gln Gly Ile Thr Pro Leu His Ile Ala Ala Gln Ser Gly
        35                  40                  45

His Leu Glu Ile Val Glu Val Leu Leu Lys Ala Gly Ala Asp Val Asn
    50                  55                  60

Ala Lys Asp Val Thr Gly Asp Thr Pro Leu His Leu Ala Ala Gln His
65              70                  75                  80

Gly His Leu Glu Ile Val Glu Val Leu Leu Lys Ala Gly Ala Asp Val
            85                  90                  95

Asn Ala Gln Asp Glu Arg Gly Trp Thr Pro Ala Asp Leu Ala Ala Asp
        100                 105                 110

Trp Gly His Glu Asp Ile Ala Glu Val Leu Gln Lys Ala Ala Gly Ser
    115                 120                 125

Pro Thr Pro Thr Pro Thr Thr Pro Thr Pro Thr Pro Thr Thr Pro Thr
130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
            165                 170                 175

Asp Val Asn Ala Lys Asp Glu Tyr Gly Leu Thr Pro Leu Tyr Leu Ala
        180                 185                 190

Thr Ala His Gly His His Leu Glu Ile Val Glu Val Leu Leu Lys Ala Gly
    195                 200                 205

Ala Asp Val Asn Ala Val Asp Ala Ile Gly Phe Thr Pro Leu His Leu
210                 215                 220

Ala Ala Phe Ile Gly His Leu Glu Ile Ala Glu Val Leu Leu Lys Ala
225                 230                 235                 240

Gly Ala Asp Val Asn Ala Gln Asp Lys Phe Gly Lys Thr Pro Ala Asp
            245                 250                 255

Ile Ala Ala Gly Ala Gly Asn Glu Asp Ile Ala Glu Val Leu Gln Lys
        260                 265                 270

Ala Ala

<210> SEQ ID NO 123
<211> LENGTH: 274
<212> TYPE: PRT
<213> ORGANISM: Artificial Sequence
<220> FEATURE:
<223> OTHER INFORMATION: AR domain (two-domain)

<400> SEQUENCE: 123

Gly Ser Asp Leu Gly Val Lys Leu Leu Trp Ala Ala Ala Arg Gly Gln
1               5                   10                  15

Asp Asp Glu Val Arg Glu Leu Leu Lys Ala Gly Ala Asp Val Asn Ala
            20                  25                  30

Lys Asp Phe Gln Gly Ile Thr Pro Leu His Ile Ala Ala Gln Ser Gly
        35                  40                  45

His Leu Glu Ile Val Glu Val Leu Leu Lys Ala Gly Ala Asp Val Asn
    50                  55                  60

```
Ala Lys Asp Val Thr Gly Asp Thr Pro Leu His Leu Ala Ala Gln His
 65                  70                  75                  80

Gly His Leu Glu Ile Val Glu Val Leu Leu Lys Ala Gly Ala Asp Val
                 85                  90                  95

Asn Ala Gln Asp Glu Arg Gly Lys Thr Pro Ala Asp Leu Ala Ala Asp
            100                 105                 110

Trp Gly His Glu Asp Ile Ala Glu Val Leu Gln Lys Ala Ala Gly Ser
        115                 120                 125

Pro Thr Pro Thr Pro Thr Pro Thr Pro Thr Pro Thr Pro Thr Pro Thr
130                 135                 140

Pro Thr Pro Thr Gly Ser Asp Leu Gly Lys Lys Leu Leu Glu Ala Ala
145                 150                 155                 160

Arg Ala Gly Gln Asp Asp Glu Val Arg Glu Leu Leu Lys Ala Gly Ala
                165                 170                 175

Asp Val Asn Ala Lys Asp Glu Tyr Gly Leu Thr Pro Leu Tyr Leu Ala
            180                 185                 190

Thr Ala His Gly His Leu Glu Ile Val Glu Val Leu Leu Lys Ala Gly
        195                 200                 205

Ala Asp Val Asn Ala Val Asp Ala Ile Gly Phe Thr Pro Leu His Leu
    210                 215                 220

Ala Ala Phe Ile Gly His Leu Glu Ile Ala Glu Val Leu Leu Lys Ala
225                 230                 235                 240

Gly Ala Asp Val Asn Ala Gln Asp Lys Phe Gly Lys Thr Pro Ala Asp
                245                 250                 255

Ile Ala Ala Gly Ala Gly Asn Glu Asp Ile Ala Glu Val Leu Gln Lys
            260                 265                 270

Ala Ala

<210> SEQ ID NO 124
<211> LENGTH: 32
<212> TYPE: PRT
<213> ORGANISM: Artificial Sequence
<220> FEATURE:
<223> OTHER INFORMATION: N-Cap module (Nr)

<400> SEQUENCE: 124

Gly Ser Asp Leu Gly Ile Lys Leu Leu Phe Ala Ala Ala Lys Gly Gln
 1               5                  10                  15

Asp Asp Glu Val Arg Glu Leu Leu Lys Ala Gly Ala Asp Val Asn Ala
            20                  25                  30

<210> SEQ ID NO 125
<211> LENGTH: 33
<212> TYPE: PRT
<213> ORGANISM: Artificial Sequence
<220> FEATURE:
<223> OTHER INFORMATION: AR module (M1.1b)

<400> SEQUENCE: 125

Lys Asp Phe Gln Gly Val Thr Pro Leu His Ile Ala Ala Gln Ser Gly
 1               5                  10                  15

His Leu Glu Ile Val Glu Val Leu Leu Lys Ala Gly Ala Asp Val Asn
            20                  25                  30

Ala

<210> SEQ ID NO 126
<211> LENGTH: 33
```

```
<212> TYPE: PRT
<213> ORGANISM: Artificial Sequence
<220> FEATURE:
<223> OTHER INFORMATION: AR module (M1.1b)

<400> SEQUENCE: 126

Lys Asp Val Thr Gly Asp Thr Pro Leu His Leu Ala Ala Gln His Gly
1               5                   10                  15

His Leu Glu Ile Val Glu Val Leu Leu Lys Ala Gly Ala Asp Val Asn
            20                  25                  30

Ala

<210> SEQ ID NO 127
<211> LENGTH: 28
<212> TYPE: PRT
<213> ORGANISM: Artificial Sequence
<220> FEATURE:
<223> OTHER INFORMATION: C-Cap module (Cr)

<400> SEQUENCE: 127

Gln Asp Glu Arg Gly Trp Thr Pro Ala Asp Leu Ala Ala Asp Trp Gly
1               5                   10                  15

His Glu Asp Ile Ala Glu Val Leu Gln Lys Leu Asn
            20                  25

<210> SEQ ID NO 128
<211> LENGTH: 32
<212> TYPE: PRT
<213> ORGANISM: Artificial Sequence
<220> FEATURE:
<223> OTHER INFORMATION: N-Cap module (Nr)

<400> SEQUENCE: 128

Gly Ser Asp Leu Gly Val Lys Leu Leu Trp Ala Ala Arg Gly Gln
1               5                   10                  15

Asp Asp Glu Val Arg Glu Leu Leu Lys Ala Gly Ala Asp Val Asn Ala
            20                  25                  30

<210> SEQ ID NO 129
<211> LENGTH: 33
<212> TYPE: PRT
<213> ORGANISM: Artificial Sequence
<220> FEATURE:
<223> OTHER INFORMATION: AR module (M1.1b)

<400> SEQUENCE: 129

Lys Asp Phe Gln Gly Ile Thr Pro Leu His Ile Ala Ala Thr Asn Gly
1               5                   10                  15

His Leu Glu Ile Val Glu Val Leu Leu Lys Ala Gly Ala Asp Val Asn
            20                  25                  30

Ala

<210> SEQ ID NO 130
<211> LENGTH: 33
<212> TYPE: PRT
<213> ORGANISM: Artificial Sequence
<220> FEATURE:
<223> OTHER INFORMATION: AR module (M1.1b)

<400> SEQUENCE: 130

Lys Asp Ile Thr Gly Glu Thr Pro Leu His His Ala Ala Asp Ser Gly
1               5                   10                  15

His Leu Glu Ile Val Glu Val Leu Leu Lys Ala Gly Ala Asp Val Asn
```

```
                    20                  25                  30

Ala

<210> SEQ ID NO 131
<211> LENGTH: 28
<212> TYPE: PRT
<213> ORGANISM: Artificial Sequence
<220> FEATURE:
<223> OTHER INFORMATION: C-Cap module (Cr)

<400> SEQUENCE: 131

Gln Asp Lys Ala Gly Val Thr Pro Ala Asp Leu Ala Ala Ala Trp Gly
1               5                   10                  15

His Glu Asp Ile Ala Glu Val Leu Gln Lys Leu Asn
            20                  25

<210> SEQ ID NO 132
<211> LENGTH: 32
<212> TYPE: PRT
<213> ORGANISM: Artificial Sequence
<220> FEATURE:
<223> OTHER INFORMATION: N-Cap module (Nr)

<400> SEQUENCE: 132

Gly Ser Asp Leu Gly Val Lys Leu Leu Trp Ala Ala Ala Arg Gly Gln
1               5                   10                  15

Asp Asp Glu Val Arg Glu Leu Leu Lys Ala Gly Ala Asp Val Asn Ala
            20                  25                  30

<210> SEQ ID NO 133
<211> LENGTH: 33
<212> TYPE: PRT
<213> ORGANISM: Artificial Sequence
<220> FEATURE:
<223> OTHER INFORMATION: AR module (M1.1b)

<400> SEQUENCE: 133

Lys Asp Phe Gln Gly Ile Thr Pro Leu His Ile Ala Ala Gln Ser Gly
1               5                   10                  15

His Leu Glu Ile Val Glu Val Leu Leu Lys Ala Gly Ala Asp Val Asn
            20                  25                  30

Ala

<210> SEQ ID NO 134
<211> LENGTH: 33
<212> TYPE: PRT
<213> ORGANISM: Artificial Sequence
<220> FEATURE:
<223> OTHER INFORMATION: AR module (M1.1b)

<400> SEQUENCE: 134

Lys Asp Val Thr Gly Asp Thr Pro Leu His Leu Ala Ala Gln His Gly
1               5                   10                  15

His Leu Glu Ile Val Glu Val Leu Leu Lys Ala Gly Ala Asp Val Asn
            20                  25                  30

Ala

<210> SEQ ID NO 135
<211> LENGTH: 28
<212> TYPE: PRT
<213> ORGANISM: Artificial Sequence
<220> FEATURE:
<223> OTHER INFORMATION: C-Cap module (Cr)
```

<400> SEQUENCE: 135

Gln Asp Glu Arg Gly Trp Thr Pro Ala Asp Leu Ala Ala Asp Trp Gly
1               5                   10                  15

His Glu Asp Ile Ala Glu Val Leu Gln Lys Leu Asn
            20                  25

<210> SEQ ID NO 136
<211> LENGTH: 278
<212> TYPE: PRT
<213> ORGANISM: Artificial Sequence
<220> FEATURE:
<223> OTHER INFORMATION: AR domain (two-domain)

<400> SEQUENCE: 136

Gly Ser Asp Leu Gly Ala Lys Leu Leu Ser Asp Leu Gly Val Lys Leu
1               5                   10                  15

Leu Trp Ala Ala Ala Arg Gly Gln Asp Asp Glu Val Arg Ile Leu Leu
            20                  25                  30

Ala Ala Gly Ala Asp Val Asn Ala Lys Asp Phe Gln Gly Ile Thr Pro
        35                  40                  45

Leu His Ile Ala Ala Gln Ser Gly His Leu Glu Ile Val Glu Val Leu
    50                  55                  60

Leu Lys Ala Gly Ala Asp Val Asn Ala Lys Asp Val Thr Gly Asp Thr
65                  70                  75                  80

Pro Leu His Leu Ala Ala Gln His Gly His Leu Val Ile Val Glu Val
                85                  90                  95

Leu Leu Lys Ala Gly Ala Asp Val Asn Ala Gln Asp Glu Arg Gly Trp
            100                 105                 110

Thr Pro Ala Asp Leu Ala Ala Asp Trp Gly His Glu Asp Ile Ala Glu
        115                 120                 125

Val Leu Gln Lys Leu Gly Gly Gly Ser Gly Gly Gly Ser Arg
    130                 135                 140

Ser Asp Leu Gly Lys Lys Leu Leu Glu Ala Ala Arg Ala Gly Gln Asp
145                 150                 155                 160

Asp Glu Val Arg Ile Leu Met Ala Asn Gly Ala Asp Val Asn Ala Lys
                165                 170                 175

Asp Glu Tyr Gly Leu Thr Pro Leu Tyr Leu Ala Thr Ala His Gly His
            180                 185                 190

Leu Glu Ile Val Glu Val Leu Leu Lys Asn Gly Ala Asp Val Asn Ala
        195                 200                 205

Val Asp Ala Ile Gly Phe Thr Pro Leu His Leu Ala Ala Phe Ile Gly
    210                 215                 220

His Leu Glu Ile Ala Glu Val Leu Leu Lys His Gly Ala Asp Val Asn
225                 230                 235                 240

Ala Gln Asp Lys Phe Gly Lys Thr Ala Phe Asp Ile Ser Ile Gly Asn
                245                 250                 255

Gly Asn Glu Asp Leu Ala Glu Ile Leu Gln Lys Ala Ala Gly Gly Gly
            260                 265                 270

Ser Gly Gly Gly Ser Cys
        275

<210> SEQ ID NO 137
<211> LENGTH: 414
<212> TYPE: PRT
<213> ORGANISM: Artificial Sequence
<220> FEATURE:

<223> OTHER INFORMATION: AR domain (three-domain)

<400> SEQUENCE: 137

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
            85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Leu Gly Gly Gly
        115                 120                 125

Gly Ser Gly Gly Gly Gly Ser Gly Gly Gly Ser Gly Gly Gly Gly
130                 135                 140

Ser Arg Ser Asp Leu Gly Ala Lys Leu Leu Ser Asp Leu Gly Val Lys
145                 150                 155                 160

Leu Leu Trp Ala Ala Ala Arg Gly Gln Asp Asp Glu Val Arg Ile Leu
            165                 170                 175

Leu Ala Ala Gly Ala Asp Val Asn Ala Lys Asp Phe Gln Gly Ile Thr
            180                 185                 190

Pro Leu His Ile Ala Ala Gln Ser Gly His Leu Glu Ile Val Glu Val
        195                 200                 205

Leu Leu Lys Ala Gly Ala Asp Val Asn Ala Lys Asp Val Thr Gly Asp
        210                 215                 220

Thr Pro Leu His Leu Ala Ala Gln His Gly His Leu Val Ile Val Glu
225                 230                 235                 240

Val Leu Leu Lys Ala Gly Ala Asp Val Asn Ala Gln Asp Glu Arg Gly
            245                 250                 255

Trp Thr Pro Ala Asp Leu Ala Ala Asp Trp Gly His Glu Asp Ile Ala
            260                 265                 270

Glu Val Leu Gln Lys Leu Gly Gly Gly Ser Gly Gly Gly Gly Ser
        275                 280                 285

Arg Ser Asp Leu Gly Lys Lys Leu Leu Glu Ala Ala Arg Ala Gly Gln
        290                 295                 300

Asp Asp Glu Val Arg Ile Leu Met Ala Asn Gly Ala Asp Val Asn Ala
305                 310                 315                 320

Lys Asp Glu Tyr Gly Leu Thr Pro Leu Tyr Leu Ala Thr Ala His Gly
            325                 330                 335

His Leu Glu Ile Val Glu Val Leu Leu Lys Asn Gly Ala Asp Val Asn
            340                 345                 350

Ala Val Asp Ala Ile Gly Phe Thr Pro Leu His Leu Ala Ala Phe Ile
            355                 360                 365

Gly His Leu Glu Ile Ala Glu Val Leu Leu Lys His Gly Ala Asp Val
        370                 375                 380

Asn Ala Gln Asp Lys Phe Gly Lys Thr Ala Phe Asp Ile Ser Ile Gly
385                 390                 395                 400
```

```
Asn Gly Asn Glu Asp Leu Ala Glu Ile Leu Gln Lys Leu Asn
            405                 410

<210> SEQ ID NO 138
<211> LENGTH: 417
<212> TYPE: PRT
<213> ORGANISM: Artificial Sequence
<220> FEATURE:
<223> OTHER INFORMATION: AR domain (three-domain)

<400> SEQUENCE: 138

Gly Ser Asp Leu Gly Ala Lys Leu Leu Ser Asp Leu Gly Val Lys Leu
1               5                   10                  15

Leu Trp Ala Ala Ala Arg Gly Gln Asp Asp Glu Val Arg Ile Leu Leu
            20                  25                  30

Ala Ala Gly Ala Asp Val Asn Ala Lys Asp Phe Gln Gly Ile Thr Pro
        35                  40                  45

Leu His Ile Ala Ala Gln Ser Gly His Leu Glu Ile Val Glu Val Leu
    50                  55                  60

Leu Lys Ala Gly Ala Asp Val Asn Ala Lys Asp Val Thr Gly Asp Thr
65                  70                  75                  80

Pro Leu His Leu Ala Ala Gln His Gly His Leu Val Ile Val Glu Val
                85                  90                  95

Leu Leu Lys Ala Gly Ala Asp Val Asn Ala Gln Asp Glu Arg Gly Trp
            100                 105                 110

Thr Pro Ala Asp Leu Ala Asp Trp Gly His Glu Asp Ile Ala Glu
        115                 120                 125

Val Leu Gln Lys Leu Gly Gly Gly Ser Gly Gly Gly Ser Arg
    130                 135                 140

Ser Asp Leu Gly Lys Lys Leu Leu Glu Ala Ala Arg Ala Gly Gln Asp
145                 150                 155                 160

Asp Glu Val Arg Ile Leu Met Ala Asn Gly Ala Asp Val Asn Ala Lys
                165                 170                 175

Asp Glu Tyr Gly Leu Thr Pro Leu Tyr Leu Ala Thr Ala His Gly His
            180                 185                 190

Leu Glu Ile Val Glu Val Leu Leu Lys Asn Gly Ala Asp Val Asn Ala
        195                 200                 205

Val Asp Ala Ile Gly Phe Thr Pro Leu His Leu Ala Ala Phe Ile Gly
    210                 215                 220

His Leu Glu Ile Ala Glu Val Leu Leu Lys His Gly Ala Asp Val Asn
225                 230                 235                 240

Ala Gln Asp Lys Phe Gly Lys Thr Ala Phe Asp Ile Ser Ile Gly Asn
                245                 250                 255

Gly Asn Glu Asp Leu Ala Glu Ile Leu Gln Lys Leu Asn Lys Leu Gly
            260                 265                 270

Gly Gly Ser Gly Gly Gly Ser Gly Gly Gly Ser Gly Gly
        275                 280                 285

Gly Gly Ser Arg Ser Asp Leu Gly Lys Lys Leu Leu Glu Ala Ala Arg
    290                 295                 300

Ala Gly Gln Asp Asp Glu Val Arg Ile Leu Met Ala Asn Gly Ala Asp
305                 310                 315                 320

Val Asn Ala Lys Asp Tyr Phe Ser His Thr Pro Leu His Leu Ala Ala
                325                 330                 335

Arg Asn Gly His Leu Lys Ile Val Glu Val Leu Leu Lys Ala Gly Ala
            340                 345                 350
```

```
Asp Val Asn Ala Lys Asp Phe Ala Gly Lys Thr Pro Leu His Leu Ala
            355                 360                 365

Ala Asn Asp Gly His Leu Glu Ile Val Glu Val Leu Leu Lys His Gly
        370                 375                 380

Ala Asp Val Asn Ala Gln Asp Ile Phe Gly Lys Thr Pro Ala Asp Ile
385                 390                 395                 400

Ala Ala Asp Ala Gly His Glu Asp Ile Ala Glu Val Leu Gln Lys Leu
                405                 410                 415

Asn

<210> SEQ ID NO 139
<211> LENGTH: 260
<212> TYPE: PRT
<213> ORGANISM: Artificial Sequence
<220> FEATURE:
<223> OTHER INFORMATION: AR domain (two-domain)

<400> SEQUENCE: 139

Gly Ser Asp Leu Gly Ala Lys Leu Leu Ser Asp Leu Gly Val Lys Leu
1               5                   10                  15

Leu Trp Ala Ala Ala Arg Gly Gln Asp Asp Glu Val Arg Ile Leu Leu
            20                  25                  30

Ala Ala Gly Ala Asp Val Asn Ala Lys Asp Phe Gln Gly Ile Thr Pro
        35                  40                  45

Leu His Ile Ala Ala Gln Ser Gly His Leu Glu Ile Val Glu Val Leu
    50                  55                  60

Leu Lys Ala Gly Ala Asp Val Asn Ala Lys Asp Val Thr Gly Asp Thr
65                  70                  75                  80

Pro Leu His Leu Ala Ala Gln His Gly His Leu Val Ile Val Glu Val
                85                  90                  95

Leu Leu Lys Ala Gly Ala Asp Val Asn Ala Gln Asp Glu Arg Gly Trp
            100                 105                 110

Thr Pro Ala Asp Leu Ala Ala Asp Trp Gly His Glu Asp Ile Ala Glu
        115                 120                 125

Val Leu Gln Lys Ala Ala Gly Ser Asp Leu Gly Lys Lys Leu Leu Glu
    130                 135                 140

Ala Ala Arg Ala Gly Gln Asp Asp Glu Val Arg Ile Leu Met Ala Asn
145                 150                 155                 160

Gly Ala Asp Val Asn Ala Lys Asp Glu Tyr Gly Leu Thr Pro Leu Tyr
                165                 170                 175

Leu Ala Thr Ala His Gly His Leu Glu Ile Val Glu Val Leu Leu Lys
            180                 185                 190

Asn Gly Ala Asp Val Asn Ala Val Asp Ala Ile Gly Phe Thr Pro Leu
        195                 200                 205

His Leu Ala Ala Phe Ile Gly His Leu Glu Ile Ala Glu Val Leu Leu
    210                 215                 220

Lys His Gly Ala Asp Val Asn Gln Asp Lys Phe Gly Lys Thr Ala
225                 230                 235                 240

Phe Asp Ile Ser Ile Gly Asn Gly Asn Glu Asp Leu Ala Glu Ile Leu
                245                 250                 255

Gln Lys Ala Ala
            260

<210> SEQ ID NO 140
<211> LENGTH: 263
<212> TYPE: PRT
```

<213> ORGANISM: Artificial Sequence
<220> FEATURE:
<223> OTHER INFORMATION: AR domain (two-domain)

<400> SEQUENCE: 140

Gly Ser Asp Leu Gly Ala Lys Leu Leu Ser Asp Leu Gly Val Lys Leu
1               5                   10                  15

Leu Trp Ala Ala Ala Arg Gly Gln Asp Asp Glu Val Arg Ile Leu Leu
            20                  25                  30

Ala Ala Gly Ala Asp Val Asn Ala Lys Asp Phe Gln Gly Ile Thr Pro
        35                  40                  45

Leu His Ile Ala Ala Gln Ser Gly His Leu Glu Ile Val Glu Val Leu
    50                  55                  60

Leu Lys Ala Gly Ala Asp Val Asn Ala Lys Val Thr Gly Asp Thr
65                  70                  75                  80

Pro Leu His Leu Ala Ala Gln His Gly His Leu Val Ile Val Glu Val
                85                  90                  95

Leu Leu Lys Ala Gly Ala Asp Val Asn Ala Gln Asp Glu Arg Gly Trp
            100                 105                 110

Thr Pro Ala Asp Leu Ala Ala Asp Trp Gly His Glu Asp Ile Ala Glu
        115                 120                 125

Val Leu Gln Lys Ala Ala Gly Gly Gly Ser Asp Leu Gly Lys Lys
130                 135                 140

Leu Leu Glu Ala Ala Arg Ala Gly Gln Asp Asp Glu Val Arg Ile Leu
145                 150                 155                 160

Met Ala Asn Gly Ala Asp Val Asn Ala Lys Asp Glu Tyr Gly Leu Thr
                165                 170                 175

Pro Leu Tyr Leu Ala Thr Ala His Gly His Leu Glu Ile Val Glu Val
            180                 185                 190

Leu Leu Lys Asn Gly Ala Asp Val Asn Ala Val Asp Ala Ile Gly Phe
        195                 200                 205

Thr Pro Leu His Leu Ala Ala Phe Ile Gly His Leu Glu Ile Ala Glu
    210                 215                 220

Val Leu Leu Lys His Gly Ala Asp Val Asn Ala Gln Asp Lys Phe Gly
225                 230                 235                 240

Lys Thr Ala Phe Asp Ile Ser Ile Gly Asn Gly Asn Glu Asp Leu Ala
                245                 250                 255

Glu Ile Leu Gln Lys Ala Ala
            260

<210> SEQ ID NO 141
<211> LENGTH: 282
<212> TYPE: PRT
<213> ORGANISM: Artificial Sequence
<220> FEATURE:
<223> OTHER INFORMATION: AR domain (two-domain)

<400> SEQUENCE: 141

Gly Ser Asp Leu Gly Ala Lys Leu Leu Ser Asp Leu Gly Val Lys Leu
1               5                   10                  15

Leu Trp Ala Ala Ala Arg Gly Gln Asp Asp Glu Val Arg Ile Leu Leu
            20                  25                  30

Ala Ala Gly Ala Asp Val Asn Ala Lys Asp Phe Gln Gly Ile Thr Pro
        35                  40                  45

Leu His Ile Ala Ala Gln Ser Gly His Leu Glu Ile Val Glu Val Leu
    50                  55                  60

```
Leu Lys Ala Gly Ala Asp Val Asn Ala Lys Asp Val Thr Gly Asp Thr
 65              70                  75                  80

Pro Leu His Leu Ala Ala Gln His Gly His Leu Val Ile Val Glu Val
             85                  90                  95

Leu Leu Lys Ala Gly Ala Asp Val Asn Ala Gln Asp Glu Arg Gly Trp
            100                 105                 110

Thr Pro Ala Asp Leu Ala Ala Asp Trp Gly His Glu Asp Ile Ala Glu
            115                 120                 125

Val Leu Gln Lys Ala Ala Gly Ser Pro Thr Pro Thr Pro Thr Thr Pro
    130                 135                 140

Thr Pro Thr Pro Thr Thr Pro Thr Pro Thr Pro Thr Gly Ser Asp Leu
145                 150                 155                 160

Gly Lys Lys Leu Leu Glu Ala Ala Arg Ala Gly Gln Asp Asp Glu Val
                165                 170                 175

Arg Ile Leu Met Ala Asn Gly Ala Asp Val Asn Ala Lys Asp Glu Tyr
                180                 185                 190

Gly Leu Thr Pro Leu Tyr Leu Ala Thr Ala His Gly His Leu Glu Ile
            195                 200                 205

Val Glu Val Leu Leu Lys Asn Gly Ala Asp Val Asn Ala Val Asp Ala
    210                 215                 220

Ile Gly Phe Thr Pro Leu His Leu Ala Ala Phe Ile Gly His Leu Glu
225                 230                 235                 240

Ile Ala Glu Val Leu Leu Lys His Gly Ala Asp Val Asn Ala Gln Asp
                245                 250                 255

Lys Phe Gly Lys Thr Ala Phe Asp Ile Ser Ile Gly Asn Gly Asn Glu
            260                 265                 270

Asp Leu Ala Glu Ile Leu Gln Lys Ala Ala
            275                 280
```